United States Patent
Iba et al.

(10) Patent No.: US 8,563,709 B2
(45) Date of Patent: Oct. 22, 2013

(54) METHOD FOR INHIBITING FUNCTION OF MICRO-RNA

(75) Inventors: Hideo Iba, Tokyo (JP); Takeshi Haraguchi, Tokyo (JP)

(73) Assignee: The University of Tokyo, Tokyo (JP)

( * ) Notice: Subject to any disclaimer, the term of this patent is extended or adjusted under 35 U.S.C. 154(b) by 55 days.

(21) Appl. No.: 13/039,156

(22) Filed: Mar. 2, 2011

(65) Prior Publication Data

US 2011/0245481 A1 Oct. 6, 2011

Related U.S. Application Data

(63) Continuation-in-part of application No. PCT/JP2009/067251, filed on Oct. 2, 2009.

(30) Foreign Application Priority Data

Oct. 23, 2008 (JP) ................ 2008-273562
Jan. 22, 2009 (JP) ................ 2009-011877

(51) Int. Cl.
*C07H 21/04* (2006.01)
*C12N 15/11* (2006.01)

(52) U.S. Cl.
USPC ................... 536/24.5; 514/44 A

(58) Field of Classification Search
USPC ................... 536/24.5; 514/44 A
See application file for complete search history.

(56) References Cited

U.S. PATENT DOCUMENTS

2002/0156261 A1 10/2002 Malvy et al.

FOREIGN PATENT DOCUMENTS

WO 00/17346 A2 3/2000
WO 2007/095387 A2 8/2007

OTHER PUBLICATIONS

Haraguchi, et al., "Vectors expressing efficient RNA decoys achieve the long-term suppression of specific microRNA activity in mamalian cells", Nucleic Acids Research, 2009 vol. 37, No. 6, e(43), published online on Feb. 17, 2009.
Orom, et al., LNA-modified oligonucleotides mediate specific inhibition of microRNA function, Gene Section Functional Genomics, Vo. 372, pp. 137-141, published online on Feb. 24, 2006.
Sayed, et al., "MicroRNA-21 Targets Sprouty2 and Promotes Cellular Outgrowths", Molecular Biology of the Cell, vol. 19, pp. 3272-3282, published online on May 28, 2008.
Bartel, "MicroRNAs: Genomics, Biogenesis, Mechanism, and Function", Cell, vol. 116, pp. 281-297, Jan. 23, 2004.
Lewis, et al., "Conserved Seed Pairing, Often Flanked by Adenosines, Indicates that Thousands of Human Genes are MicroRNA Targets", Cell, vol. 120, pp. 15-20, Jan. 14, 2005.
Ambros, et al., RNA, "A uniform system for microRNA annotation", RNA, vol. 9, pp. 277-279, published by Cold Spring Harbor Laboratory Press., 2003.

(Continued)

*Primary Examiner* — J E Angell
(74) *Attorney, Agent, or Firm* — Knobbe, Martens, Olson & Bear, LLP

(57) ABSTRACT

A miRNA-inhibiting RNA complex has a double-stranded structure, in which at least one RNA strand that includes a miRNA-binding sequence is linked to the two strands at at least one end of the double-stranded structure. The complex can efficiently inhibit miRNAs. In particular, RNAs in which two RNAs containing a miRNA binding sequence are positioned between two double-stranded structures were able to strongly inhibit miRNA. These RNAs can be expressed from, for example, a PolIII promoter, and by integration into a vector, miRNAs can be stably inhibited for a long period of time.

17 Claims, 36 Drawing Sheets

(56) References Cited

OTHER PUBLICATIONS

Li, et al., "miR-181a Is an Intrinsic Modulator of T Cell Sensitivity and Selection", Cell, vol. 129, pp. 147-161, Published Online Mar. 22, 2007.
Lu, et al., "MicroRNA expression profiles classify human cancers", Nature, vol. 435, pp. 834-838, Jun. 9, 2005.
Lecellier, et al., "A Cellular MicroRNA Mediates Antiviral Defense in Human Cells", Science, vol. 308, pp. 557-560, Apr. 22, 2005.
Hutvagner, et al., "Sequence-Specific Inhibition of Small RNA Function", PLoS Biology, vol. 2, issue 4, pp. 0465-0475, published online Feb. 24, 2004.
Meister, et al., "Sequence-specific inhibition of MicroRNA- and SiRNA-induced RNA silencing", RNA, vol. 10, No. 3, pp. 544-550, 2004.
Krutzfeldt, et al., "Silencing of MicroRNAs in vivo with antagomirs" Nature, vol. 438, pp. 685-689, published online Oct. 30, 2005.
Krutzfeldt, et al., "Specificity, duplex degradation and subcellular localization of antagomirs" Nucleic Acids Research, vol. No. 35, pp. 2885-2892, published online Apr. 16, 2007.
Davis, et al., "Improved targeting of miRNA with antisense oligonucleotides" Nucleic Acids Research, vol. 34, No. 8, pp. 2294-2304, published online May 11, 2006.
Fujita, et al., "Putative Promoter Regions of miRNA genes involved in evolutionarily conserved regulatory systems among vertebrates" Bioinformatics, Discovery Note, vol. 24, No. 3, pp. 303-308, published online Nov. 30, 2007.
Singh, et al., "REST maintains self-renewal and pluripotency of embryonic stem cells" Nature, vol. 453, pp. 223-227, published online Mar. 23, 2008.
Fujita, et al., "miR-21 Gene Expression Triggered by AP-1 is Sustained through a Double-Negative Feedback Mechanism", J Mol Biol., vol. 378, No. 3, pp. 492-504, published online Mar. 15, 2008.
Hammond, "Soaking up small RNAs", Nature Methods, vol. 4, No. 9, pp. 694-695, Sep. 2007.
Haraguchi, Hideo IBA, "miR-21 no Hatsugen Koshin to Hatsugan", Experimental Medicine, May 2009, vol. 27, No. 8, pp. 1201 to 1207.
International Search Report issued on Dec. 28, 2009 for International Application No. PCT/JP2009/067251.
Ebert, M. S. et al., MicroRNA sponges: competitive inhibitors of small RNAs in mammalian cells, Nat. Methods, 2007, vol. 4, No. 9, pp. 721-726.
Vermeulen, A. et al., Double-stranded regions are essential design components of potent inhibitors of RISC function, RNA, 2007, vol. 13, pp. 723-730.
Scherr, M. et al., Lentivirus-mediated antagomir expression for specific inhibition of miRNA function, Nucleic Acids Res., 2007, vol. 35, No. 22, e149.
International Preliminary Report on Patentability and Written Opinion of the International Searching Authority dated May 17, 2011 issued in PCT/JP2009/067251.
Bak, R.O. et al. 2013 "Potent microRNA suppression by RNA Pol II-transcribed 'Tough Decoy' inhibitors" RNA 19: 280-293.
Xie, J. et al. 2012 "Long-term, efficient inhibition of microRNA function in mice using rAAV vectors" Nature Methods 9 (4): 403-409.
Hartig et al., "Sequence-Specific Detection of MicroRNAs by Signal-Amplifying Rubozymes", J Am Chem Soc. Jan. 28, 2004; 126(3) :722-3.
Mourelatos et al., "miRNPs: a novel class of ribonucleoproteins containing numerous microRNAs", Genes Dev. Mar. 15, 2002; 16(6) :720-8.

| DECOY RNA | STEM LENGTH | RELATIVE GFP EXPRESSION (%) |
|---|---|---|
| NC | - | 16.9±0.7 |
| #1 | 17 | 23.5±1.2 |
| #2 | 18 | 24.4±0.8 |
| #3 | 19 | 22.2±1.5 |
| #4 | 20 | 21.1±1.5 |
| #5 | 21 | 23.8±3.6 |
| #6 | 24 | 22.4±2.5 |

(A)
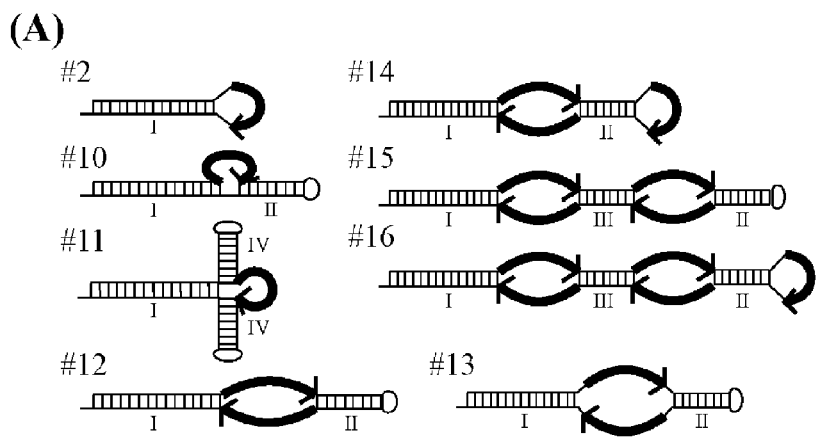
(B)
| DECOY RNA | STEM LENGTH (bp) | | | | RELATIVE GFP EXPRESSION (%) |
|---|---|---|---|---|---|
| | I | II | III | IV | |
| NC | - | - | - | - | 16.9±0.7 |
| #2 | 18 | - | - | - | 24.4±0.8 |
| #10 | 18 | 8 | - | - | 28.2±2.6 |
| #11 | 18 | - | - | 8 | 26.1±1.8 |
| #12 | 18 | 8 | - | - | 33.7±2.7 |
| #14 | 18 | 8 | - | - | 42.4±2.9 |
| #15 | 18 | 8 | 8 | - | 51.7±1.1 |
| #16 | 18 | 8 | 8 | - | 55.2±1.3 |
| #13 | 18 | 8 | - | - | 99.5±5.7 |
(C) 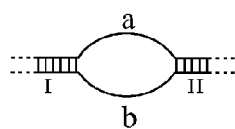
(D) 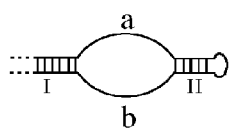
FIG. 2

| DECOY RNA | MBS SEQUENCE | RELATIVE GFP EXPRESSION (%) | |
|---|---|---|---|
| NC | | 16.9±0.7 | |
| #2 | MBS      5'- UCCGUGGUUCUACCCUGUGGUA -3'<br>miR140-3p 3'- AGGCACCAAGAUGGGACACCAU -5' | 24.4±0.8 | (SEQ ID NO: 81)<br>(SEQ ID NO: 82) |
| #17 | MBS      5'- UCCGUGGUUCUA$^A$CCCUGUGGUA -3'<br>miR140-3p 3'- AGGCACCAAGAU-GGGACACCAU -5' | 32.5±3.2 | (SEQ ID NO: 83)<br>(SEQ ID NO: 82) |
| #18 | MBS      5'- UCCGUGGUUCUA$^{AU}$CCCUGUGGUA -3'<br>miR140-3p 3'- AGGCACCAAGAU--GGGACACCAU -5' | 36.7±5.4 | (SEQ ID NO: 84)<br>(SEQ ID NO: 82) |
| #19 | MBS      5'- UCCGUGGUUCUA$^{A\,U}_{\,UC}$CCCUGUGGUA -3'<br>miR140-3p 3'- AGGCACCAAGAU--GGGACACCAU -5' | 45.4±6.0 | (SEQ ID NO: 85)<br>(SEQ ID NO: 82) |
| #20 | MBS      5'- UCCGUGGUUCUA$^{A\,U}_{UC}$CCCUGUGGUA -3'<br>miR140-3p 3'- AGGCACCAAGAU--GGGACACCAU -5' | 52.0±6.4 | (SEQ ID NO: 86)<br>(SEQ ID NO: 82) |

FIG. 3

| DECOY RNA | MBS SEQUENCE | SCHEMATIC DIAGRAM | RELATIVE GFP EXPRESSION (%) |
|---|---|---|---|
| NC | (SEQ ID NO: 81) | | 16.9±0.7 |
| #13 | MBS 5'- UCCGUGGUUCUACCCUGUGGUA -3'<br>miR140-3p 3'- AGGCACCAAGAUGGGACACCAU -5'<br>(SEQ ID NO: 82) | | 101.3±5.7 |
| #24 | MBS 5'- UCCGUGGUUCUA$^{UC}_{AU}$CCCUGUGGUA -3'<br>miR140-3p 3'- AGGCACCAAGAU--GGGACACCAU -5'<br>(SEQ ID NO: 86) | | 100.0±2.7 |
| #27 | (SEQ ID NO: 82) | | 80.1±2.5 |

FIG. 5

(A) pMXs-GIN-miR140-3pT
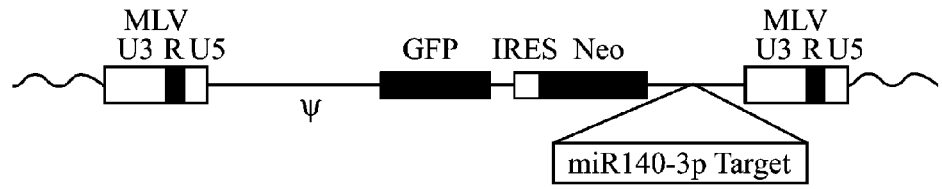
(B) pMXs-GIN-miR140-5pT
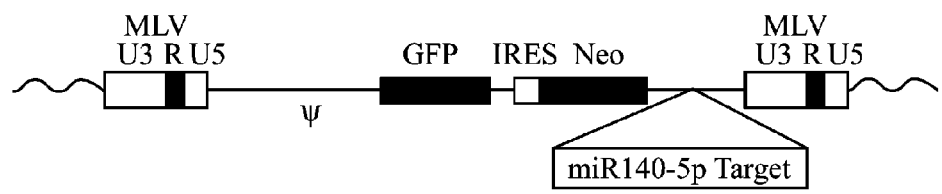
(C) pSSCH-miR140-5p/140-3p
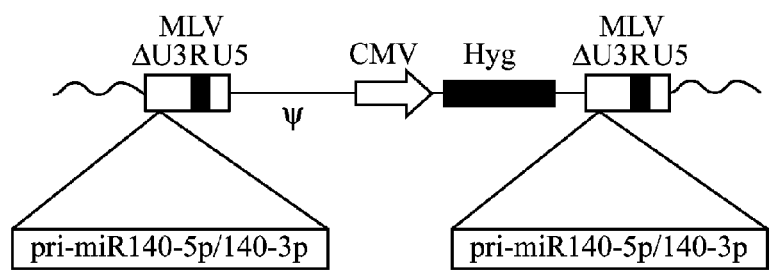
(D) DECOY RNA-EXPRESSING LENTIVIRAL VECTOR
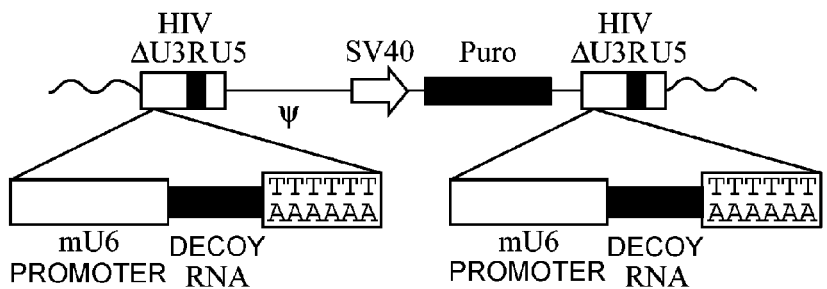
FIG. 15

(A) pTK4.12C.P-
(B) pGL4.74
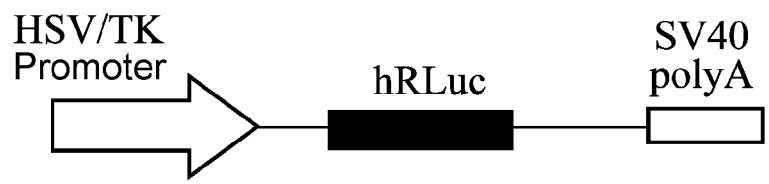
(C) pGL4.74-miR21T
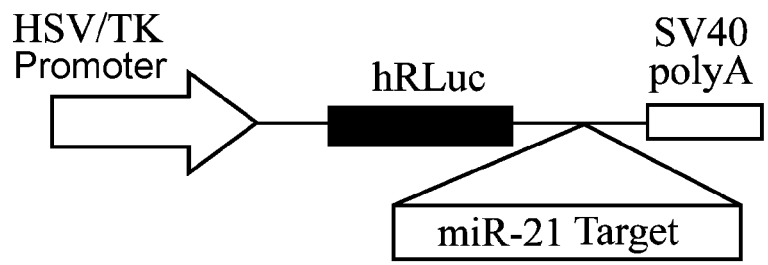
(D) pGL4.74-miR16T
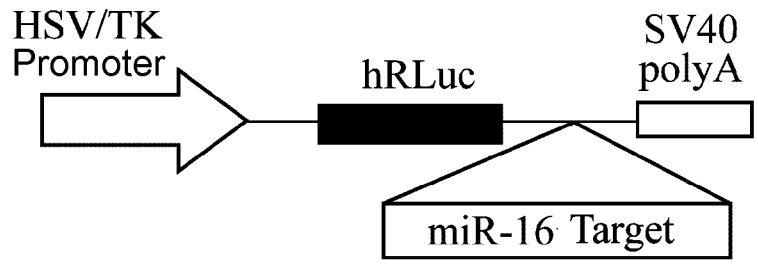
FIG. 17

| | |
|---|---|
| TuD-miR140-3p-pf<br>(SEQ ID NO:81)<br>MBS 5'- UCCGUGGUUCUACCCUGUGGUA -3'<br>miR140-3p 3'- AGGCACCAAGAUGGGACACCAU -5'<br>(SEQ ID NO:82) | MBS<br>5'- GACGGCGCUAGGAUCAUC^AAC-U^CCGUGG^UUCUACC^CUGUGG^UACAA^GUAUCUG^G_U<br>3'- UUCUGCCGCGAUCCUAGUAG_AACAU_CCAUCUU_U-CAA_CAUAAGAC_C_A<br>(SEQ ID NO:110)<br>MBS |
| TuD-miR140-3p-4ntin<br>(SEQ ID NO:86)<br>MBS 5'- UCCGUGGUUCUA^UC_A CCCUGUGGUA -3'<br>miR140-3p 3'- AGGCACCAAGAU--GGGACACCAU -5'<br>(SEQ ID NO:82) | MBS<br>5'- GACGGCGCUAGGAUCAUC^AAC-U^CCGUGG^UUCUAAUCUCC^CUGUGG^UACAA^GUAUUCUG^G_U<br>3'- UUCUGCCGCGAUCCUAGUAG_AACAU_GGUGUC_CCUCUAAUCUU_GGUGCC_U CAA_CAUAAGAC_C_A<br>(SEQ ID NO:120)<br>MBS |
| TuD-miR140-5p-4ntin<br>(SEQ ID NO:124)<br>MBS 5'- CUACCAUAGGGU^AU_C AAAACCACUG -3'<br>miR140-5p 3'- GAUGGUAUCCCA--UUUUGGUGAC -5'<br>(SEQ ID NO:125) | MBS<br>5'- GACGGCGCUAGGAUCAUC^AACCUACCAUAG^GGU^CAUCAAC^ACC^-----^ACUGCAA^GUAUCUG^G_U<br>3'- UUCUGCCGCGAUCCUAGUAG_AACGUCA-----_CCA_AAACUAC_UGG_GAUACCAUCCAA_CAUAAGAC_C_A<br>(SEQ ID NO:129)<br>MBS |
| TuD-miR21-4ntin<br>(SEQ ID NO:126)<br>MBS 5'- UCAACAUCAGUC^AU_G UGAUAAGCUA -3'<br>miR21 3'- AGUUGUAGCAG--ACUAUUCGAU -5'<br>(SEQ ID NO:27) | MBS<br>5'- GACGGCGCUAGGAUCAUC^AACUCAACAUCA^GUCA^AUG^UGAU^---AAGCUACAA^GUAUUCUG^G_U<br>3'- UUCUGCCGCGAUCCUAGUAG_AACAUGGAA_UAGU_GUA_ACUG_ACUACAACUCAA_CAUAAGAC_C_A<br>(SEQ ID NO:130)<br>MBS |
| TuD-miR21-pf<br>(SEQ ID NO:128)<br>MBS 5'- UCAACAUCAGUCUGAUAAGCUA -3'<br>miR21 3'- AGUUGUAGCAGACUAUUCGAU -5'<br>(SEQ ID NO:127) | MBS<br>5'- GACGCGCGUAGGAUCAUC^AACUCAAC-^AUCAG^U^CUGAU^AAGCUACAA^GUAUUCUG^G_U<br>3'- UUCUGCCGCGAUCCUAGUAG_AACAUCGAA_UAGUC_GACUA_-CAACUCAA_CAUAAGAC_C_A<br>(SEQ ID NO:131)<br>MBS |
| TuD-miR16-4ntin<br>(SEQ ID NO:142)<br>MBS 5'- CGCCAAUAUUUA^AU_GC CGUGCUGCUA -3'<br>miR16 3'- GCGGUUAUAAAU--GCACGACGAU -5'<br>(SEQ ID NO:140) | MBS<br>5'- GACGGCGCUAGGAUCAUC^AACCGCCAAUAUUUA^---CGUGCUGCUACAA^GUAUUCUG^G_U<br>3'- UUCUGCCGCGAUCCUAGUAG_AACAUCGUCGUGC-_GAUC_CUAG_AUUUAUAACCGCCAA_CAUAAGAC_C_A<br>(SEQ ID NO:145)<br>MBS |
| TuD-miR195-4ntin<br>(SEQ ID NO:143)<br>MBS 5'- GCCAAUAUUU^C_G UGUGCUGCUA -3'<br>miR16 3'- GCGGUUAUAAAA^U---GCACGACGAU -5'<br>(SEQ ID NO:140) | MBS<br>5'- GACGGCGCUAGGAUCAUC^AACGCCAAUAUUUCAAUGUG^U^GC^GC^---------------UACAA^GUAUUCUG^G_U<br>3'- UUCUGCCGCGAUCCUAGUAG_AACAU---------------_CG_CG_UGUGUAACUUUAUAACCGCAA_CAUAAGAC_C_A<br>(SEQ ID NO:146)<br>MBS |
| TuD-miR497-4ntin<br>(SEQ ID NO:144)<br>MBS 5'- ACAAA^CCA^CAGAAUC UGUGCUGCUG -3'<br>miR16 3'- GC^GGU^UAUAAAU GCACGACGAU -5'<br>(SEQ ID NO:140) | MBS<br>5'- GACGGCGCUAGGAUCAUC^AACACAAA^CACAGA^A^UCUGUG^CUGCUGCAA^GJAUUCUG^G_U<br>3'- UUCUGCCGCGAUCCUAGUAG_AACGUCGUC_GUGUCU_ACACAC_A_CAAACACAA_CAUAAGAC_C_A<br>(SEQ ID NO:147)<br>MBS |
| TuD-NC | MBS<br>5'- GACGGCGCUAGGAUCAUC^AACAAGCCACAAC^A^UC^UCUAUAUCAUCAA^GUAUUCUG^G_U<br>3'- UUCUGCCGCGAUCCUAGUAG_AACUACUAUAUCU_GA_UC_AG_A_CAACACCGAACAA_CAUAAGAC_C_A<br>(SEQ ID NO:132)<br>MBS |

FIG. 18

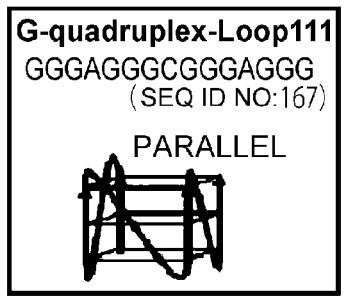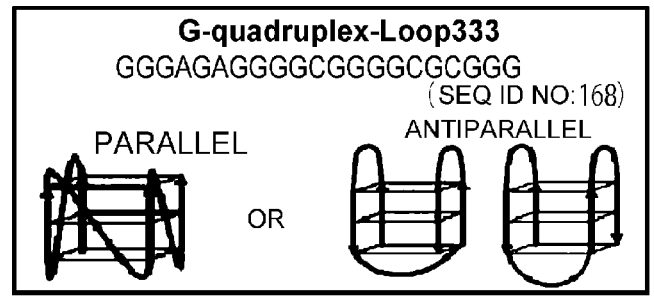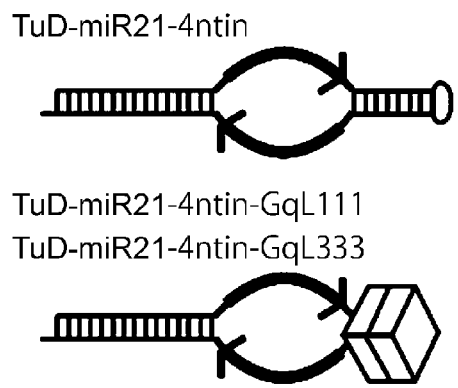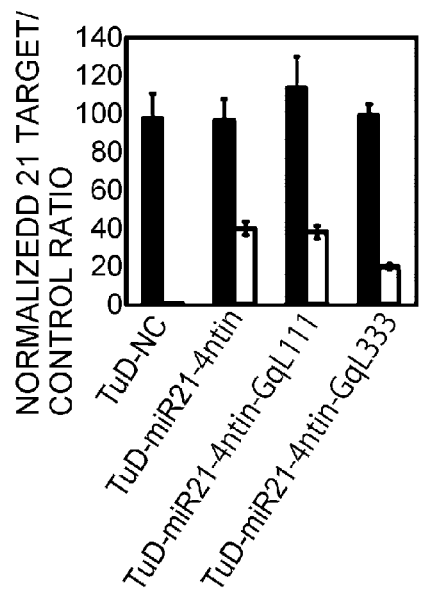
FIG. 25

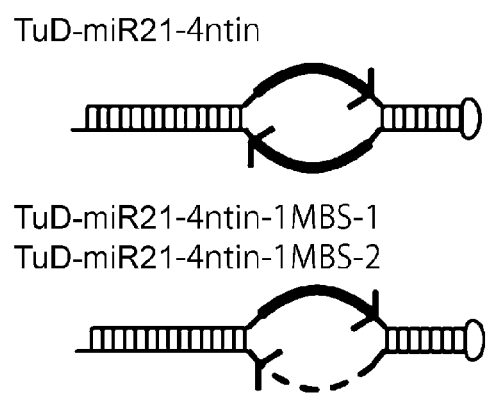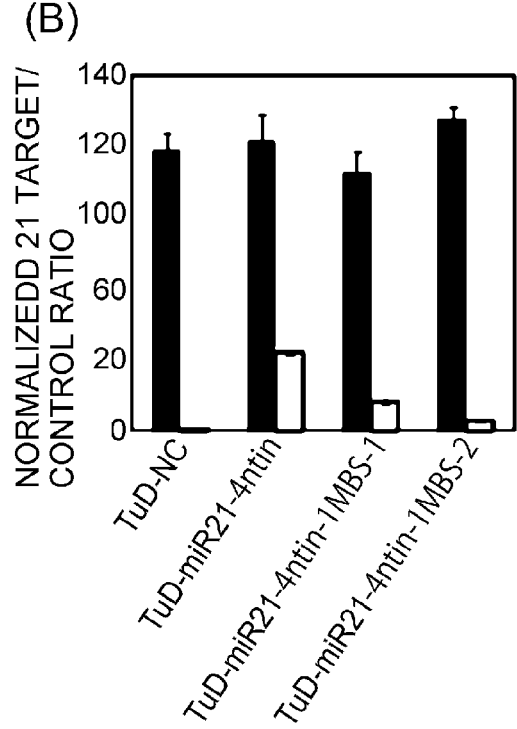
FIG. 26

A pTK4.12
B pGL4.74
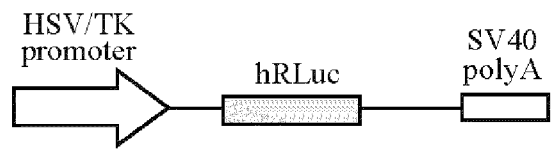
C pGL4.74-miR21T
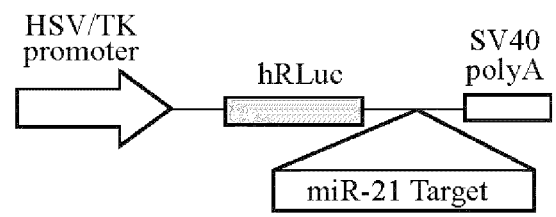
D pGL4.74-miR200cT
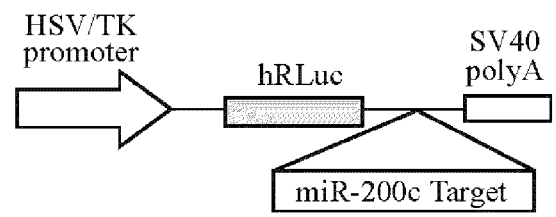
E pGL4.74-miR16T
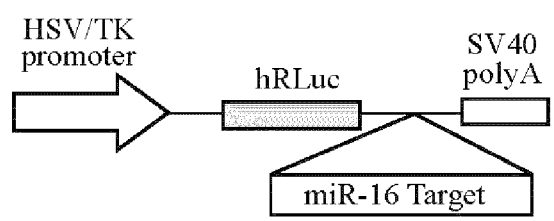
FIG. 30

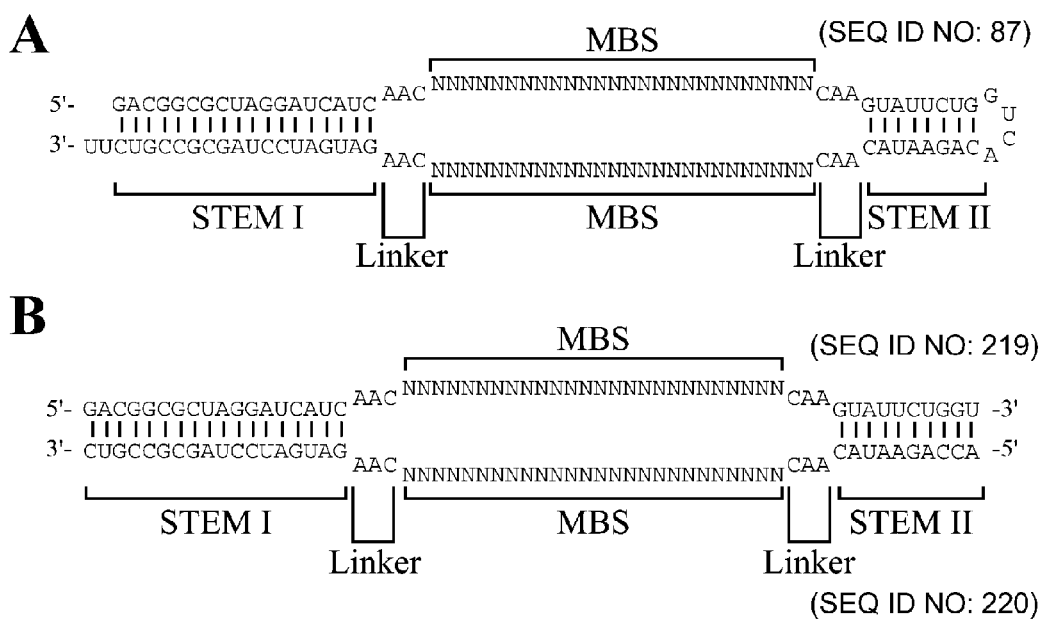
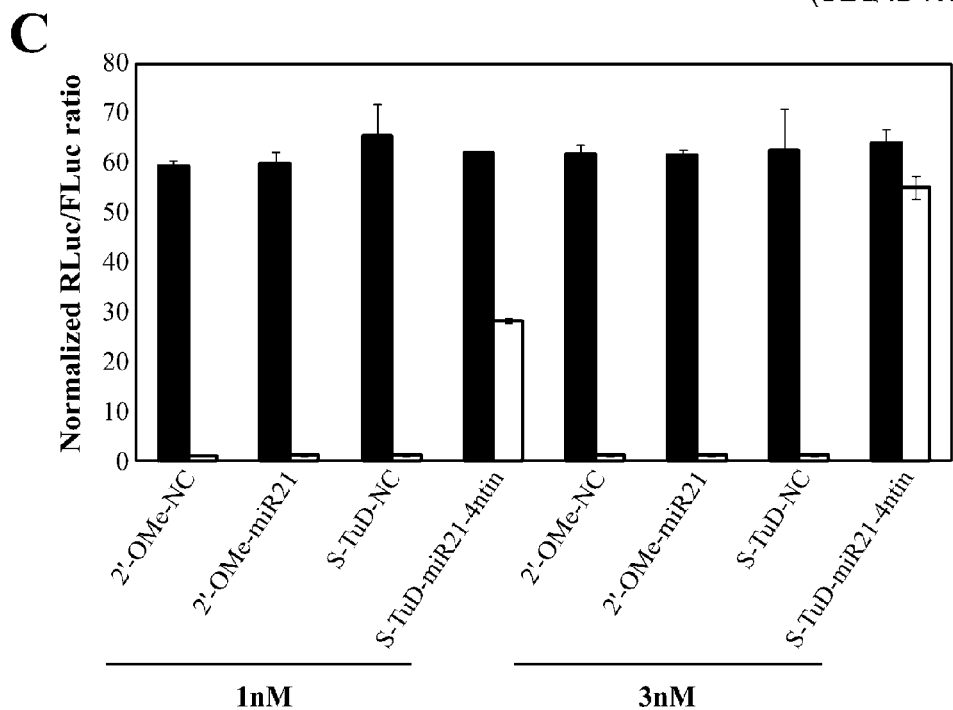
FIG. 31

| | |
|---|---|
| S-TuD-miR21-pf | MBS (SEQ ID NO: 185)<br>5'- GACGGCGCUAGGAUCAUC AACUCAAC- U AAGCUACAA GUAUUCUGGU -3'<br>          AUCAG CUGAU<br>3'- CUGCCGCGAUCCUAGUAG UAGUC GACUA CAUAAGACCA -5'<br>          AACAUCGAA U -CAACUCAA<br>(SEQ ID NO: 186)<br>MBS |
| (SEQ ID NO: 128)<br>MBS 5'- UCAACAUCAGUCUGAUAAGCUA -3'<br>miR-21 3'- AGUUGUAGUCAGACUAUUCGAU -5'<br>(SEQ ID NO: 127) | |
| S-TuD-miR21-4ntin | MBS (SEQ ID NO: 148)<br>5'- GACGGCGCUAGGAUCAUC AACUCAACA AGU AAU -U- UAACCUACAA GUAUUCUGGU -3'<br>          UC C G GA<br>3'- CUGCCGCGAUCCUAGUAG AG G C CU CAUAAGACCA -5'<br>          AACAUCGAAU -U- UAA UGA -ACAACUCAA<br>(SEQ ID NO: 149)<br>MBS |
|         AU (SEQ ID NO: 126)<br>        A G<br>MBS 5'- UCAACAUCAGUC UGAUAAGCUA -3'<br>miR-21 3'- AGUUGUAGUCAG--ACUAUUCGAU -5'<br>(SEQ ID NO: 127) | |
| S-TuD-miR21-10mut | MBS (SEQ ID NO: 187)<br>5'- GACGGCGCUAGGAUCAUC AACUCAAC- A U C AAGCUACAA GUAUUCUGGU -3'<br>          AUC G C GAU<br>3'- CUGCCGCGAUCCUAGUAG UAG C G CUA CAUAAGACCA -5'<br>          AACAUCGAA C U A -CAACUCAA<br>(SEQ ID NO: 188)<br>MBS |
|            C (SEQ ID NO: 221)<br>MBS 5'- UCAACAUCAGUC GAUAAGCUA -3'<br>miR-21 3'- AGUUGUAGUCAG CUAUUCGAU -5'<br>           A<br>(SEQ ID NO: 127) | |
| S-TuD-miR200c-pf | MBS (SEQ ID NO: 189)<br>5'- GACGGCGCUAGGAUCAUC AACUCCAUCAUUAC CA ----UAUUACAA GUAUUCUGGU -3'<br>          CCGG G<br>3'- CUGCCGCGAUCCUAGUAG GGCC--C CAUAAGACCA -5'<br>          AACAUUAUGAC--- AUUACUACCAA<br>(SEQ ID NO: 190)<br>MBS |
| (SEQ ID NO: 222)<br>MBS 5'- UCCAUCAUUACCCGGCAGUAUUA -3'<br>miR-200c 3'- AGGUAGUAAUGGGCCGUCAUAAU -5'<br>(SEQ ID NO: 205) | |
| S-TuD-miR200c-4ntin | MBS (SEQ ID NO: 191)<br>5'- GACGGCGCUAGGAUCAUC AACUCCAUCAU C- C CA -----UUACAA GUAUUCUGGU -3'<br>          UAC CCA UGG GUA<br>3'- CUGCCGCGAUCCUAGUAG AUG GGU ACC CAU CAUAAGACCA -5'<br>          AACAUU---- AC C -C UACUACCAA<br>(SEQ ID NO: 192)<br>MBS |
| (SEQ ID NO: 206) AC<br>           C U<br>MBS 5'- UCCAUCAUUACCC GGCAGUAUUA -3'<br>miR-200c 3'- AGGUAGUAAUGGG--CCGUCAUAAU -5'<br>(SEQ ID NO: 205) | |
| S-TuD-miR200c-10mut | MBS (SEQ ID NO: 195)<br>5'- GACGGCGCUAGGAUCAUC AACUCCAUCAUUACCCA -------AGUAUACAA GUAUUCUGGU -3'<br>          GC<br>3'- CUGCCGCGAUCCUAGUAG CG CAUAAGACCA -5'<br>          AACAUUAUGA------- ACCCAUUACUACCUCAA<br>(SEQ ID NO: 196)<br>MBS |
| (SEQ ID NO: 207) A<br>MBS 5'- UCCAUCAUUACCC GCAGUAUUA -3'<br>miR-200c 3'- AGGUAGUAAUGGG CGUCAUAAU -5'<br>             C<br>(SEQ ID NO: 205) | |
| S-TuD-miR16-pf | MBS (SEQ ID NO: 197)<br>5'- GACGGCGCUAGGAUCAUC AACC- CAAUAUUU ACGU --GCU--- UACAA GUAUUCUGGU -3'<br>          GC GC<br>3'- CUGCCGCGAUCCUAGUAG CG UGCA CG CAUAAGACCA -5'<br>          AACAU ----UCG-- UUUAUAAC -CCAA<br>(SEQ ID NO: 198)<br>MBS |
| (SEQ ID NO: 208)<br>MBS 5'- CGCCAAUAUUUACGUGCUGCUA -3'<br>miR-16 3'- GCGGUUAUAAAUGCACGACGAU -5'<br>(SEQ ID NO: 140) | |
| S-TuD-miR16-4ntin | MBS (SEQ ID NO: 199)<br>5'- GACGGCGCUAGGAUCAUC AACC- CAAUAUUUAGUUCCGUGCU UACAA GUAUUCUGGU -3'<br>          GC GC<br>3'- CUGCCGCGAUCCUAGUAG CG CG CAUAAGACCA -5'<br>          AACAU UCGUGCCUUGAUUUAUAAC -CCAA<br>(SEQ ID NO: 200)<br>MBS |
|             UU (SEQ ID NO: 215)<br>            G C<br>MBS 5'- CGCCAAUAUUUA CGUGCUGCUA -3'<br>miR-16 3'- GCGGUUAUAAAU--GCACGACGAU -5'<br>(SEQ ID NO: 140) | |
| S-TuD-miR16-10mut | MBS (SEQ ID NO: 201)<br>5'- GACGGCGCUAGGAUCAUC AACC- CAAUAUUUAUGUGCU UACAA GUAUUCUGGU -3'<br>          GC CC<br>3'- CUGCCGCGAUCCUAGUAG CG CG CAUAAGACCA -5'<br>          AACAU UCGUGUAUUUAUAAC -CCAA<br>(SEQ ID NO: 202)<br>MBS |
| (SEQ ID NO: 216)<br>MBS 5'- CGCCAAUAUUUAUGUCCUGCUA -3'<br>miR-16 3'- GCGGUUAUAAAUGCACGACGAU -5'<br>(SEQ ID NO: 140) | |

FIG. 34

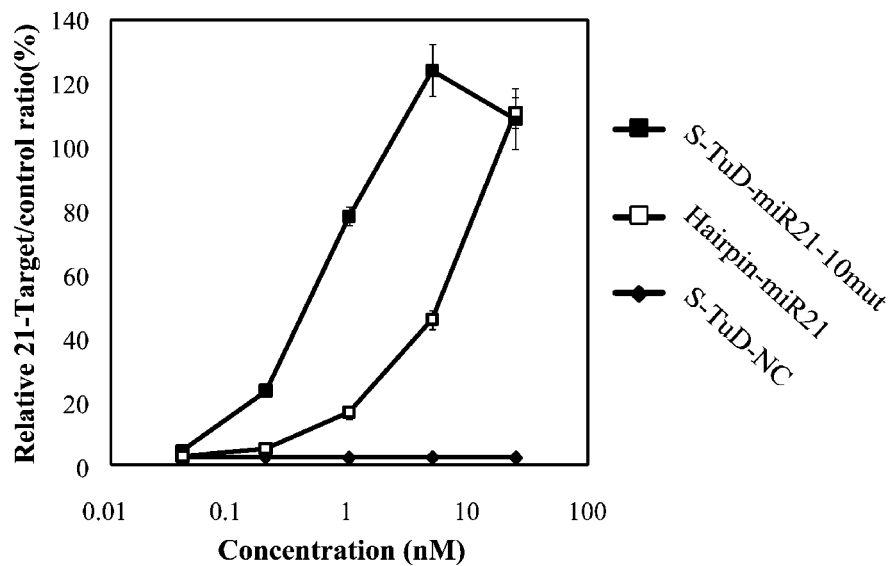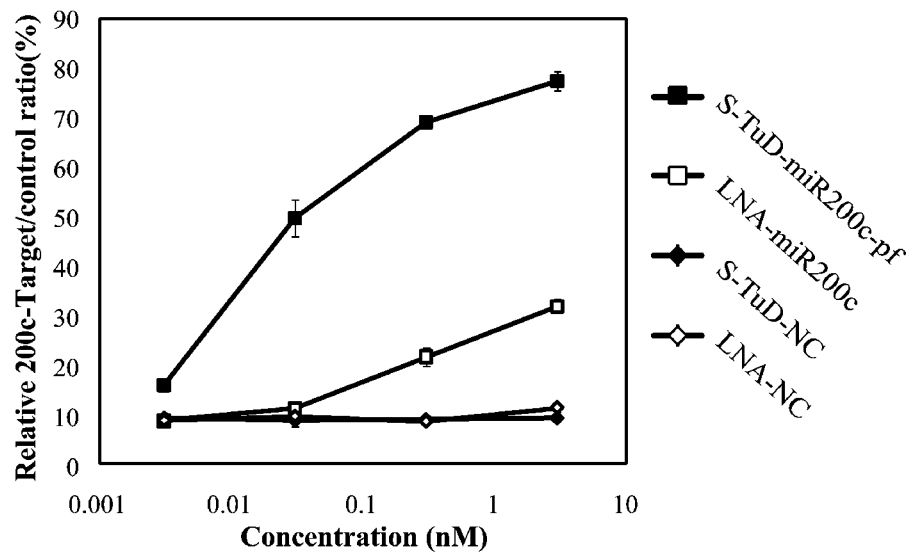
FIG. 35

METHOD FOR INHIBITING FUNCTION OF MICRO-RNA

PRIORITY

This application is a continuation-in-part of PCT/JP2009/067251 (WO2010/047216) filed Oct. 2, 2009, which claims priority from Japanese Patent Application No. 2009-011877, filed Jan. 22, 2009, and Japanese Patent Application No. 2008-273562, filed Oct. 23, 2008. All of these applications are incorporated herein by reference.

FIELD OF THE INVENTION

The present invention relates to methods for efficiently inhibiting miRNA function, and nucleic acids for use in such methods.

BACKGROUND OF THE INVENTION

Micro-RNA (miRNA) is an endogenously expressed small (approximately 20- to 24-nucleotide) regulatory noncoding RNA, and regulates expression of various target genes at the post-transcriptional level as a component of RNA-induced silencing complex (RISC). When a miRNA is completely complementary to its target sequence in an mRNA, the miRNA induces cleavage of the mRNA, and causes rapid decrease in the mRNA level. However, most mammalian miRNAs have only a limited level of complementarity with target sequences located in the 3'-untranslated region (3'-UTR), and cause either translational repression or rapid deadenylation of target mRNAs in cytoplasmic processing bodies (P bodies). One-third or more of human coding genes are predicted to be targets of miRNAs (Bartel, D. P. (2004) Cell, 116, 281-297; Lewis, B. P. et al. (2005) Cell, 120, 15-20; Ambros, V. et al. (2003) Rna, 9, 277-279), and there is continuing evidence that shows miRNAs play important roles in differentiation, development, tumorigenesis, and cellular defense against infection (Li, Q. J. et al. (2007) Cell, 129, 147-161; Lu, J. et al. (2005) Nature, 435, 834-838; Lecellier, C. H. et al. (2005) Science, 308, 557-560).

Techniques to specifically inhibit the activity of miRNA molecules are considered indispensable for their global functional analysis. Several methods for inhibiting miRNA function already exist, and for example, chemically modified single-stranded oligonucleotides such as 2'-O-methyl (2'-OMe) RNA (Hutvagner, G et al. (2004) PLoS Biol, 2, E98; Meister, G et al. (2004) Rna, 10, 544-550), locked nucleic acid (LNA), and "antagomirs" (Orom, U. A. et al. (2006) Gene, 372, 137-141; Krutzfeldt, J. et al. (2005) Nature, 438, 685-689) are used. These reagents are chemically synthesized to have complementarity towards mature miRNAs. They are resistant to cellular nucleases, and may function as substrates not cleaved by RISC. Since they are designed to be introduced into cells by transfection, the inhibitory activity is inevitably transient.

Recently, DNA vectors that express "microRNA sponges" which are competitive inhibitors of miRNAs were reported (Ebert, M. S. et al. (2007) Nat Methods, 4, 721-726). Although transient expression of microRNA sponge vectors efficiently inhibits miRNA function, the inhibitory effects are not maintained for more than one month even if transfection is carried out using DNA-based vectors. Therefore, it is desirable to establish methods for inhibiting miRNAs for a longer period of time.

SUMMARY OF THE INVENTION

The present invention relates to miRNA inhibitors for efficiently inhibiting miRNAs, vectors for expressing the inhibitors in cells, methods for constructing the vectors, methods for inhibiting miRNAs using the inhibitors or vectors, and such.

To achieve more efficient and long-term suppression of miRNAs, the present inventors newly designed RNAs that can inhibit miRNAs, and evaluated their miRNA-inhibiting activity. As a result, it was discovered that RNAs in which miRNA binding sequences (MBSs) are linked at one end to the two strands of a double-stranded RNA show a strong miRNA-inhibiting activity (FIGS. 1 and 2). In particular, RNAs that comprise two double-stranded RNA portions, in which MBSs are linked to each strand of the double strands such that the MBSs are placed between the two double strands (FIG. 2, #12 to #16) showed a very strong miRNA-inhibiting activity. The present inventors converted one end of the RNA structures comprising double-stranded portions into a closed structure (for example, a loop structure) to construct these miRNA-inhibiting RNAs as linear single-stranded RNAs, and thus allowed the RNAs to be expressed from a single transcription unit. Furthermore, the present inventors assembled MBSs to one side of a double-stranded structure, and make the opposite side and the double-stranded structure portion constant regions. Thus, the present inventors produced an extremely convenient system to construct expression vectors for RNAs that show specific inhibitory activity towards the miRNAs of interest, by inserting a cassette comprising an MBS of interest into an expression unit comprising these constant regions. In cells transfected with these expression vectors, target miRNAs can be strongly inhibited. In addition, vectors can be easily constructed for miRNAs of interest.

In a preferred embodiment, a miRNA inhibitor of the present invention may also be a synthetic RNA, which is composed of two RNA strands; and the RNAs are preferably fully modified such as 2'-O-Methylated RNAs. Each of the strands may include a miRNA binding site (MBS) and after hybridization of the pair strands, the resultant RNA molecule forms secondary structure with two stems, which resembles the corresponding the miRNA-inhibitor composed of a single-stranded RNA molecule with a stem-loop structure. By analyzing the inhibitory activities against miR-21 and miR-200c, the inventors have extracted and present basic guidelines to design synthetic niRNA inhibitors that give optimum inhibitory effects after transfection into human cell lines.

Specifically, the present invention relates to miRNA inhibitors for efficiently inhibiting miRNAs, vectors for expressing the inhibitors in cells, methods for constructing the vectors, methods for inhibiting miRNAs using the inhibitors or vectors, and such. More specifically, the present invention relates to the following:

[1] An miRNA-inhibiting complex comprising an RNA or analog thereof, which comprises a double-stranded structure, and wherein at least one miRNA-binding sequence-comprising strand is bound to two strands on at least one end of the double-stranded structure.

[2] The complex of [1], which comprises a second multiple-stranded structure, wherein strands comprising an miRNA-binding sequence are each bound to one of the two strands on said one end of said double-stranded structure, and wherein the other ends of the strands are each bound to one of two strands of the second multiple-stranded structure, so that the strands are placed between the double-stranded structure and the multiple-stranded structure.

[3] The complex of [2], wherein the multiple strand is a double or quadruple strand.

[4] The complex of any one of [1] to [3], wherein the two strands on said one end are linked together on the side of said one end.
[5] The complex of [4], which is composed of a single-stranded linear RNA or analog thereof.
[6] The complex any one of [1] to [3], which is composed of two single-stranded linear RNAs or analogs thereof.
[7] The complex of any one of [1] to [6], which comprises two to five miRNA-binding sequences.
[8] The complex of [7], which comprises two miRNA-binding sequences.
[9] The complex any one of [1] to [8], which comprises a structure shown in FIG. 2(C), wherein I and II of the structure is double-stranded, and wherein each of a and b of the structure comprises an miRNA-binding sequence.
[10] The complex of [5], which comprises a structure shown in FIG. 2(D), wherein I of the structure is double-stranded and the end of each strand is present on one side of I, and wherein II of the structure is a hairpin, and each of a and b of the structure comprises an miRNA-binding sequence.
[11] An RNA or analog thereof which composes the complex of any one of [1] to [10].
[12] A nucleic acid which encodes the RNA of [11].
[13] The nucleic acid of [12], which is bound downstream of a promoter.
[14] The nucleic acid of [13], wherein the promoter is a polymerase III promoter.
[15] The nucleic acid of [13] or [14], which is carried by a retroviral vector.
[16] A method of producing the nucleic acid of [13], which comprises the step of inserting a nucleic acid encoding at least one miRNA-binding sequence between a pair of nucleic acids that encode downstream of a promoter a pair of complementary sequences that form at least one double-stranded structure.
[17] The method of [16], wherein the nucleic acid encoding at least one miRNA-binding sequence comprises at least two miRNA-binding sequences and a stem-forming sequence between said sequences.
[18] A kit for preparing the nucleic acid of [13], wherein the kit comprises the nucleic acids of (a) and (b) below:
(a) a nucleic acid comprising downstream of a promoter a pair of complementary sequences that form at least one double-stranded structure, and a site for insertion of a nucleic acid between the pair of complementary sequences;
(b) a nucleic acid encoding at least one miRNA-binding sequence.
[19] The kit of [18], wherein the nucleic acid encoding at least one miRNA-binding sequence comprises at least two miRNA-binding sequences and a stem-forming sequence between said sequences.

Furthermore, the present invention relates to the following:
[1] An miRNA-inhibiting complex comprising an RNA or analog thereof, which comprises a double-stranded structure, and wherein at least one miRNA-binding sequence-comprising strand is bound to two strands on at least one end of the double-stranded structure.
[2] The complex of [1], which comprises a second double-stranded structure, wherein strands comprising an miRNA-binding sequence are each bound to one of the two strands on said one end of said double-stranded structure, and wherein the other ends of the strands are each bound to one of two strands of the second double-stranded structure, so that the strands are placed between the two double-stranded structures.
[3] The complex of [1] or [2], wherein the two strands on said one end are linked together on the side of said one end.
[4] The complex of [3], which is composed of a single-stranded linear RNA or analog thereof
[5] The complex of any one of [1] to [4], which comprises two to five miRNA-binding sequences.
[6] The complex of [5], which comprises two miRNA-binding sequences.
[7] An RNA or analog thereof which composes the complex of any one of [1] to [6].
[8] A nucleic acid which encodes the RNA of [7].
[9] The nucleic acid of [8], which is bound downstream of a promoter.
[10] The nucleic acid of [9], wherein the promoter is a polymerase III promoter.
[11] The nucleic acid of [9] or [10], which is carried by a retroviral vector.
[12] A method of producing the nucleic acid of [9], which comprises the step of inserting a nucleic acid encoding at least one miRNA-binding sequence between a pair of nucleic acids that encode downstream of a promoter a pair of complementary sequences that form at least one double-stranded structure.
[13] The method of [12], wherein the nucleic acid encoding at least one miRNA-binding sequence comprises at least two miRNA-binding sequences and a stem loop-forming sequence between said sequences.
[14] A kit for preparing the nucleic acid of [9], wherein the kit comprises the nucleic acids of (a) and (b) below:
(a) a nucleic acid comprising downstream of a promoter a pair of complementary sequences that form at least one double-stranded structure, and a site for insertion of a nucleic acid between the pair of complementary sequences;
(b) a nucleic acid encoding at least one miRNA-binding sequence.
[15] The kit of [14], wherein the nucleic acid encoding at least one miRNA-binding sequence comprises at least two miRNA-binding sequences and a stem loop-forming sequence between said sequences.

It is intended that for each of the items described above, inventions arbitrarily combined from two or more of the inventions described in items that recite the same antecedent item are also included in the inventions described in the antecedent item that they recite. Furthermore, it is intended that any elements of the inventions described herein and any combinations thereof are also included in the present invention. In addition, it is intended that inventions that exclude any elements described herein or any combinations thereof from the above inventions are also included in the present invention. Herein, for example, when a specific embodiment is described as a "preferable" embodiment, the specification discloses not only this embodiment, but also inventions that exclude the embodiment from antecedent inventions comprising the embodiment disclosed in the specification.

The present invention provides miRNA inhibitors that can efficiently and specifically inhibit miRNA function. The miRNA inhibitors of the present invention can stably inhibit miRNAs for a long time by, for example, integrating their expression units into retroviral vectors. This enables in vivo assays using, for example, knockdown mice. Furthermore, since Cre-loxP regulated U6 promoter systems have already been established, they may be utilized to perform miRNA knockdown in a time- and tissue-specific manner. As exemplified in FIG. 6, since an expression cassette for a miRNA-inhibiting RNA of the present invention can be readily constructed, this can be utilized to construct an RNA library for global analysis of miRNAs. Thus, the present invention provides tools that are very useful for miRNA research. For example, the present invention can be used to identify candidate target mRNAs by comprehensively investigating mRNAs expressed in cultured cells by expressing or not expressing specific miRNA-inhibiting RNAs. Furthermore, a significant proportion of genes in a living body are predicted to be targets of miRNAs, and it has been suggested that miRNAs play important roles in various aspects including differentiation, development, tumorigenesis, and cellular defense against infections. The methods of the present invention are useful for regulating functions of miRNAs related to gene therapy against tumors and infections, elucidation of gene regulatory mechanisms, and such.

BRIEF DESCRIPTION OF THE DRAWINGS

FIG. 2 shows comparison of the inhibitory effects of a series of decoy RNAs having various stem structures. (A) The structures of decoy RNAs #2 and #10 to #16. The black thick curved arrows represent MBSs. I, II, III, and IV show the stems present in the decoy RNAs. (B) The effect of lentiviral vectors expressing these decoys was determined using the same reporter cell system as mentioned in the description of FIG. 1B. The expression levels were normalized as with FIG. 1B. The length of each of the stem sequences (I, II, III, and IV) of the decoy RNAs are shown. (C) A form of a unit that constitutes decoy RNAs of the present invention. I represents a first double-stranded structure, and II represents a second double-stranded structure. a and b each includes at least one MBS. The end of the second double-stranded structure (the right end in the figure) can form a loop or not. When a loop is formed, the decoy RNA becomes single-stranded. Multiple MBSs may be included in a and b. Alternatively, a and b may not be completely single-stranded but partially form a double-stranded structure. Multiple units may be linked in tandem (for example, #15 and #16 of panel A). (D) The structure in which a loop is formed at the end of the second double-stranded structure in the unit shown in panel (C). There is no particular limitation on the number of nucleotides included in the loop, and it may be zero to several, for example, one, two, three, four, five, six, or seven nucleotides. The vertical lines of the double-stranded portions in panels (A), (C), and (D) represent formation of double-stranded structures, and are not meant to limit the number of nucleotides to the number of vertical lines.

FIG. 3 shows that the MBS sequences of the prototype decoy RNAs significantly affect the inhibitory effect. Relative GFP expression was determined as mentioned in the description FIG. 1B.

FIG. 5 shows the effect of bulges in the MBS sequences and the linkers that connect the MBSs and the stems. Relative GFP expression was determined as mentioned in the description of FIG. 1B. The black thick curved arrows represent MBSs.

FIG. 15 shows the structures of retroviral vectors used for construction of highly sensitive assay systems for miR140-3p or miR-140-5p. (A) The provirus structure of the reporter MLV-based retroviral vector pMXs-GIN-miR140-3pT. This has a 21-bp insertion that is completely complementary to mature miR-140-3p, immediately downstream of the GFP gene. U3, R, and U5 indicate the respective MoMLV long terminal repeat-derived sequences. ψ represents a packaging signal of the retroviral vector. (B) The provirus structure of the reporter MLV-based retroviral vector pMXs-GIN-miR140-5pT. (C) The provirus structure of the MoMLV-based miR140-5p/140-3p expression vector pSSCH-miR140-5p/140-3p. The pri-miR140-5p/140-3p sequence was inserted into the ΔU3 sequence so that it is transcribed from the internal CMV promoter. ΔU3 represents a U3 sequence from which major enhancer sequences have been removed. (D) The structure of an HIV-based self-inactivating decoy RNA expression vector. ΔU3 represents a U3 sequence from which major enhancer sequences have been removed. ψ represents the lentiviral R sequence. U5 represents the lentiviral U5 sequence. ψ represents a lentiviral packaging signal.

FACS analysis of the GFP expression level (intrinsic fluorescence) of HeLaS3 cells (A), FACS analysis of the GFP expression level of HeLaS3 cells carrying the miR140-3p reporter alone (B), and FACS analysis of the GFP expression level of HeLaS3 cells carrying both the miR140-3p reporter and miR140-5p/140-3p expression vector (C). FACS analysis of the GFP expression level eight days after introducing either TuD-miR140-3p-4ntin (D) or TuD-miR140-5p-4ntin (E) into miR140-3p reporter cells. The thick solid line and dotted line represent, respectively, the GFP expression profile of HeLaS3 cells carrying the miR140-3p reporter alone, and the GFP expression profile of HeLaS3 cells carrying both the miR140-3p reporter and miR140-5p/140-3p expression vector.

FIG. 17 shows the structures of luciferase expression vectors. (A) The structure of the firefly luciferase expression plasmid vector pTK4.12C.P-. (B) The structure of the Renilla luciferase reporter pGL4.74 without an insert. (C) The structure of the Renilla luciferase reporter pGL4.74-miR21T having a 22-bp insert completely complementary to mature miR-21 immediately downstream of the Renilla luciferase gene. (D) The structure of the Renilla luciferase reporter pGL4.74-miR16T having a 22-bp insert completely complementary to mature miR-16 immediately downstream of the Renilla luciferase gene.

FIG. 18 shows the structures and sequences of the miRNA-inhibiting RNAs of the present invention. MBS represents a miRNA binding site that is completely or partially complementary to the corresponding miRNA.

Figure 8:
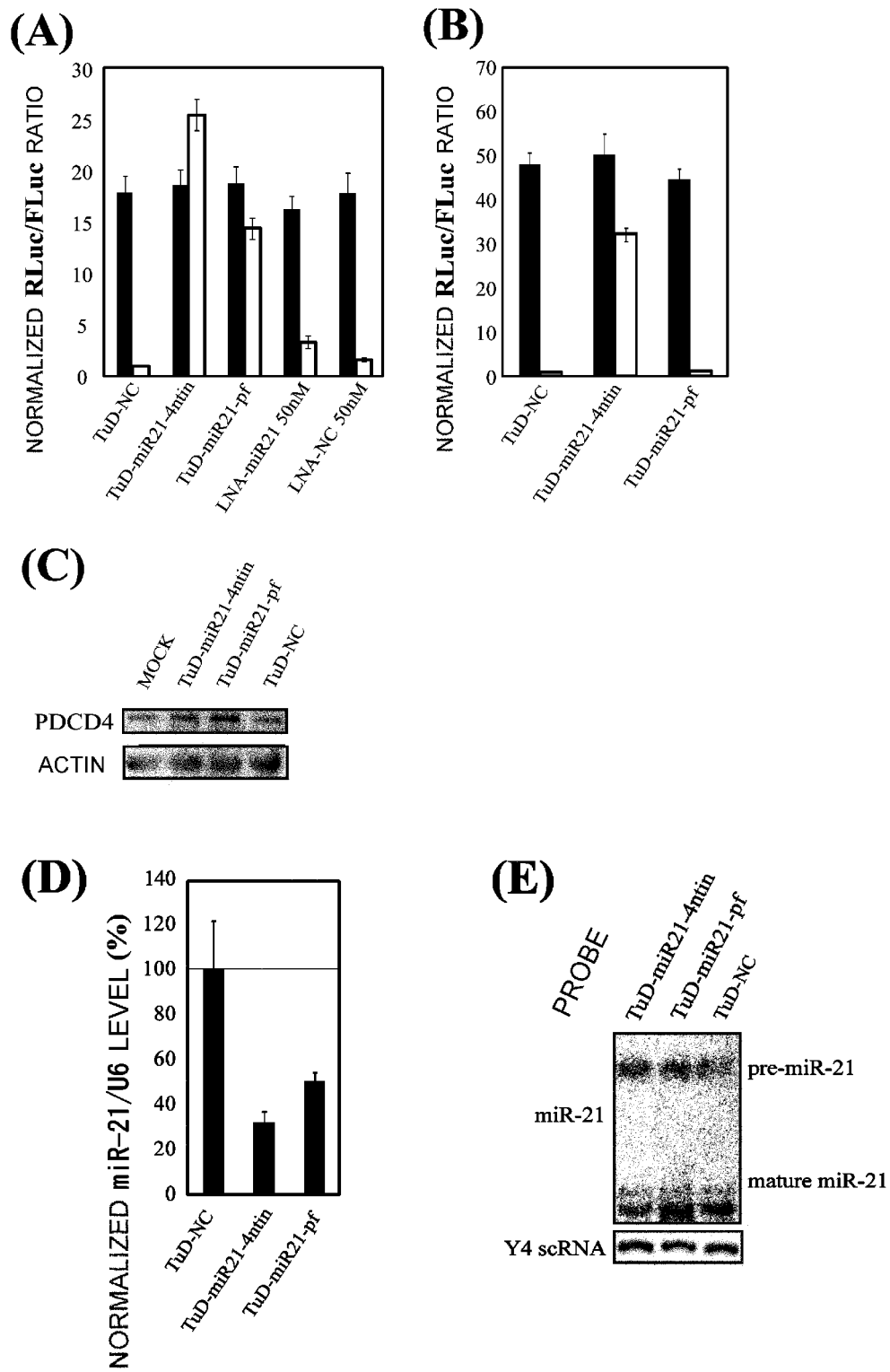
FIG. 8 shows the inhibitory effect of miRNA-inhibiting complexes against endogenous miR21 activity. An miRNA-inhibiting RNA expression plasmid vector or LNA/DNA antisense oligonucleotide was transiently transfected into PA-1 (A) or HCT-116 (B) cells, together with the Renilla luciferase miR-21 reporter (white bar) or non-targeted control Renilla luciferase reporter (black bar), in addition to a firefly luciferase reporter as a transfection control. After dual luciferase assay, the expression levels were normalized against those of PA-1 or HCT-116 cells transfected with the TuD-NC vector, and presented as mean±SEM. (C) The effect of transiently transfected miRNA-inhibiting RNA expression plasmid vectors on expression of the endogenous PDCD4 protein which is the target of miR21. A miRNA-inhibiting RNA expression plasmid vector was transfected into PA-1 cells, and total proteins were prepared 72 hours after transfection. PDCD4 (top) and β-actin loading control (bottom) were detected by Western blotting. (D) miR21 expression levels were measured by realtime RT-PCR in cells subjected to the same treatment as in (B). The miR21 expression levels were normalized against the miR21 expression level of HCT-116 cells transfected with the TuD-NC vector, and presented as mean±SEM (n=3). U6 snRNA was used as the internal control. (E) pre-miR21 and mature miR21 expression levels were measured by Northern blotting in cells subjected to the same treatment as in (B). Y4 scRNA is shown as a loading control.
Figure 19:
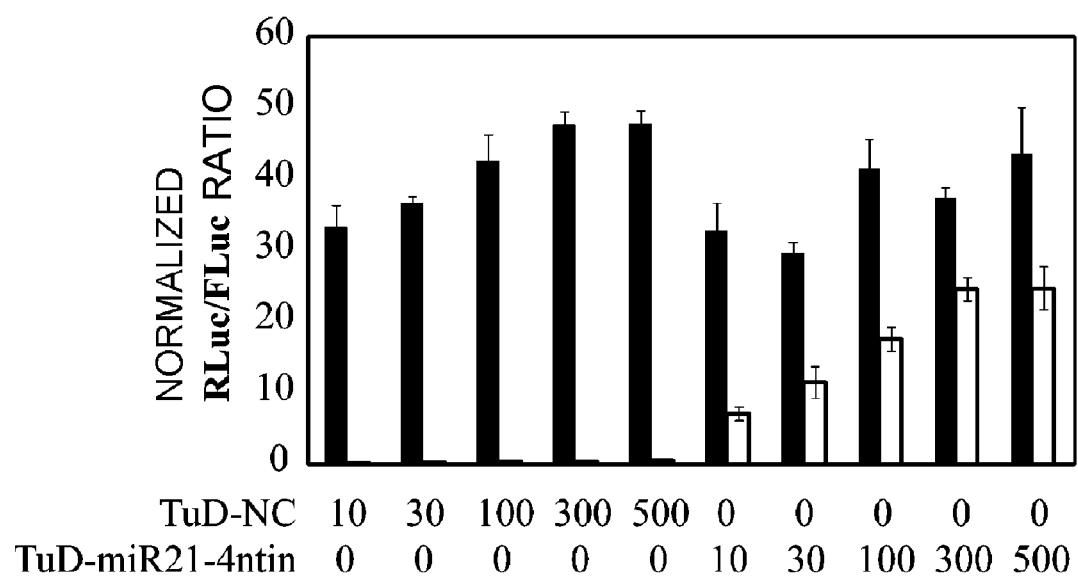

FIG. 19 shows dependency of the miR-21-inhibiting effect on the amount of the TuD-miR-21-4ntin expression vector. HCT-116 cells were transfected with various amounts of the TuD-NC and TuD-miR-21-4ntin expression plasmids, and otherwise using the same conditions as in FIG. 8 (B). The expression levels were normalized against the value for HCT-116 cells transfected with the TuD-NC vector, and presented as mean±SEM (n=3).

Figure 20:
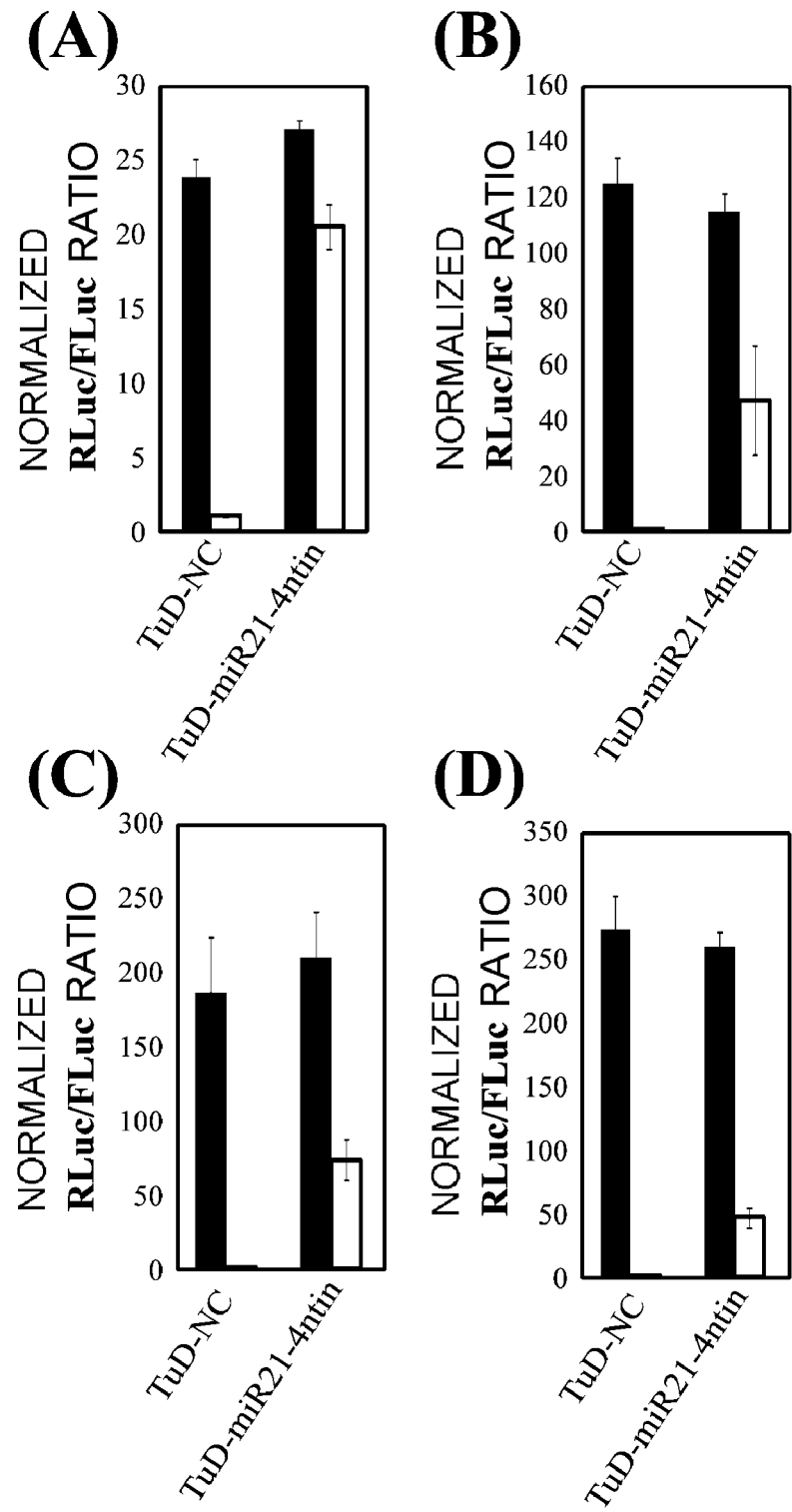

FIG. 20 shows the inhibitory effect of miRNA-inhibiting complexes against endogenous miR21 activity. The miRNA-inhibiting RNA expression plasmid vector or LNA/DNA antisense oligonucleotide was transiently transfected into SW480 cells (A), HT29 cells (B), TIG-3/E/TERT cells (C), or 3Y1 cells (D), together with Renilla luciferase miR-21 reporter (white bar) or non-targeted control Renilla luciferase reporter (black bar), in addition to a firefly luciferase reporter as a transfection control. After dual luciferase assay, the expression levels were normalized against those of SW480 cells, HT29 cells, TIG-3/E/TERT cells, or 3Y1 cells transfected with the TuD-NC vectors, and presented as mean±SEM (n=3).

Figure 21:
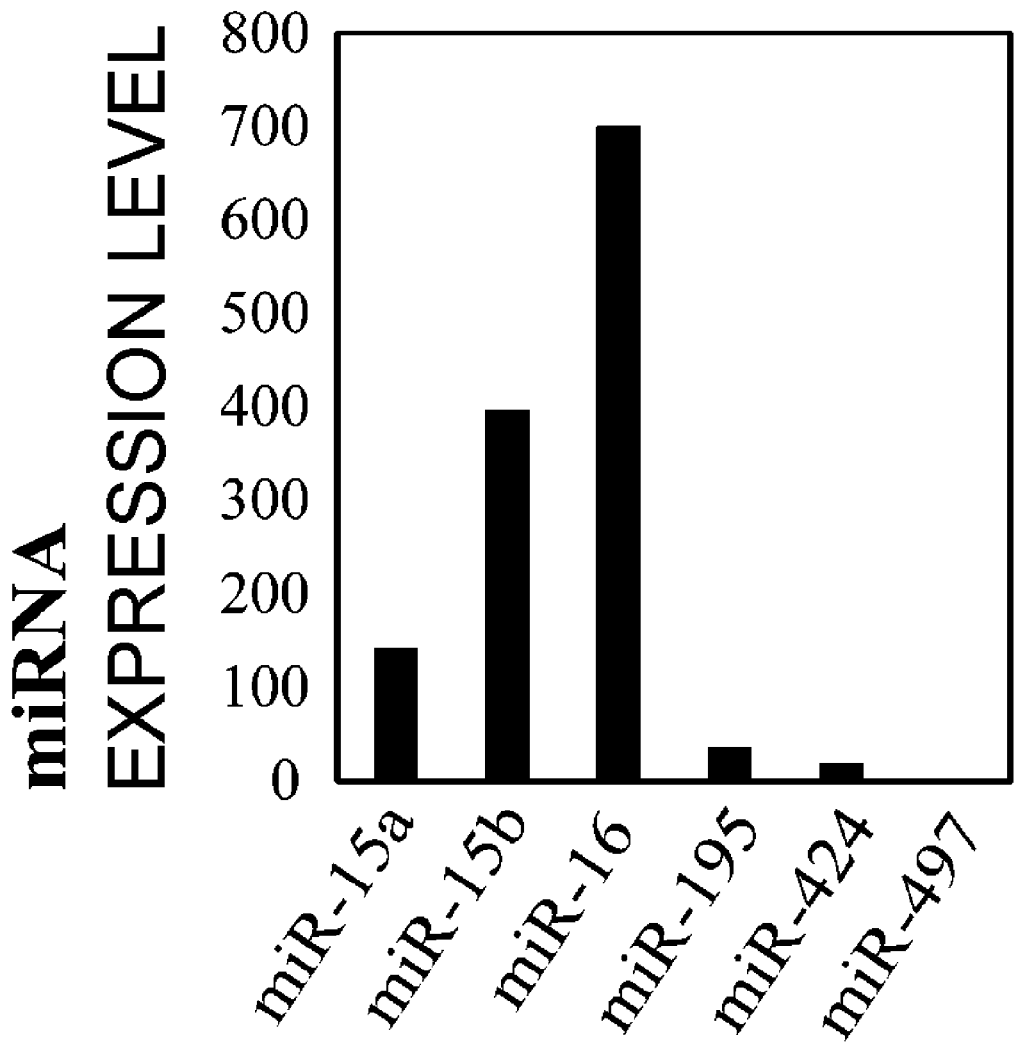

FIG. 21 shows the expression levels of the miR-15a/15b/16/195/424/497 family in HCT-116 cells. The expression levels were analyzed by an Agilent miRNA microarray.

Figure 22:
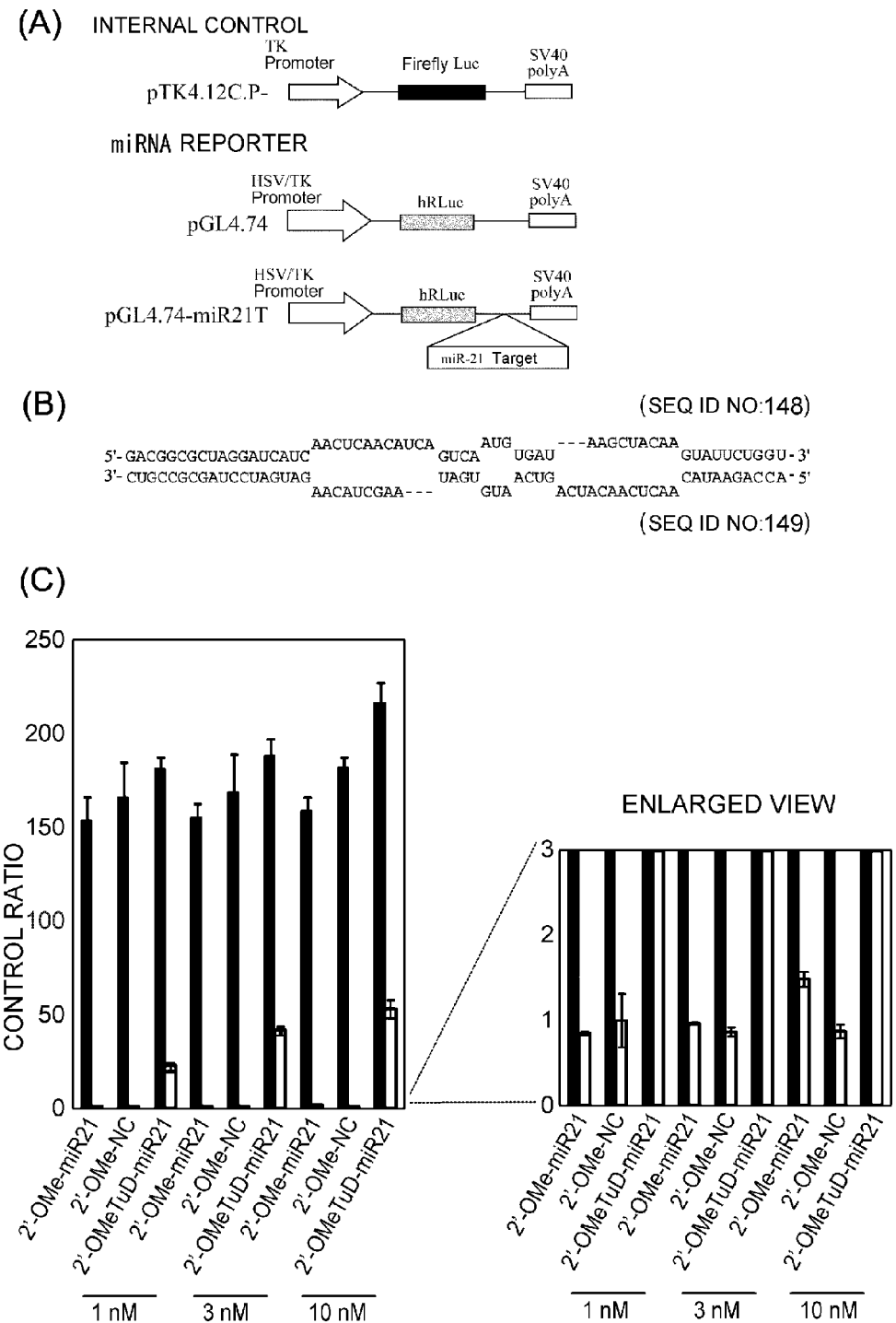

FIG. 22 shows miRNA-inhibiting RNAs of the present invention produced from 2'-O-methyl synthetic oligonucleotides, and the effect of the RNAs. (A) The reporter plasmids for dual luciferase assay. All of the experiments of Examples 7 to 9 were carried out using HCT-116 cells. (B) The structure of a miRNA-inhibiting RNA of the present invention produced from 2'-O-methyl synthetic oligonucleotides. All of the nucleotides used were two synthetic oligonucleotides that are 2'-O-methylated and annealed. (C) The miRNA-inhibiting effect of synthetic RNAs produced from 2'-O-methyl synthetic oligonucleotides is indicated. The miRNA-inhibiting effect of the inhibitory RNAs was measured by varying the concentration, and compared to that of conventional 2'-O-methyl synthetic oligonucleotides.

Figure 23:
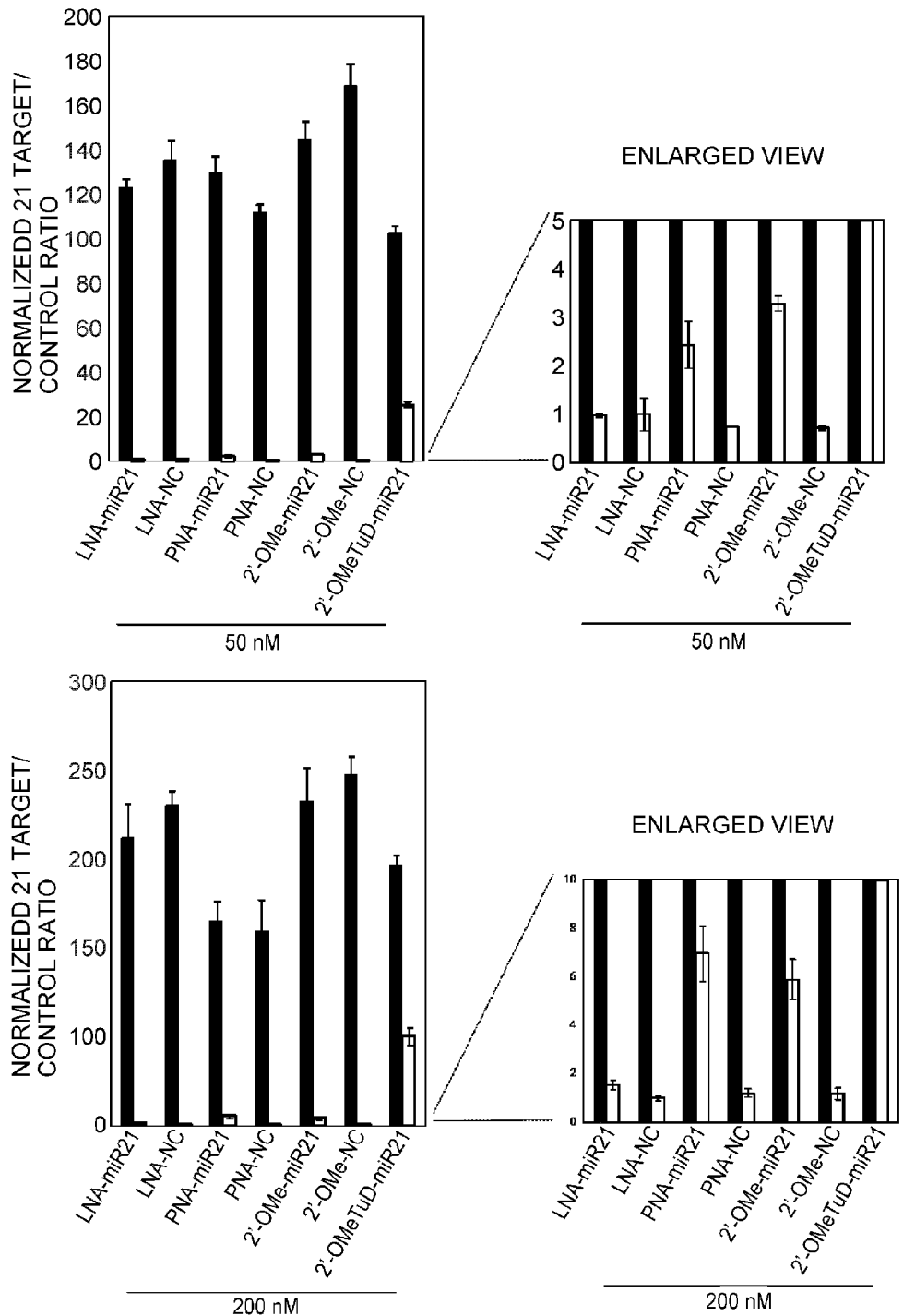

FIG. 23 shows the results of comparing the miRNA-inhibiting effect of a miRNA-inhibiting RNA of the present invention to that of conventional LNA, PNA, and 2'-O-methylated oligos.

Figure 24:
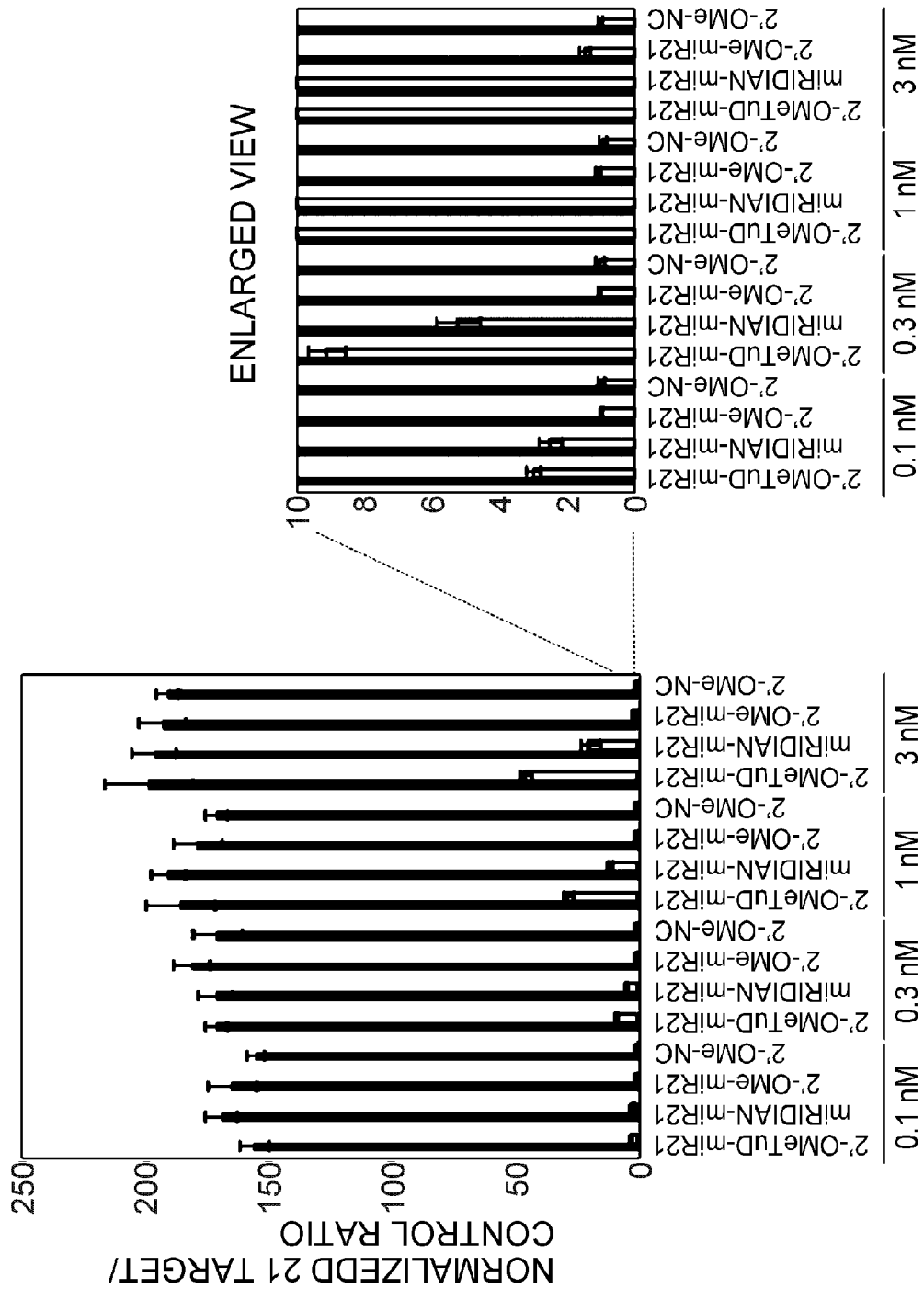

FIG. 24 shows the results of comparing the miRNA-inhibiting effect of a miRNA-inhibiting RNA of the present invention to that of miRIDIAN Inhibitor and others.

FIG. 25 shows transcription of the miRNA-inhibiting RNAs of the present invention utilizing guanine quadruplexes (G-quadruplexes), and their effects. (A) The parallel quadruplex structure of G-quadruplex-Loop 111, and parallel and antiparallel quadruplex structures of the G-quadruplex-Loop 333. (B) Schematic diagrams of the structures of TuD-miR21-4ntin, TuD-miR21-4ntin-GqL111, and TuD-miR21-4ntin-GqL333. (C) The miRNA-inhibiting activity of each of the RNAs.

FIG. 26 shows the effect of the structures of miRNA-inhibiting RNAs. (A) Schematic diagrams of the structures of TuD-miR21-4ntin, TuD-miR21-4ntin-1MBS-1, and TuD-miR21-4ntin-1MBS-2. The dashed arrow indicates reverse MBS sequence in 1MBS-1, and TuD-NC (control sequence) in 1MBS-2. (B) The miRNA-inhibiting activity of each of the RNAs.

Figure 27:
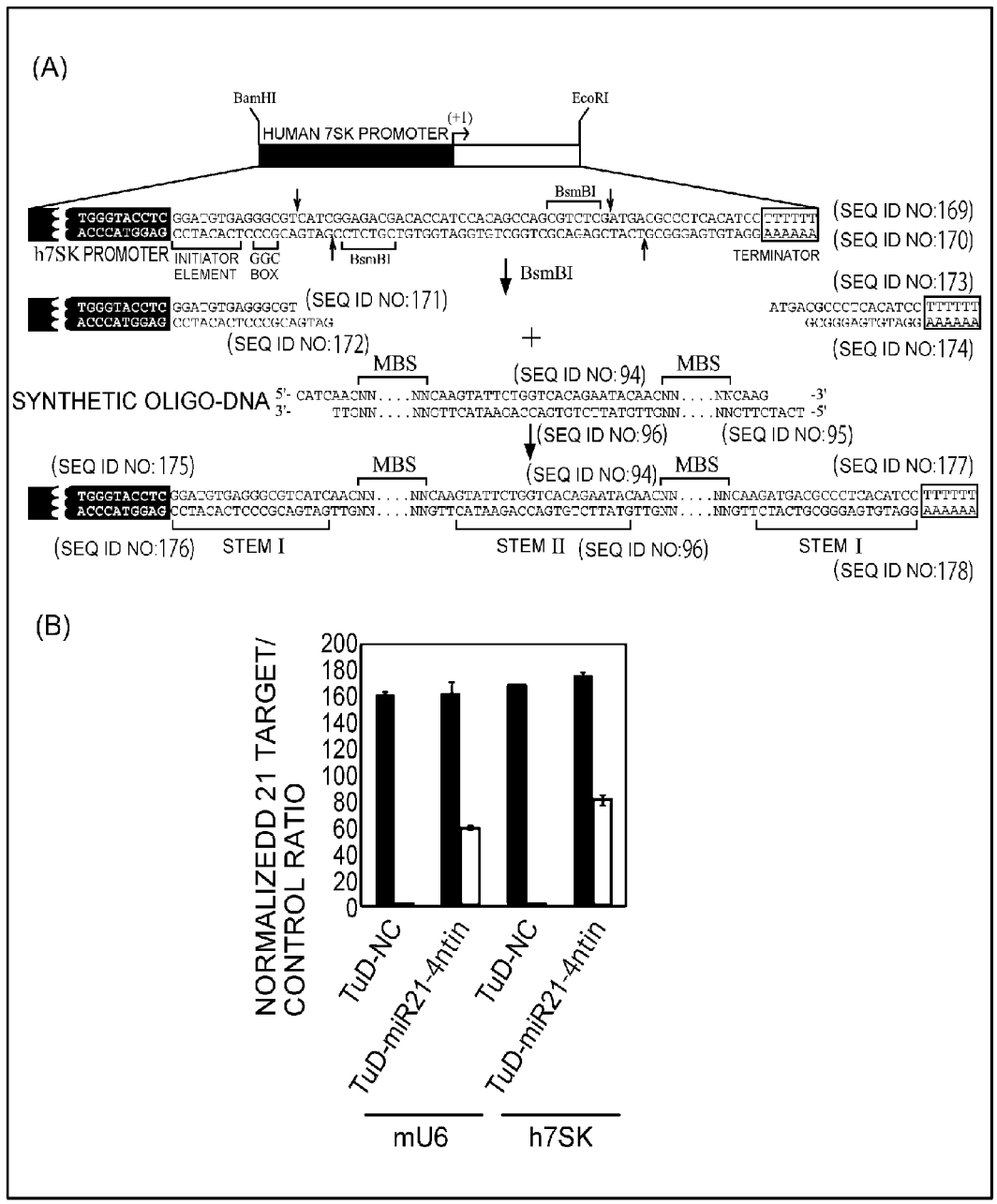

FIG. 27 shows transcription of the miRNA-inhibiting RNAs of the present invention from the human 7SK promoter, and the effects of the RNAs. (A) The structure of an expression cassette for transcription of a miRNA-inhibiting RNA of the present invention from the human 7SK promoter. Transcription of the human 7SK promoter is enhanced by the sequence immediately downstream of the transcription start site of 7SK RNA (specifically the first to eighth nucleotides). Therefore, the first to thirteenth nucleotides of 7SK RNA were integrated into the stem portion of the inhibitory RNAs of the present invention. (B) The miR-21-inhibiting effect in HCT-116 cells. The measurements were performed by the dual luciferase assay described in FIG. 22(A).

Figure 28:
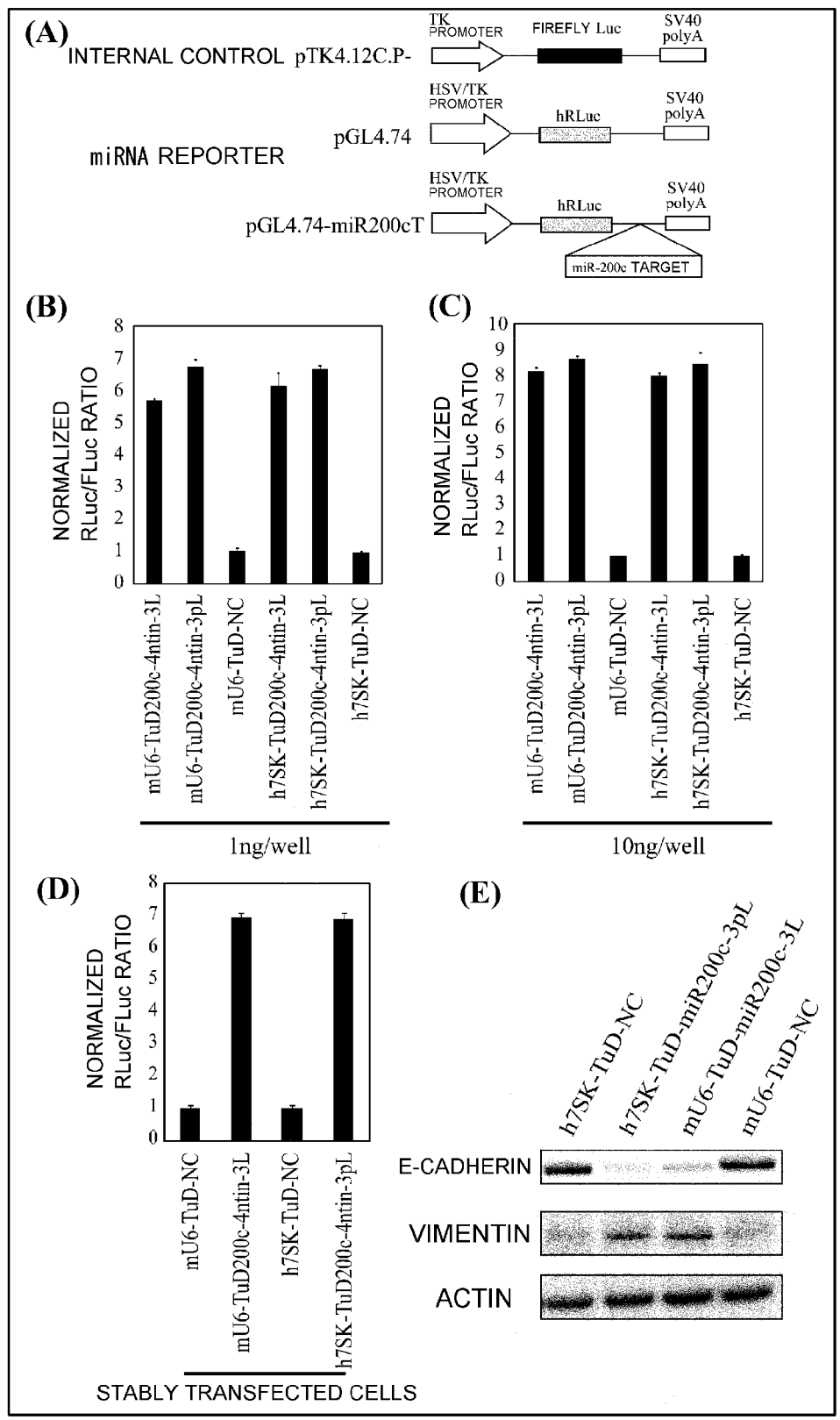

FIG. 28 shows the miR200-inhibiting effect of the miRNA-inhibiting RNAs of the present invention. (A to D) Expression plasmids of the miRNA-inhibiting RNAs of the present invention that target miR200 were constructed. The effect of the miRNA-inhibiting RNAs expressed from two types of promoters using a luciferase reporter assay system is shown. (E) Epithelial/mesenchymal transformation by TuD-miR200c-4ntin. miRNA-inhibiting RNA-expressing lentiviral vectors were introduced into HCT-116 cells to produce cell populations that stably express miRNA-inhibiting RNAs. Total proteins were prepared 15 days after transfection. E-cadherin (top) and vimentin (middle) which are gene markers of epithelial cells and mesenchymal cells, respectively, and the β-actin loading control (bottom) were measured by Western blotting.

Figure 29:
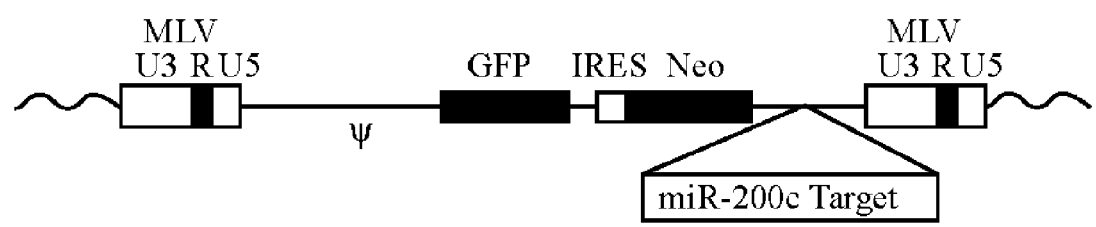

FIG. 29 shows structures of the retrovirus vectors used for the construction of the sensitive assay system for miR-200c. Proviral structure of the reporter MLV-based retrovirus vector, pMXs-GIN-miR200cT. Immediately downstream of the Neomycin resistance gene, it has an insert of 23 bp which is fully complementary to the mature miR-200c molecule. U3, R and U5 indicate these corresponding sequences from the MoMLV long terminal repeat; ψ, packaging signal of the retrovirus vector.

FIG. 30 shows structures of luciferase expression vectors. (A) Structure of the firefly luciferase expression plasmid vector, pTK4.12. (B) Structure of the *Renilla* luciferase reporter without insertion; pGL4.74. (C) Structure of the *Renilla* luciferase reporter with insertion of 22 bp, which is fully complementary to the mature miR-21 just downstream of the *Renilla* luciferase gene; pGL4.74-miR21 T. (D) Structure of the *Renilla* luciferase reporter with insertion of 23 bp, which is fully complementary to the mature miR-200c just downstream of the *Renilla* luciferase gene; pGL4.74-miR200cT. (E) Structure of the *Renilla* luciferase reporter with insertion of 22 bp, which is fully complementary to the mature miR-16 just downstream of the *Renilla* luciferase gene; pGL4.74-miR16T.

FIG. 31 shows the schematic structures of the miRNA-inhibiting RNAs of the present invention consisting of one RNA molecule with a stem-loop (A) and two RNA molecules (B). (C) Inhibitory effects of S-TuD-miR21-4ntin on endogenous miR-21 activity. Synthetic miRNA-inhibiting RNAs shown in panel (B) (consisting of 2'-O-Methylated RNAs) or 2'-O-Methylated RNA oligonucleotides-based antisense were transfected into HCT-116 cells together with the *Renilla* luciferase miR-21 reporter (miR-21-RL) (open bars) or the untargeted control *Renilla* luciferase reporter (UT-RL) (black bars) as well as the Firefly luciferase reporter (FL) as a transfection control. After performing a dual luciferase assay, the expression levels were normalized to the ratio of the activity of miR-21-RL to that of FL in S-TuD-NC (a negative control RNA consisting of the structure shown in panel (B) with irrelevant MBS sequences) transfected HCT-116 cells and were represented by the mean±SEM (n=3).

Figure 32:
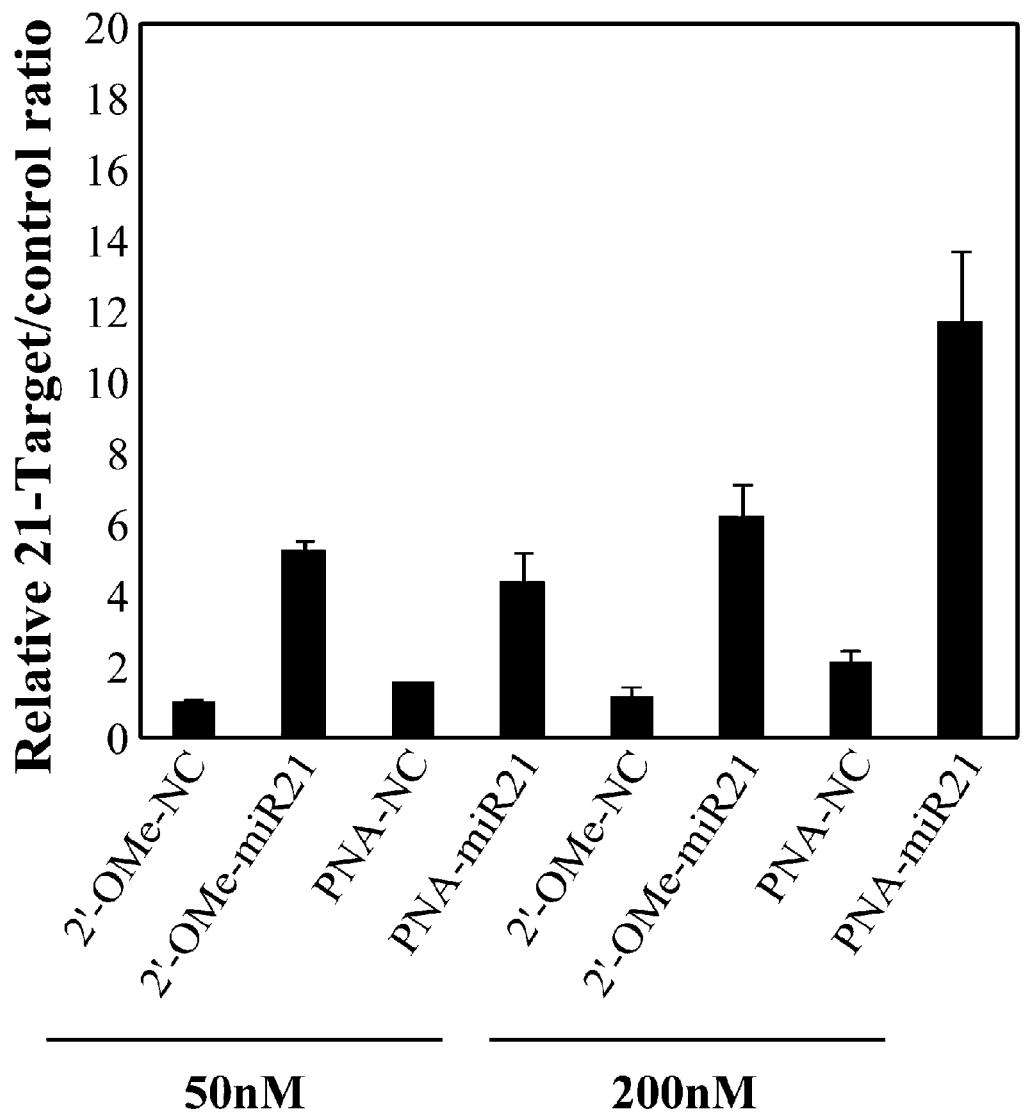

FIG. 32 shows inhibitory effects of 2'-O-Methylated RNA AMOs and PNA AMOs. 2'-O-Methylated RNA oligonucleotides-based antisense or PNA oligonucleotides-based antisense were transfected into HCT-116 cells together with the *Renilla* luciferase miR-21 reporter (miR-21-RL) or the untargeted control *Renilla* luciferase reporter (UT-RL) as well as the Firefly luciferase reporter (FL) as a transfection control. After performing a dual luciferase assay, the ratio of miR-21-RL/FL to UT-RL/FL are represented by the mean±SEM (n=3) as the expression levels. This expression levels were normalized to the ratio of miR-21-RL/FL to UT-RL/FL in 2'-OMe-NC transfected HCT-116 cells and were represented by the mean±SEM (n=3).

Figure 33:
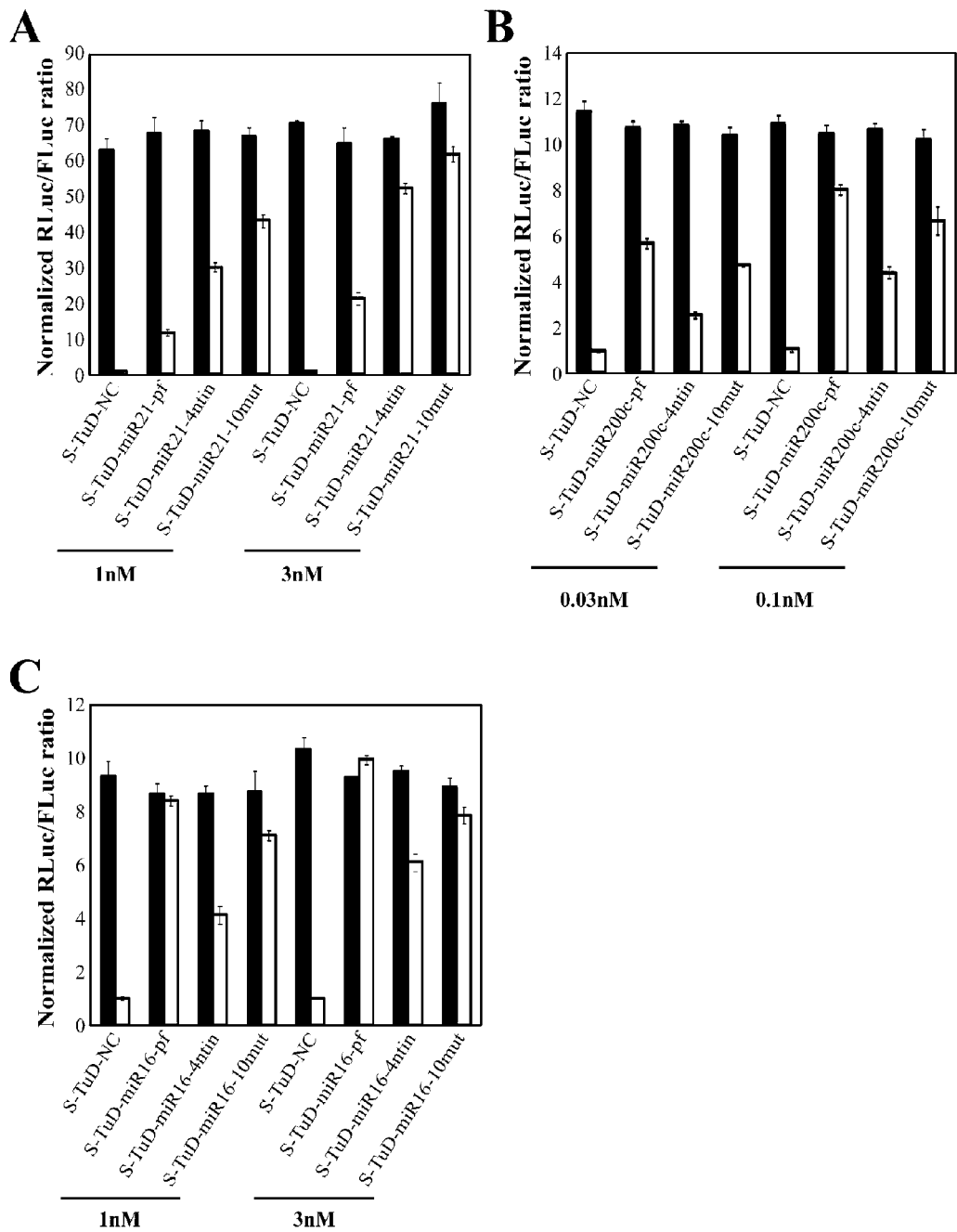

FIG. 33 shows that MBS sequences in the S-TuD (synthetic miRNA-inhibiting RNAs of FIG. 31(B) type) affect its inhibitory effects. (A) Comparison of three types of miR21-inhibiting RNAs. HCT-116 cells were transfected in similar procedures to those shown in FIG. 31C. After performing a dual luciferase assay, the expression levels were normalized to the ratio of the activity of miR-21-RL to that of FL in S-TuD-NC (negative control) transfected HCT-116 cells and are represented by the mean±SEM (n=3). (B) Comparison of three types of S-TuD-miR200c (synthetic miR200c-inhibiting RNAs of FIG. 31(B) type). S-TuD-miR200c-pf, S-TuDmiR200c-4ntin, S-TuD-miR200c-10mut were transiently transfected into HCT-116 cells together with the *Renilla* luciferase miR-200c reporter (miR-200c-RL) (open bars) or the untargeted control *Renilla* luciferase reporter (UT-RL) (black bars). In all the case, the Firefly luciferase reporter (FL) was co-transfected as a transfection control. After performing a dual luciferase assay, the expression levels were normalized to the ratio of the activity of miR-200c-RL to that of FL in S-TuD-NC transfected HCT-116 cells and are represented by the mean±SEM (n=3). (C) Comparison of three types of S-TuD-miR16 (synthetic miR16-inhibiting RNAs of FIG. 31(B) type). S-TuD-miR16-pf, S-TuD-miR16-4ntin, S-TuD-miR16-10mut were transiently transfected into HCT-116 cells together with the *Renilla* luciferase miR-16 reporter (miR-16-RL) (open bars) or the untargeted control *Renilla* luciferase reporter (UT-RL) (black bars). In all the case, the Firefly luciferase reporter (FL) was co-transfected as a transfection control. After performing a dual luciferase assay, the expression levels were normalized to the ratio of the activity of miR-16-RL to that of FL in S-TuD-NC transfected HCT-116 cells and are represented by the mean±SEM (n=3).

FIG. 34 shows structures and sequences of S-TuD (synthetic miRNA-inhibiting RNAs of FIG. 31(B) type) for miR-21, miR-200c, and miR-16. MBS represents miRNA binding site which is fully or partially complementary to target miRNA. Sequences of 4 nt insertion and 1 nt mismatch are represented. G-U pair is indicated by dot.

FIG. 35 shows dose-dependency of S-TuD-miR-21-10mut (A) or S-TuD-miR-200c-pf (B) on miRNA inhibitory activities. HCT-116 cells were transfected in similar procedures to those shown in FIG. 33. (A) A dual luciferase assay was performed 48 hrs after transfection into HCT-116 cells. Hairpin-inhibitor-miR21 was used for comparison. The ratio of miR-21-RL/FL to UT-RL/FL are represented by the mean±SEM (n=3) as the expression levels. (B) A dual luciferase assay was performed 48 hrs after transfection into HCT-116 cells. LNA-inhibitor-miR200c was used for comparison. The ratio of miR-200c-RL/FL to UT-RL/FL are represented by the mean±SEM (n=3) as the expression levels.

Figure 36:
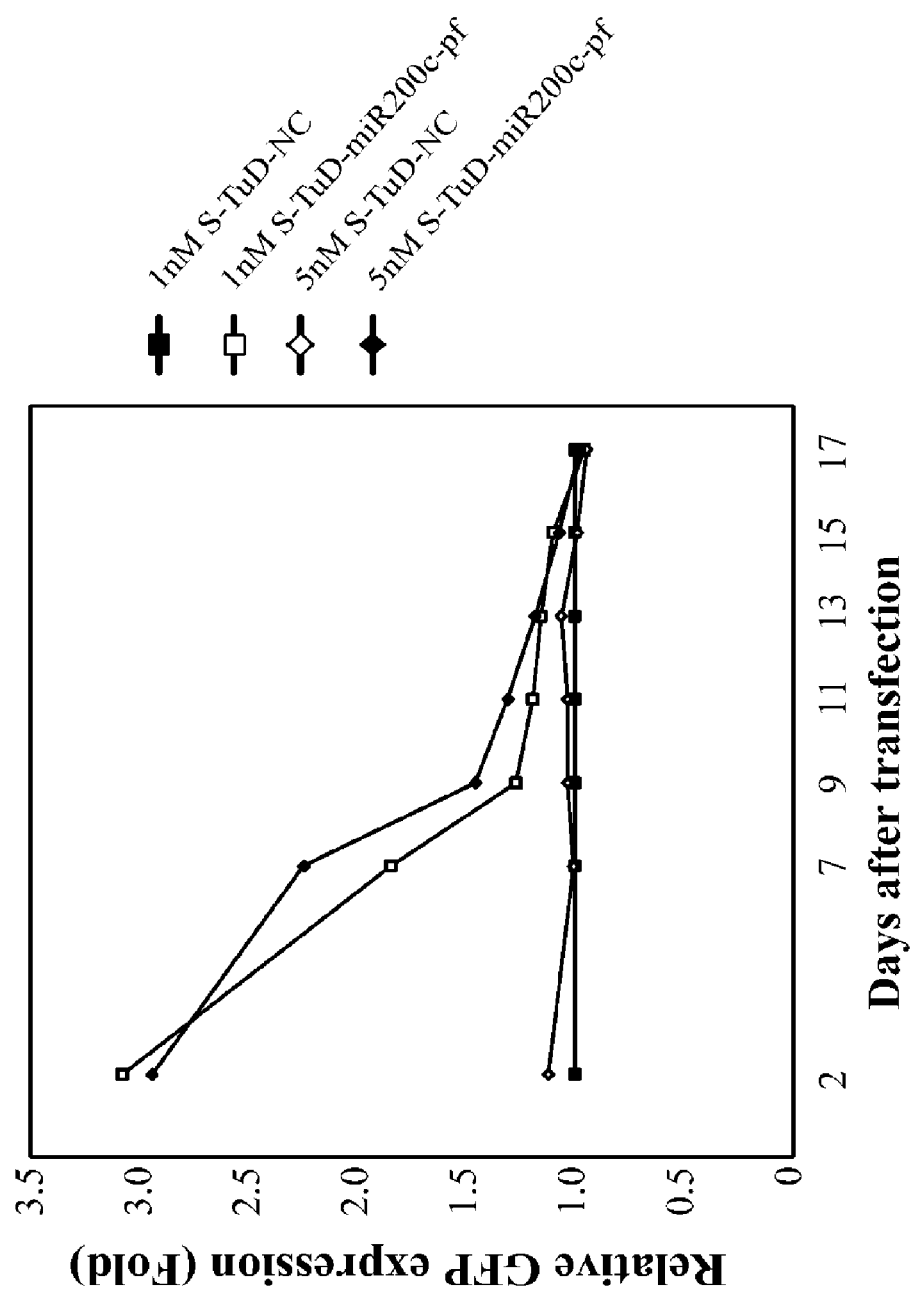

FIG. 36 shows time course of the inhibitory effects of S-TuD-miR200c-pf activity. HCT116-miR200cT cells were transfected with S-TuD-miR200c-pf and S-TuD-NC at concentrations of 1 or 5 nM. The GFP expression levels of these transfected cells were analysed and highly GFP expressing cells were sorted 2 days after the transfection. The GFP expression levels of these sorted cells were analysed the time indicated. Relative GFP expression levels were normalized to those of 1 nM S-TuD-NC transfected HCT116-miR200cT cells.

DETAILED DESCRIPTION OF THE INVENTION

Figure 1:
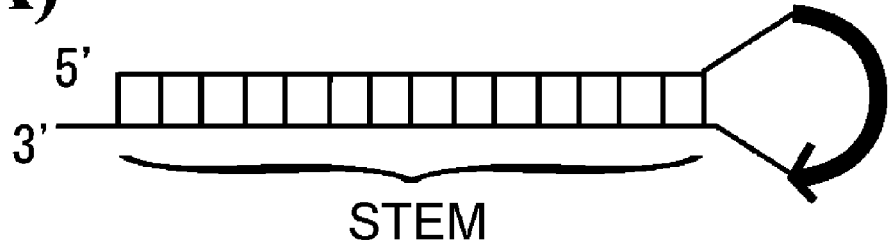
FIG. 1 shows the effect of the stem length of prototype decoy RNAs. (A) The structure of a prototype decoy RNA. The black thick curved arrow represents MBS (5' to 3'). (B) Lentiviral vectors for expressing these decoy RNAs were individually introduced into HeLaS3 cells carrying both the miR-140-3p reporter and miR140-5p/140-3p vector. Six to ten days after the introduction, the median values of GFP expression level in the whole population were determined by FACS analysis. The expression levels presented as mean±SEM were normalized against those of HeLaS3 cells carrying the miR-140-3p reporter alone. An shRNA that targets the Cre recombinase gene was used as the negative control (NC).

The present invention relates to miRNA-inhibiting complexes that can efficiently and specifically inhibit miRNAs. The miRNA-inhibiting complexes of the present invention comprise a double-stranded or multiple-stranded structure, wherein at least one miRNA-binding sequence (MBS)-comprising strand is linked to the two strands of the double-stranded or multiple-stranded structure on at least one end. In the present invention, this double-stranded or multiple-stranded structure is called "first double-stranded structure" to be distinguished from additional double-stranded or multiple-stranded structures comprised in the complexes of the present invention (see below). A complex of the present invention may or may not be single-stranded (that is, a single molecule linked by covalent bonds), and for example, it may be composed of a single strand, double strand, or multiple strands which are more than two strands. For example, the present invention includes a complex comprising a double-stranded RNA in which single RNA strands comprising an MBS are each linked to one of the two strands on one end of the double-stranded structure. Furthermore, a single RNA strand comprising at least one MBS may be linked to the two strands of the double-stranded structure on one end. In this case, the MBS-comprising RNA strand links the two strands on one end of the double-stranded structure (e.g., FIG. 1). The RNA linking the two strands of the double-stranded structure comprises at least one MBS; however, for example, two, three, or more MBSs may be comprised (e.g., FIG. 2A). The double-stranded structure comprises a stem loop or hairpin. That is, the double-stranded structure may be a double-stranded structure comprised in a stem loop or hairpin.

In the present invention, a miRNA-inhibiting complex may be a structure that has a double-stranded structure and which comprises at least one RNA or analog thereof. Preferably, the complex comprises one or two molecules comprising an RNA or analog thereof.

In the present invention, "miRNA-binding sequence (MBS)" refers to a sequence that binds to a miRNA. An MBS comprises at least a portion complementary to a miRNA so that it can bind to the miRNA. As shown in the examples, an MBS may or may not have a sequence completely complementary to a miRNA. An MBS may be a naturally-occurring RNA sequence targeted by a miRNA. For example, an MBS consecutively or non-consecutively comprises at least ten nucleotides, such as eleven or more, twelve or more, 13 or more, 14 or more, 15 or more, 16 or more, 17 or more, 18 or more, 19 or more, 20 or more, 21 or more, 22 or more, 23 or more, or 24 or more nucleotides that are complementary to an miRNA. The complementary nucleotides are preferably consecutive, or have a gap at three sites or less, two sites or less, or preferably one site. The gaps may be unpairing (bulges) on the MBS side and/or the miRNA side. Gaps at one site may have bulge nucleotides on only one of the strands, or unpaired nucleotides on both of the strands. Preferably, they are designed to include unpaired nucleotides at least on the MBS side. The number of nucleotides in a single bulge or mismatch is, for example, six nucleotides or less, preferably five nucleotides or less, four nucleotides or less, three nucleotides or less, two nucleotides or less, or one nucleotide on a single strand. In the present invention, an MBS that can form a bulge showed a higher miRNA-inhibiting effect than an MBS consisting of a completely complementary sequence (Example 4). Therefore, to obtain higher miRNA-inhibiting effects, an MBS is designed to preferably form a bulge. For example, the following MBSs are not readily degraded, and their high activity can be expected: an MBS in which the nucleotides at position 10 and/or position 11 from the 3' end are not complementary to the target miRNA, or an MBS comprising additional nucleotides that are not complementary to an MBS between positions 10 and 11 (i.e., the nucleotides at position 10 and/or position 11 from the 5' end of the target miRNA, or an MBS comprises unpaired insert between the nucleotides that are complementary to the nucleotides at positions 10 and 11 from the 5' end of the target miRNA). Specifically, an MBS in which the nucleotides at position 10 and/or position 11 from the 3' end are not complementary to the target miRNA, or an MBS comprising one or more additional nucleotides between positions 10 and 11 (i.e., an MBS in which the corresponding nucleotides at position 10 and/or position 11 from the 5' end of the target miRNA are not complementary to the target miRNA, or an MBS comprising one or more additional nucleotides between the corresponding nucleotides at positions 10 and 11 from the 5' end of the target miRNA) can preferably be used. In this case, for example, an MBS may be designed so that the nucleotides including those at positions 10 and 11 from the 5' end of a miRNA are unpaired. For example, an MBS may be designed so that nucleotides at positions 9 to 11, 10 to 12, or 9 to 12 are unpaired. Alternatively, an MBS may be designed so that no nucleotide becomes unpaired on the miRNA side, but the MBS has nucleotides that become unpaired between positions 10 and 11 from the 3' end on the MBS side, i.e., between the sites corresponding to positions 10 and 11 from the 5' end of the target miRNA. Nucleotides that become unpaired may be present on the miRNA side and/or the MBS side. Preferably, they exist at least on the MBS side. The number of nucleotides that become unpaired in each strand can be adjusted appropriately. For example, it is one to six nucleotides, preferably one to five nucleotides, or more preferably three to five nucleotides, such as three, four, or five nucleotides.

If the miRNA inhibitor is synthesized with RNA analogs, complete pairing between MBS and miRNA is preferred to exhibit high inhibitory effect against miRNA. However, one or more mismatches can still be introduced into MBS in order to suppress the formation of base-pairing between the MBSs contained in the miRNA inhibitor RNA molecule.

Figure 12:
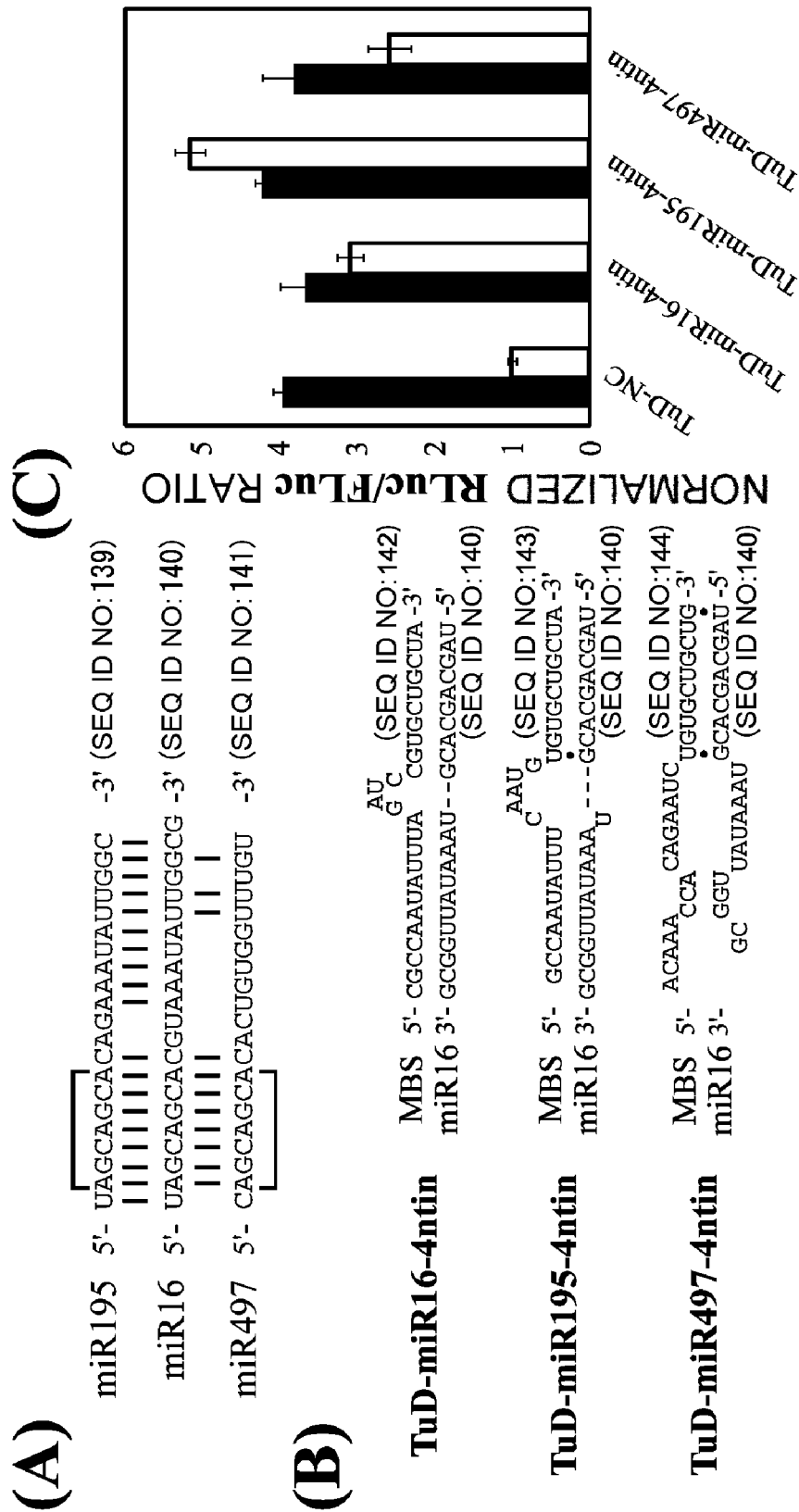
FIG. 12 shows the inhibitory effect of miRNA-inhibiting RNAs on a target miRNA family. (A) The sequences of miR-16, 195, and 497 and their homology are shown. The sequence indicated in the brackets is the seed site, and the black bars indicate homologous sites. (B) The binding of TuD-miR-16-4ntin, TuD-miR-195-4ntin, and TuD-miR497-4ntin MBSs to miR-16 is shown. The black dots indicate G-U bonds. (C) A miRNA-inhibiting RNA expression plasmid vector was transfected into HCT-116 cells, together with the Renilla luciferase miR-16 reporter (white bar) or non-targeted control Renilla luciferase reporter (black bar), in addition to a firefly luciferase reporter as a transfection control, and dual luciferase assay was carried out. The expression levels were normalized against the value for HCT-116 cells transfected with the TuD-NC vector, and presented as mean±SEM (n=3).
Figure 13:
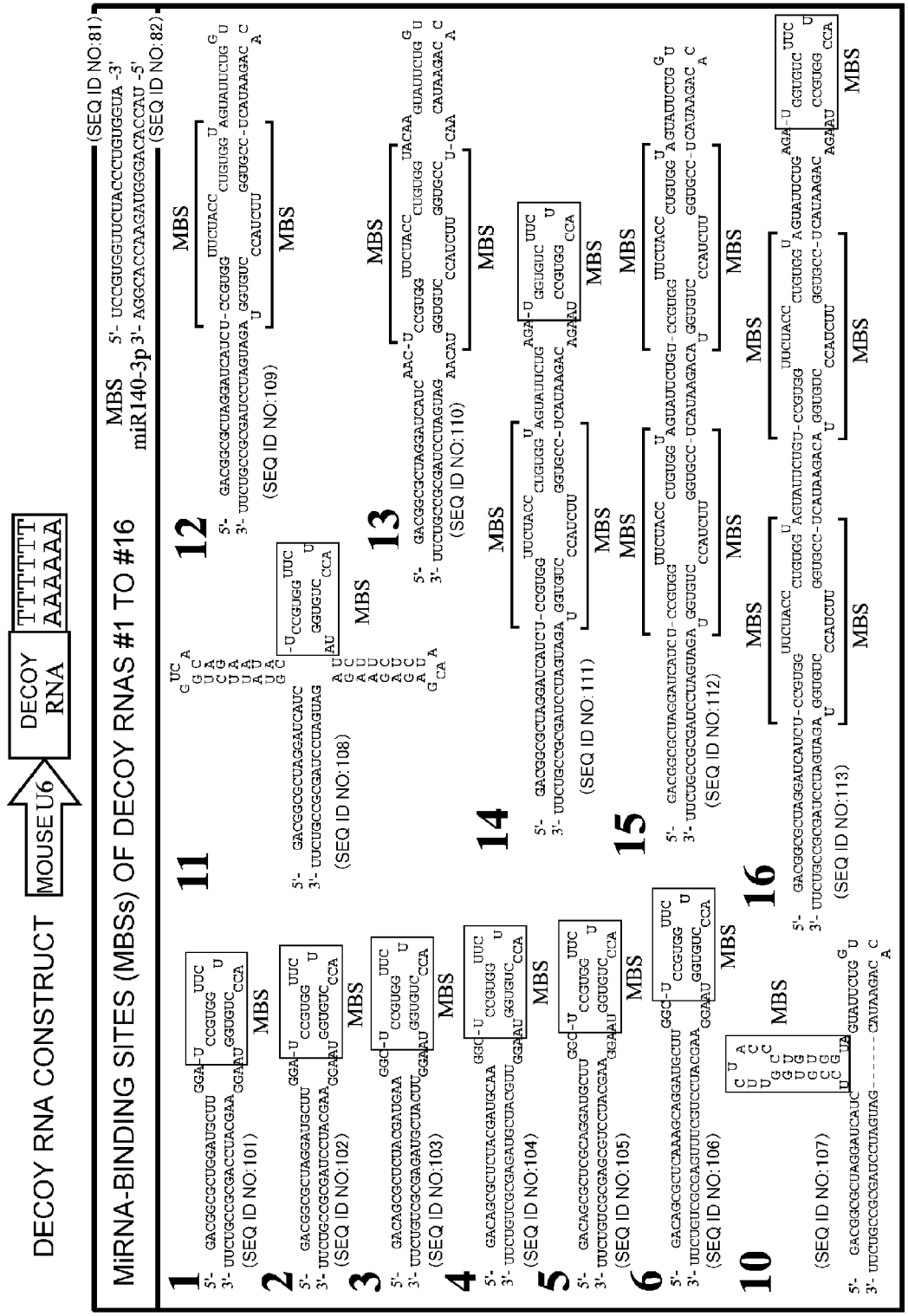
FIG. 13 shows the structures and sequences of decoy RNAs for miR140-3p. MBS represents a miRNA-binding site that is completely or partially complementary to miR140-3p.
Figure 14:
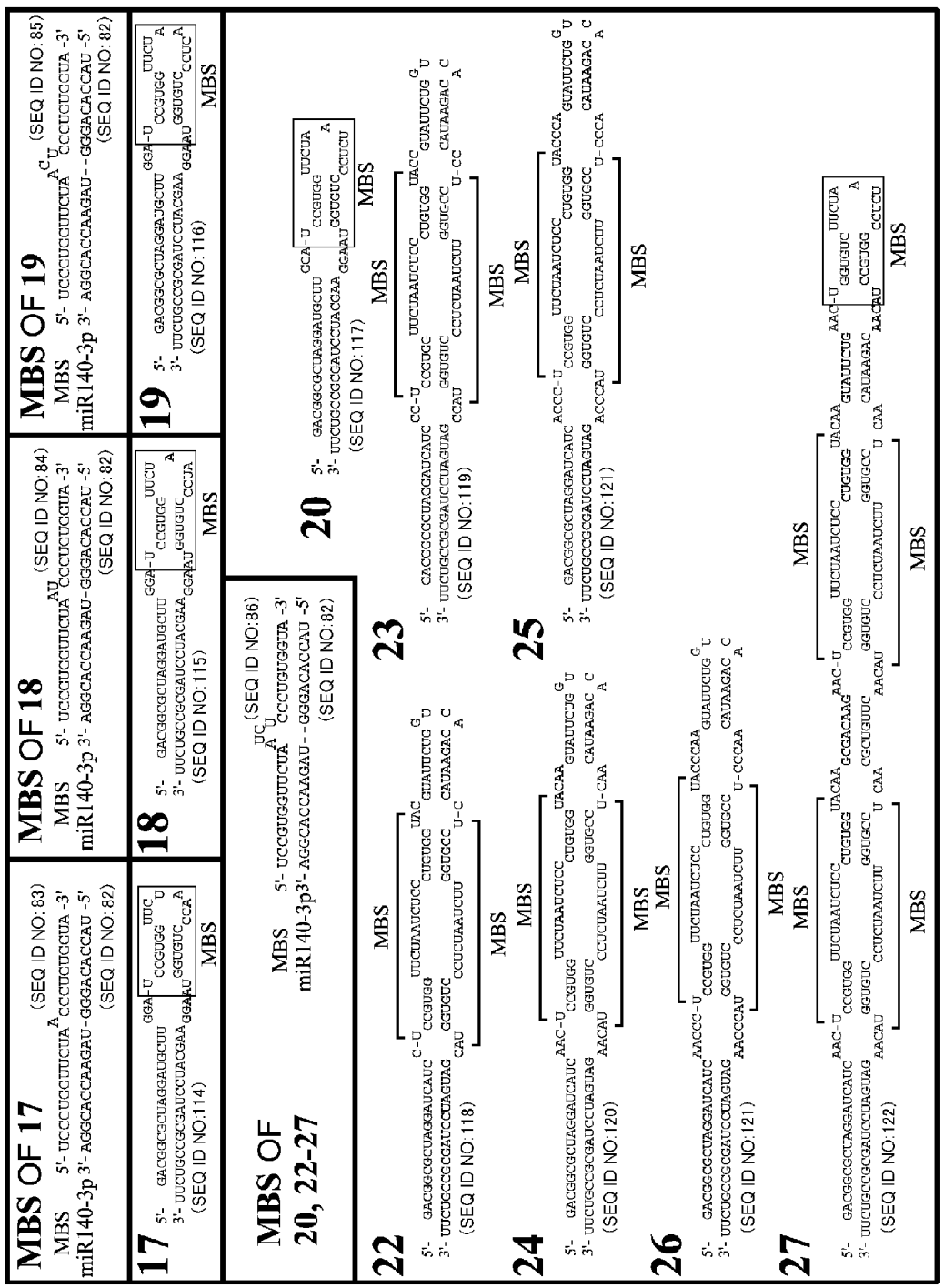
FIG. 14 shows the structures and sequences of decoy RNAs for miR140-3p (continuation of FIG. 13).

It is known that matching of nucleotides at positions 2 to 7 or positions 3 to 8 from the 5' end (called "seed region") of an miRNA is important for target recognition by the miRNA (Jackson A L et al., RNA 12(7):1179-1187, 2006; Lewis B P et al., Cell 120: 15-20, 2005; Brennecke et al. PLoS BIOLOGY 3, 0404-0418, 2005; Lewis et al. Cell 115, 787-798, 2003; Kiriakidou et al. Genes & Development 18, 1165-1178, 2004). In fact, it was shown that the miRNA-inhibiting RNAs of the present invention can effectively inhibit miRNAs even when they carry an MBS that matches with only the seed region but has low complementarity with other regions (Example 6, FIG. 12). In the present invention, an MBS preferably has complete complementarity to a miRNA seed region (nucleotides at positions 2 to 7 and/or positions 3 to 8 from the 5' end of a miRNA). In this case, a G:U pair (U:G pair) may be considered to be complementary. However, it is preferable to consider only G:C (C:G) and A:U (U:A) pairs as complementary. In the present invention, preferably, an MBS is completely complementary to a miRNA seed region (nucleotides at positions 2 to 7 and/or positions 3 to 8 from the 5' end of a miRNA), and it consecutively comprises at least eight nucleotides, more preferably nine nucleotides, and even more preferably ten nucleotides that are complementary to the miRNA. Furthermore, an MBS of the present invention preferably comprises a total of eleven or more nucleotides, more preferably twelve or more nucleotides, or even more preferably 13 or more nucleotides that are complementary to a miRNA.

Preferably, an MBS is a sequence that hybridizes with a miRNA sequence under physiological conditions. Physiological conditions are, for example, 150 mM NaCl and 15 mM sodium citrate at pH 7.0 and 37° C. More preferably, an MBS is a sequence that hybridizes with a miRNA sequence under stringent conditions. Stringent conditions include, for example, conditions of 1×SSC ("1×SSC" means "150 mM NaCl and 15 mM sodium citrate at pH 7.0") or 0.5×SSC at 42° C., more preferably conditions of 1×SSC or 0.5×SSC at 45° C., and even more preferably conditions of 1×SSC or 0.5× SSC at 50° C. In hybridization, for example, either one of a miRNA sequence-comprising RNA and an MBS-comprising RNA is labeled, and the other is immobilized onto a membrane, and then the two are hybridized. Hybridization may be carried out under conditions such as in a solution containing 5×SSC, 7% (W/N) SDS, 100 μg/mL denatured salmon sperm DNA, and 5× Denhardt's solution (1× Denhardt's solution contains 0.2% polyvinyl pyrrolidone, 0.2% bovine serum albumin, and 0.2% Ficoll), for example at 37° C., 45° C., or 50° C. After incubation for a sufficient time (for example, three, four, five, or six hours or more), washing is carried out under the above conditions. Then, one can determine whether a nucleic acid is hybridized under the conditions by detecting whether the labeled nucleic acid is hybridized.

Alternatively, an MBS preferably shows high homology to the complementary sequence of a miRNA sequence. "High homology" refers to a nucleotide sequence identity of, for example, 70% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 93% or more, 95% or more, 96% or more, 97% or more, 98% or more, or 99% or more. The nucleotide sequence identity can be determined using, for example, the BLAST program (Altschul, S. F. et al., J. Mol. Biol. 215: 403-410, 1990). For example, in the BLAST web page of the National Center for Biotechnology Information (NCBI), a search can be carried out using default parameters (Altschul S. F. et al., Nature Genet. 3:266-272, 1993; Madden, T. L. et al., Meth. Enzymol. 266:131-141, 1996; Altschul S. F. et al., Nucleic Acids Res. 25:3389-3402, 1997; Zhang J. & Madden T. L., Genome Res. 7:649-656, 1997). For example, an alignment of two sequences can be produced by the blast 2 sequences program (Tatiana A et al., FEMS Microbiol. Lett. 174:247-250, 1999) which compares two sequences, and the sequence identity can be determined. Gaps outside of a miRNA nucleotide sequence are ignored, and inner gaps are treated, for example, in the same manner as mismatches. The value of identity in alignment with the whole miRNA nucleotide sequence (with a total nucleotide length determined by adding the gaps inside the sequence) is calculated. However, as shown in the Examples, a mismatch between an MBS and a miRNA may increase the miRNA-inhibiting activity. Therefore, for example, it is preferable to calculate the identity by ignoring gaps inserted into a miRNA sequence inside alignment.

Alternatively, an MBS preferably comprises a sequence with one or more nucleotide insertions, substitutions, and/or deletions in a sequence complementary to a miRNA sequence. Preferably, an MBS comprises a sequence that has eight or less, seven or less, six or less, five or less, four or less, three or less, two or less, or one nucleotide insertion, substitution, and/or deletion in a sequence complementary to a miRNA sequence. More preferably, an MBS comprises a sequence that has eight or less, seven or less, six or less, five or less, four or less, three or less, two or less, or one nucleotide insertion in a sequence complementary to a miRNA sequence. In the present invention, it was shown that an MBS with a mismatch sequence has higher miRNA-inhibiting activity than an MBS with a sequence completely complementary to a miRNA sequence. This is thought that because when an MBS is completely complementary to a miRNA, it may be cleaved by RISC containing the miRNA, and thus the expression level of the miRNA-inhibiting RNA is decreased. In particular, high activity can be expected from an MBS designed to have unpairing at the nucleotides of position 10 and/or position 11 from the 3' end of the MBS (i.e., the nucleotides at position 10 and/or position 11 from the 5' end of a target sequence in a miRNA that hybridizes with an MBS become unpaired when the miRNA is hybridized with the MBS), or an MBS that is designed to comprise unpaired nucleotides between the nucleotides of positions 10 and 11. Such unpairing may be, for example, a bulge on the MBS side. The number of nucleotides that form the bulge is one to six nucleotides, preferably one to five nucleotides, and more preferably three to five nucleotides (for example, three, four, or five nucleotides).

An MBS may comprise an RNA, or it may comprise a nucleic acid analog, or it may consist of a nucleic acid analog (Example 7). In particular, the miRNA-inhibiting effect is expected to be increased by converting the cleaved site in an MBS (the nucleotides of position 10 and/or position 11 from the 3' end of the MBS, etc.) into nucleic acid analogs in order to prevent cleavage. Furthermore, it is also favorable to use nucleic acids that have a backbone such as phosphorothioate and 2'-O-methyl, or a sugar (Krutzfeldt, J. et al., Nucleic Acids Res. 35: 2885-2892; Davis, S. et al., 2006, Nucleic Acids Res. 34: 2294-2304).

There are no particular limitations on the miRNAs targeted by the miRNA-inhibiting complexes of the present invention. As long as they have a miRNA structure, those derived from any species such as plants, nematodes, and vertebrates may be targeted. A very large number of miRNA sequences are known in various organisms including humans, mice, chicken, zebrafish, and *Arabidopsis thaliana* (see the webpage of miR Base::Sequences:microrna.sangerac.uk/sequences/). For example, one can target miRNAs of mammals including mice, rats, and goats, those of primates including monkeys, and those of humans. Examples include, but are not limited to, miR21 (Lagos-Quintana M et al., Science. 294: 853-858, 2001; Mourelatos Z et al., Genes Dev. 16:720-728, 2002; Michael M Z et al., Mol Cancer Res. 1:882-891, 2003; Dostie J et al. RNA. 9:180-186, 2003), miR140 (Lagos-Quintana M et al., Curr Biol. 12:735-739, 2002; Cai X et al., Proc Natl Acad Sci USA. 102:5570-5575, 2005), miR1995 (Lagos-Quintana M et al., RNA. 9:175-179, 2003; Landgraf P et al., Cell. 129:1401-1414, 2007), miR16 (Lagos-Quintana M et al., Science. 294:853-858, 2001; Mourelatos Z et al., Genes Dev. 16:720-728, 2002; Lim L P et al., Science. 299:1540, 2003; Calin G A et al., Proc Natl Acad Sci USA. 99:15524-15529, 2002; Michael M Z et al., Mol Cancer Res. 1:882-891, 2003), and miR497 (Bentwich I et al., Nat Genet. 37: 766-770, 2005; Landgraf P et al., Cell. 129:1401-1414, 2007; Haraguchi, T. et al., Nucleic Acids Res., 37:e43; Sakurai, K. et al., Cancer Res., doi: 10.1158/0008-5472.CAN-10-2345 Dec. 28, 2010; Lu, Z. et al., EMBO J. 30: 57-67, 2011).

Furthermore, the above miRNA-inhibiting complexes of the present invention include a miRNA-inhibiting complex that comprises a second multiple-stranded structure in addition to a first multiple-stranded structure, and which has a structure in which single RNA strands comprising an MBS are each linked to one of the two strands of the first multiple-stranded structure on one end, wherein the other ends of the RNA strands are each linked to one of the two strands of the second multiple-stranded structure on one end so that the strands are placed between the first multiple-stranded structure and the second multiple-stranded structure. The multiple-stranded structure may be a double strand, or a quadruple strand such as a G-quadruplex. Preferably, the first multiple-stranded structure is a double strand, and the second multiple-stranded structure is a double or quadruple strand. For example, the present invention relates to a miRNA-inhibiting complex that comprises a second double-stranded structure in addition to a first double-stranded structure, and which has a structure in which single RNA strands comprising an MBS are each linked to one of the two strands on the end to which the MBSs are linked in the first double-stranded structure, wherein the other ends of the RNA strands are each linked to one of the two strands of the second double-stranded structure so that the strands are placed between the first double-stranded structure and the second double-stranded structure. For example, the above RNA complex has a structure that comprises at least two double-stranded structures, wherein the four RNA strands constituting the two double-stranded structures are each linked to an RNA comprising an MBS without mediation of any of the remaining three strands. More simply stated, the above complex is a miRNA-inhibiting complex in which two RNA strands comprising an MBS are each bound to one of the strands of two double-stranded structures so that the strands are placed between the two double-stranded structures (FIG. 2 (C)). More specifically, the present invention includes an RNA which is an RNA complex having the structure of FIG. 2 (C), wherein the RNA strands a and b are placed between the double-stranded structures I and II, and one or more MBSs are comprised in each of a and b above. The two RNA strands comprising an MBS are linked to the respective paired strands in the double-stranded structures. Therefore, the directions of the RNA strands are opposite to each other (FIG. 2, #12 to #16). By adding an MBS to each of the two strands in this manner, higher miRNA-inhibiting activity can be exerted.

In the two RNA strands comprising an MBS present between two double-stranded structures, one or more MBSs are comprised in each strand. These MBSs may have the same or different sequences. Furthermore, they may target the same miRNA, or they may have sequences that bind to different target miRNAs. For example, one strand may comprise two or more, for example, two, three, four, or five MBSs (FIG. 2, #12 to #16). For example, one or two MBSs may be comprised in each strand positioned between two double-stranded structures. For example, a miRNA-inhibiting complex of the present invention may comprise two MBSs in total, and the two MBSs may have the same sequence or sequences that bind to the same miRNA.

Each of the strands that are paired in a double strand comprised in a miRNA-inhibiting complex of the present invention may be separate RNA molecules as described above. Alternatively, one or both ends of the double strand may be linked, and may be linear or cyclic. "Linear" is a word used in contrast to "cyclic" and only means that ends are present. Of course, it does not mean that a secondary structure is not formed. A miRNA-inhibiting complex composed of a linear single-stranded RNA can be produced, for example, by a one-time RNA synthesis, or it may be expressed from a single expression unit using an expression vector or such. For example, when two double-stranded structures are included, two strands on one end (the side to which an MBS is not bound) of the second double-stranded structure can be linked by a loop so that the whole molecule becomes single-stranded. In the sequence linking the two strands, one or more MBSs may be included (FIG. 2, #2, #11, #13, #14, and #16). To make the sequence as compact as possible, the two strands can be linked by a short loop. For example, the two strands can be linked, for example, by one to ten nucleotides, preferably one to eight nucleotides, two to six nucleotides, three to five nucleotides, for example, four nucleotides. There is no particular limitation on the sequence, and an example is 5'-GUCA-3' (FIG. 6A). For example, the present invention includes an RNA having the structure of FIG. 2(A) #13 or FIG. 2(D), in which the RNA strands a and b are positioned between the double-stranded structures I and II, wherein the double-stranded structure II forms a hairpin (or a stem loop), and one or more MBSs are included in each of a and b above.

The miRNA-inhibiting complex of the present invention can also be composed of two single chain RNA molecules which are annealed to form a single RNA complex with the structure of FIG. 2 (C). In this case, one RNA molecule has a structure of 5'-A-MBS-B-3', and the other RNA molecule has a structure of 5'-B'-MBS-A'-3', wherein A and A' are hybridized each other, and B and B' are hybridized each other. The sequence of A can be complementary to the sequence of A', and the sequence of B can be complementary to the sequence of B'. The pair of the MBS sequences may or may not have the same sequence. The MBS can be connected to A, A', B, or B' directly or via a short linker that may consist of one to five bases.

There is no particular limitation on the sequences of the double-stranded structures comprised in the miRNA-inhibiting complexes of the present invention, but they preferably have a length of four base pairs or more. In particular, at least one of the double-stranded structures comprised in the RNA complexes of the present invention (that is, a first double-stranded structure) has important functions in the nuclear export of RNA complexes. The chain length of this double strand may be, for example, 15 to 50 base pairs, preferably 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 nucleotides or more, or 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, or 18 nucleotides or less. In a preferred embodiment, the length of the base pairs of the double-stranded structure is, for example, 15 to 30, preferably 16 to 28, more preferably 17 to 25, and even more preferably 17 to 24, for example, 17, 18, 19, 20, 21, 22, 23, or 24. Although high activity can be exerted when the length is longer than 20 bp, dsRNAs with more than 20 bp can be potential targets for cleavage by Dicer in the cytoplasm. Therefore, to avoid this, the length of a double-stranded structure comprised in a complex of the present invention can be 20 bp or less, for example, 19 bp or less, or 18 bp or less.

When second or further double-stranded structures are comprised in miRNA-inhibiting complexes of the present invention, there is no particular limitation on the sequence and length of such double-stranded structures. For example, the length of these double-stranded structures can be made to be shorter than that of the first double-stranded structure in order to make the whole miRNA-inhibiting complex compact. The chain length of each double strand can be adjusted appropriately, and for example, it may be 4 bp to 20 bp, for example, 5 bp to 15 bp, 5 bp to 12 bp, 5 bp to 10 bp, 6 bp to 9 bp, or 7 bp to 8 bp.

The sequences of base pairs forming the double-stranded structure can be designed appropriately so that the double strand can be formed specifically and stably in a miRNA-inhibiting complex. For example, it is preferable to avoid a homopolymeric sequence with a long repetition of the same nucleotide (for example, eight or more nucleotides, preferably seven or more nucleotides, more preferably five or more nucleotides, even more preferably four or more nucleotides, and yet even more preferably three or more nucleotides). Furthermore, it is also preferable to avoid sequences in which sequences of several nucleotides are repeated in tandem, such as two-nucleotide repeat sequences or three to four nucleotide repeat sequences. The GC content of the double-stranded portion can be adjusted appropriately, and is for example, 12% to 85%, preferably 15% to 80%, 20% to 75%, 25% to 73%, 32% to 72%, 35% to 70%, 37% to 68%, or 40% to 65%. The sequences of stem I and stem II shown in FIG. 6A can be presented as examples, but they are not limited thereto. An example of a quadruple strand is a G-quadruplex, which is specifically the sequence of GGG-loop-GGG-loop-GGG-loop-GGG Herein, the loop sequences can be selected appropriately. For example, all of the three loops may be a single nucleotide (for example, M (A or C)), or three nucleotides (SEQ ID NOs: 167, 168, and such).

MBSs and double-stranded structures may be linked directly, or they may be linked via other sequences. For example, an MBS can be linked to the end of a double-stranded structure via a suitable linker or a spacer sequence. While significant inhibitory activity can be obtained by directly linking an MBS to the double-stranded portion, addition of a linker (or also referred to as a spacer) further increases the inhibitory effect on miRNA (Example 4). The linker or spacer sequence between an MBS sequence and a double-stranded structure may increase the accessibility of the MBS to a miRNA present in RISC. The length of the linker or spacer may be adjusted appropriately, and examples include one to ten nucleotides, preferably one to nine nucleotides, one to eight nucleotides, one to seven nucleotides, one to six nucleotides, one to five nucleotides, one to four nucleotides, and one to three nucleotides. For example, when linking two or more MBSs, it is preferable to link them via a linker or spacer. There is no particular limitation on the sequence of the linker or spacer, and for example, it may be a sequence comprising A and/or C, or a sequence comprising more A and/or C than other nucleotides. Furthermore, it is preferable to pay attention not to make the linker or spacer sequences form stable base pairs with opposite linker or spacer sequences, or MBSs. Examples include AAC, CAA, ACC, CCA, and a sequence comprising any one of these. A pair of linker or spacer sequences that are added to both sides of an MBS may be inverted sequences (mirror-image sequences). For example, AAC may be added to the 5' side of an MBS and CAA may be added to the 3' side.

Furthermore, nucleic acids constituting miRNA-inhibiting complexes of the present invention may be modified. For example, nucleotides constituting a nucleic acid may be naturally-occurring nucleotides, modified nucleotides, artificial nucleotides, or combinations thereof. Furthermore, nucleic acids comprised in miRNA-inhibiting complexes of the present invention may comprise RNAs, or may be RNA/DNA chimeras. They may comprise other nucleic acid analogs, or any combination thereof. The nucleic acids include not only those linked by phosphodiester bonds, but also those having amide bonds or other backbones (peptide nucleic acids (PNAs) and such). The nucleic acid analogs include, for example, naturally-occurring and artificial nucleic acids, and they may be nucleic acid derivatives, nucleic acid analogs, nucleic acid relatives, and such. Such nucleic acid analogs are well known in the art, and examples include, but are not limited to, phosphorothioate, phosphoramidate, methylphosphonate, chiral methylphosphonate, 2'-O-methylribonucleotide, and peptide nucleic acid (PNA). The PNA backbones may include a backbone comprising aminoethylglycine, polyamide, polyethyl, polythioamide, polysulfinamide, polysulfonamide, or a combination thereof (Krutzfeldt, J. et al., Nucleic Acids Res. 35: 2885-2892; Davis, S. et al., 2006, Nucleic Acids Res. 34: 2294-2304; Boutla, A. et al., 2003), Nucleic Acids Res. 31: 4973-4980; Hutvagner, G. et al., 2004, PLoS Biol. 2: E98; Chan, J.A. et al., 2005, Cancer Res. 65: 6029-6033; Esau, C. et al., 2004, J. Biol. Chem. 279: 52361-52365; Esau, C. et al., 2006, Cell Metab. 3: 87-98).

Modification of nucleic acids may be carried out to inhibit degradation by endonucleases. Particularly preferred modifications include 2' or 3' glycosylation, for example, 2'-O-methyated (2'-O-Me) nucleotides, or 2'-deoxynucleotides, or 2'-fluoro, difluorotoluyl, 5-Me-2'-pyrimidine, 5-allylaminopyrimidine, 2'-O-methoxyethyl (2'-O-MOE), 2'-O-aminopropyl (2'-O-AP), 2'-O—N-methylacetamide (2'-O-NMA), 2'-O-dimethylaminoethyloxyethyl (2'-DMAEOE), 2'-O-dimethylaminoethyl (2'-DMAOE), 2'-O-dimethylaminopropyl (2'-O-AP), 2'-hydroxynucleotide, phosphorothioate, 4'-thionucleotide, 2'-O-trifluoromethylnucleotide, 2'-O-ethyl-trifluoromethoxynucleotide, 2'-O-difluoromethoxyethoxynucleotide, or 2'-ara-fluoro nucleotide, locked nucleic acid (LNA), ethylene nucleic acids such as 2'-O, 4'-C-ethylene bridged nucleic acid (ENA), other bridged nucleic acid (BNA), hexitol nucleic acid (HNA), morpholino nucleic acid, tricyclo-DNA (tcDNA), polyether nucleic acid (U.S. Pat. No. 5,908,845), cyclohexene nucleic acid (CeNA), 2'-methoxyethylated RNA, and combinations thereof. Furthermore, difluorotoluyl (DFT) modifications such as 2,4-difluorotoluyl uracil, or substitution of guanidine with inosine may be carried out.

Furthermore, the nucleic acids may comprise a conjugate on the end. Examples of the conjugate include lipophilic substances, terpenes, protein-binding substances, vitamins, carbohydrates, retinoids, and peptides. Specific examples include C5-aminoalkyl dT, naproxen, nitroindol, folic acid, colanic acid, ibuprofen, retinoid, polyethyleneglycol (PEG), C5 pyrimidine linker, glyceride lipids (for example, dialkylglyceride derivative), vitamin E, cholesterol, thiocholesterol, dU-cholesterol, alkyl chains, aryl groups, heterocyclic complexes, and modified sugars (D-ribose, deoxyribose, glucose, and such). The conjugates and the nucleic acids can be linked, for example, via any linker, and specific examples include pyrrolidine linkers, serinol linkers, aminooxy or hydroxyprolinol linker, and such. Furthermore, transcellular signals can be appropriately added to the nucleic acids. For example, various cell-penetrating peptides for introducing nucleic acids into cells are known (WO2008/082885). Specific examples include arginine-rich peptides such as polyarginine, and they may be, for example, HIV-1 Tat(48-60), HIV-1 Rev(34-50), FHV Coat(35-49), BMV Gag(7-25), HTLV-II Rex(4-16), partial peptides thereof, or inverso or retro-inverso thereof. A preferable example is HIV-1 Tat57-49 shown in SEQ ID NO: 152. For the amino acids, the d-form may be appropriately used. Cell-penetrating peptides and such can be linked to the nucleic acids by known linkers.

The miRNA-inhibiting complexes of the present invention can be designed to be composed of a linear single-stranded nucleic acid (FIG. 2). In particular, the present invention relates to a complex in which all MBSs are concentrated on one side (the right side in FIG. 2) of a certain double-stranded structure (stem I of FIG. 2), and strands of the double-stranded structure each has a closed structure on that side (that is, they are connected by a sequence containing an MBS), and the two ends of a single-stranded RNA are present on opposite sides of the double-stranded structure (FIG. 2). Additional multiple-stranded (for example, double-stranded or quadruple-stranded) structures (stems II, III, and such of FIG. 2) may be comprised in the MBS-containing sequences. The length of the single-stranded RNA can be determined appropriately, and is, for example, 500 nucleotides or less, preferably 450 nucleotides or less, 420 nucleotides or less, 400 nucleotides or less, 380 nucleotides or less, 360 nucleotides or less, 340 nucleotides or less, 320 nucleotides or less, 300 nucleotides or less, 280 nucleotides or less, 260 nucleotides or less, 240 nucleotides or less, 220 nucleotides or less, 200 nucleotides or less, 180 nucleotides or less, 160 nucleotides or less, 140 nucleotides or less, 120 nucleotides or less, 100 nucleotides or less, or 80 nucleotides or less. For example, the length of a single-stranded RNA forming a complex having two double-stranded structures and two MBSs is, for example, 60 to 300 nucleotides, preferably 70 to 250 nucleotides, 80 to 200 nucleotides, 90 to 180 nucleotides, or 100 to 150 nucleotides. The length of a first double-stranded structure (the double-stranded structure close to the two ends of a single-stranded RNA) may be, for example, 15 to 30 bp, preferably 16 to 28 bp, more preferably 17 to 25 bp, even more preferably 17 to 24 bp, such as 17 bp, 18 bp, 19 bp, 20 bp, 21 bp, 22 bp, 23 bp, or 24 bp. A second double-stranded structure (an additional double-stranded structure comprised in MBS-containing sequences) may be made shorter than the first double-stranded structure to make the whole molecule compact, and the length may be, for example, 4 bp to 20 bp, such as 5 bp to 15 bp, 5 bp to 12 bp, 5 bp to 10 bp, 6 bp to 9 bp, or 7 bp to 8 bp.

Furthermore, the present invention relates to RNAs constituting the miRNA-inhibiting complexes of the present invention (herein, RNAs include naturally-occurring RNAs and nucleic acid analogs), and nucleic acids that encode the RNAs (DNAs or RNAs). When a miRNA-inhibiting RNA complex is composed of a single RNA molecule, the complex of the present invention can be constructed by intramolecular annealing of the RNA. Alternatively, when the complex is composed of two or more RNA molecules, the complex of the present invention can be constructed by annealing these RNAs. The RNAs can be synthesized appropriately. For example, a desired RNA can be produced by RNA chemical synthesis. Alternatively, an RNA can be expressed by an expression vector that expresses the RNA. There is no particular limitation on the expression vectors. For example, one can use desired expression vectors expressed in bacteria such as *Escherichia coli*, eukaryotic cells such as yeast, insect cells, plant cells, or animal cells. For example, one can think of inhibiting miRNA function using a vector for expression in cells of higher eukaryotes such as plants, insects, and animals, and expressing the RNA in these cells. There is no particular limitation on the promoters for transcribing RNAs. Pol I promoters, Pol II promoters, Pol III promoters, promoters of bacteriophages, and such may be used. When a bacteriophage transcriptase and a vector comprising its promoter are introduced simultaneously and then used, for example, an RNA polymerase and a promoter of T4 phage or T7 phage can be utilized. Furthermore, examples of the polymerase II (Pol II) promoters include the CMV promoter, the β-globin promoter, and such. In order to express a relatively short RNA of several hundred bases or less, it is preferable to use a polymerase III (Pol III) promoter expected to show a higher level of expression than Pol II. Examples of the Pol III promoters include the U6 promoter, H1 promoter, tRNA promoter, 7SK promoter, 5S rRNA promoter, 7SL promoter, Y3 promoter, Ad2 VAI, and VAII promoter (Das, G et al., 1988, EMBO J. 7:503-512; Hernandez, N., 1992, pp. 281-313, In S. L. McKnight and K. R. Yamamoto (ed.), Transcriptional regulation, vol. 1. Cold Spring Harbor Laboratory, Cold Spring Harbor, N.Y; Kunkel, G. R., 1991, Biochim. Biophys. Acta 1088:1-9; Lobo, S. M., and N. Hernandez, 1989, Cell 58:55-67; Mattaj, I. W et al., 1988, Cell 55:435-442; Geiduschek, E. P. and G. A. Kassavetis, 1992, pp.247-280, In Transcriptional regulation. Monograph 22 (ed. S. L. McKnight and K. R. Yamamoto), Cold Spring Harbor Laboratory Press, Cold Spring Harbor, N.Y.). In particular, Class 3 promoters found in various snRNA and cytoplasmic RNA genes can be exemplified, and examples include promoters of the U6, 7SK, hY1, hY3, H1, and MRP/ThRNA gene (Hernandez, N., 1992, pp. 281-313, In Transcriptional regulation. Monograph 22 (ed. S. McKnight and K. R. Yamamoto), Cold Spring Harbor Laboratory Press, Cold Spring Harbor, N.Y.). For example, human U6, human H1, human 7SK, mouse U6 promoters, and such can be favorably used. In particular, it is shown in the Examples that when a miRNA-inhibiting RNA of the present invention is expressed using the 7SK promoter, a target miRNA can be inhibited at a very high efficiency. When using a Pol III promoter, for example, a poly (T) tract of about four to seven nucleotides can be added downstream of a DNA encoding the RNA to be transcribed to function as a transcription terminator.

Transcription units thus constructed can be used for expression as they are, or they can be used after integration into another vector system. There is no particular limitation on the vector, and expression plasmids and desired viral vectors and such can be used. Examples of viral vectors include, but are not limited to, retroviral vectors, adenovirus vectors, adeno-associated virus vectors, and such (Miller, A. D. et al. (1991) J. Virol. 65, 2220-2224; Miyake, S. et al. (1994) Proc. Natl. Acad. Sci. USA, 91, 8802-8806; Samulski, R. J. et al. (1989) J. Virol. 63, 3822-3828). For example, a transcription unit comprising a Pol III promoter can be integrated into the LTR of a retrovirus (including a lentivirus), and then used. By integration into a retroviral vector, genes can be transfected into target cells with high efficiency. In addition, since transgenes are incorporated into the chromosome, miRNAs can be stably inhibited for a long time. There is no particular limitation on the retroviruses used, and they include, for example, ecotropic viral vectors (Kitamura, T. et al. (1995) Proc. Natl. Acad. Sci. USA. 92, 9146-9150), amphotropic viral vectors, viral vectors pseudotyped with VSV-G and such (Arai, T. et al. (1998) J. Virol. 72, 1115-1121), lentiviral vectors such as HIV vectors, SIV vectors, and FIV vectors (Shimada, T. et al. (1991) J. Clin. Inv. 88, 1043-1047). For example, MoMLV-based retroviral vectors or HIV-based lentiviral vectors can be used. When integrating a transcription unit into an LTR, for example, it can be integrated into the ΔU3 region of an LTR having a deletion at the U3 region (ΔU3) (FIG. 15). In a preferred embodiment, the vectors can express miRNA-inhibiting RNAs and inhibit miRNA function for one week or more, preferably two weeks or more, three weeks or more, four weeks or more, or one month or more after introduction into cells.

As described above, when a miRNA-inhibiting RNA complex is designed to be composed of a single-stranded linear RNA molecule, the miRNA-inhibiting RNA complex can be formed in cells. The miRNA of interest can be inhibited by simply introducing into cells one type of expression vector for transcribing the RNA; and therefore this is convenient. In this case, as already described, all of one or multiple MBSs comprised in a miRNA-inhibiting RNA complex are designed to be present on only one side of a certain double-stranded structure (a first double-stranded structure; corresponding to stem I in FIG. 2), and the double strand on this side can be designed to be linked (that is, closed) by an RNA comprising an MBS, and the other side of the double-stranded structure can be made to be two ends of the linear RNA strand. In this way, the double-stranded structure-forming portion and the portion of the two ends of the linear single-stranded RNA can be made to be constant regions independently of MBS, and the single-stranded RNA portion alone can be made to be a variable region that may vary depending on MBS. That is, RNAs with such structures have miRNA inhibition efficiency and at the same time, they can be easily produced. The MBS-containing RNAs may comprise two or more MBSs, and a sequence that forms a stem (or stem loop) between the MBSs. The stem may be, for example, a double-stranded or quadruple-stranded stem.

Figure 6:
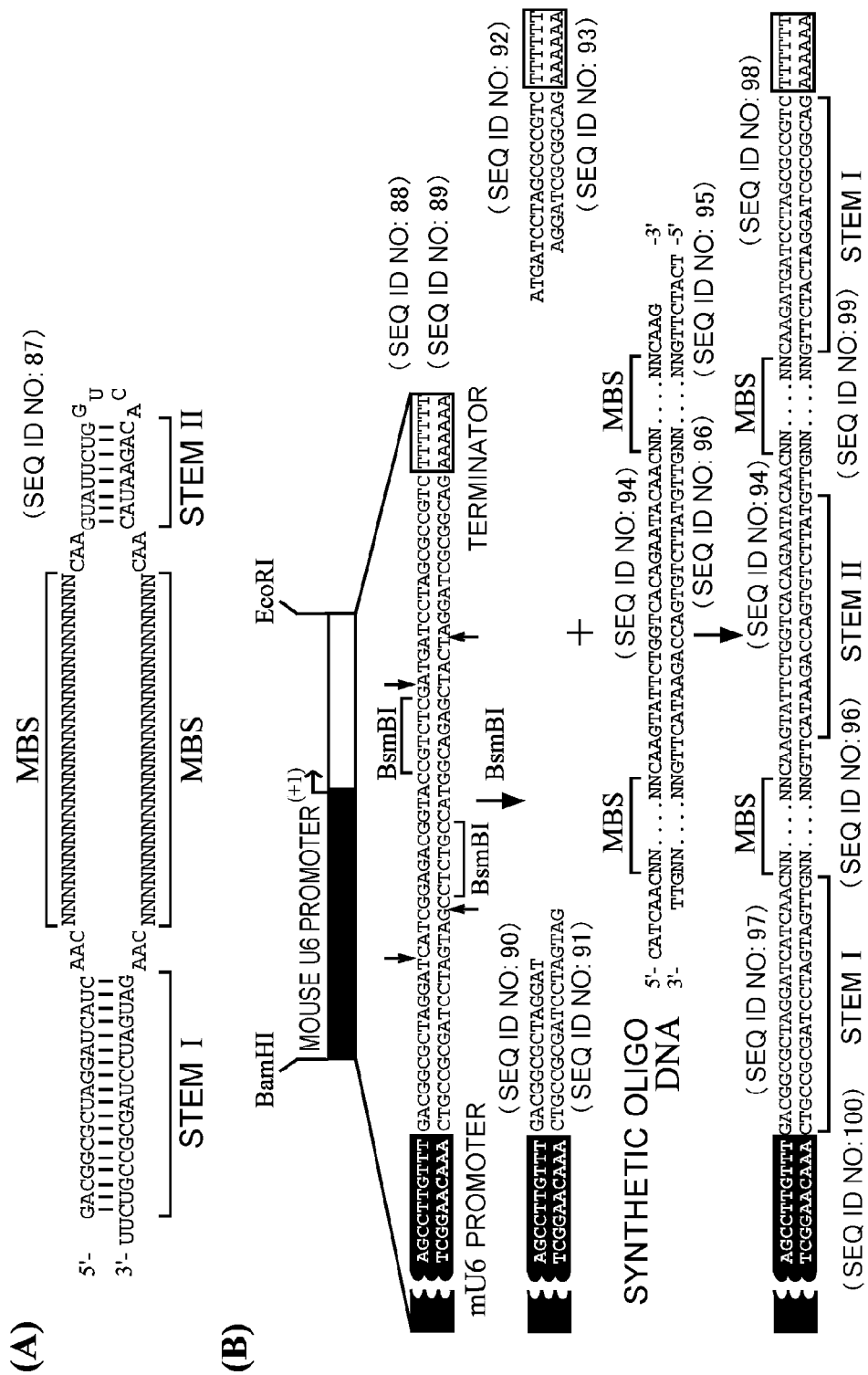
FIG. 6(A) shows a representative structure of miRNA-inhibiting RNAs of the present invention. MBS represents a miRNA-binding site. (B) Schematic diagram of the formation of a cassette for expression of miRNA-inhibiting RNAs which is driven by a mouse U6 promoter. An approximately 80- to 90-mer synthetic oligonucleotide pair is annealed, and this is cloned between the two BsmBI sites in the BamHI-EcoRI fragment derived from the original cassette to produce a miRNA-inhibiting RNA expression cassette.

If a single-stranded RNA constituting a miRNA-inhibiting RNA complex is thus designed, one can construct vectors that express a miRNA-inhibiting RNA complex for an miRNA of interest, by constructing in advance a vector that encodes a pair of complementary sequences constituting a double-stranded structure which is a constant region (for example, a cassette for expressing an miRNA-inhibiting RNA), and inserting a DNA encoding an MBS that binds to the miRNA of interest between the pair of complementary sequences (FIG. 6). A suitable promoter may be positioned upstream of the pair of complementary sequences (FIG. 6B). There is no particular limitation on the promoter; however, a Pol III promoter is favorable. Furthermore, a terminator can be positioned downstream of the pair of complementary sequences. DNAs that express a pair of complementary sequences are very useful for expressing a single-stranded RNA that constitutes a miRNA-inhibiting RNA complex. Insertion sites can be appropriately designed between a pair of complementary sequences so that MBS-encoding DNAs can be inserted. The insertion sites may be desirable restriction enzyme recognition sequences (multicloning sites) or site-specific recombination sequences such as the att sequence. Alternatively, they may be cleaved in advance for immediate insertion.

Furthermore, the present invention relates to methods for producing nucleic acids (for example, DNAs) that encode an RNA constituting an RNA complex of the present invention, wherein the methods comprise the step of inserting a double-stranded DNA encoding at least one miRNA-binding sequence into a double-stranded DNA encoding a pair of complementary sequences that form at least one double-stranded structure. The present invention also relates to methods for producing nucleic acids (for example, DNAs) that express an RNA constituting an RNA complex of the present invention, wherein the methods comprise the step of inserting a double-stranded DNA encoding at least one miRNA-binding sequence into a double-stranded DNA encoding downstream of a promoter a pair of complementary sequences that form at least one double-stranded structure.

Furthermore, the present invention relates to nucleic acids for producing nucleic acids that encode an RNA constituting an RNA complex of the present invention, which are nucleic acids encoding a pair of complementary sequences that form at least one double-stranded structure, and/or complementary strands thereof. The present invention also relates to compositions for producing nucleic acids that encode an RNA constituting an RNA complex of the present invention, wherein the compositions comprise a nucleic acid encoding a pair of complementary sequences that form at least one double-stranded structure, and/or a complementary strand thereof. The compositions may additionally and appropriately comprise a pharmaceutically acceptable carrier. Furthermore, the present invention relates to nucleic acids for producing vectors that express an RNA constituting an RNA complex of the present invention, which are nucleic acids encoding downstream of a promoter a pair of complementary sequences that form at least one double-stranded structure, and/or complementary strands thereof. The present invention also relates to compositions for producing vectors that express an RNA constituting an RNA complex of the present invention, wherein the compositions comprise a nucleic acid encoding downstream of a promoter a pair of complementary sequences that form at least one double-stranded structure, and/or a complementary strand thereof.

Furthermore, the present invention relates to nucleic acids (for example, DNAs) for producing nucleic acids that encode an RNA constituting an RNA complex of the present invention, which are nucleic acids encoding at least one miRNA-binding sequence, and/or complementary strands thereof. The present invention also relates to compositions for producing nucleic acids (for example, DNAs) that encode an RNA constituting an RNA complex of the present invention, wherein the compositions comprise a nucleic acid encoding at least one miRNA-binding sequence, and/or a complementary strand thereof.

Furthermore, the present invention relates to use of nucleic acids encoding a pair of complementary sequences that form at least one double-stranded structure, and/or complementary strands thereof, for producing nucleic acids that encode an RNA constituting an RNA complex of the present invention. The present invention also relates to use of nucleic acids encoding downstream of a promoter a pair of complementary sequences that form at least one double-stranded structure, and/or complementary strands thereof, for producing vectors that express an RNA constituting an RNA complex of the present invention. Furthermore, the present invention relates to use of nucleic acids encoding at least one miRNA-binding sequence, and/or complementary strands thereof, for producing nucleic acids that encode an RNA constituting an RNA complex of the present invention.

Furthermore, any combinations of the above-mentioned nucleic acids can be components of kits for producing nucleic acids encoding an RNA constituting an RNA complex of the present invention. In particular, the present invention relates to kits that comprise a nucleic acid encoding a pair of complementary sequences that form at least one double-stranded structure, and a complementary strand thereof. The nucleic acid and complementary strand may form a double-stranded DNA. Furthermore, a double-stranded DNA comprising a pair of complementary sequences may be operably linked to a promoter and/or a terminator. The nucleic acid may be, for example, an expression plasmid. Furthermore, the kits may further comprise a nucleic acid encoding at least one miRNA-binding sequence and/or a complementary strand thereof. For example, the present invention relates to kits for producing vectors that express an RNA complex of the present invention, which comprise (a) a nucleic acid comprising downstream of a promoter a pair of complementary sequences that form at least one double-stranded structure, and a site for inserting a nucleic acid between the pair of complementary sequences; and (b) a nucleic acid encoding at least one miRNA-binding sequence.

Nucleic acids encoding an RNA complex of the present invention can be obtained by simply inserting a nucleic acid encoding at least one miRNA-binding sequence between the above-mentioned nucleic acids encoding a pair of complementary sequences that form at least one double-stranded structure. The structure of each nucleic acid is as described for the RNA complexes of the present invention. For example, a pair of complementary sequences that form a double-stranded structure can be appropriately determined, and its chain length may be for example, 15 to 50 base pairs, preferably 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 nucleotides or more, or 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, or 18 nucleotides or less. In a more preferred embodiment, the length of the base pairs of a double-stranded structure is for example, 15 to 30, preferably 16 to 28, more preferably 17 to 25, and even more preferably 17 to 24, for example, 17, 18, 19, 20, 21, 22, 23, or 24. In a preferred embodiment, the nucleic acid is a double-stranded nucleic acid and a desirable promoter is operably linked thereto. The promoter is preferably a Pol III promoter. A site for inserting a nucleic acid can be placed between a pair of complementary sequences, and for example, a restriction enzyme recognition sequence can be carried to allow easy insertion of a nucleic acid. That is, the present invention relates to vectors for producing nucleic acids that express an RNA complex of the present invention, which comprise a nucleic acid comprising downstream of a promoter a pair of complementary sequences that form at least one double-stranded structure and a site for inserting a nucleic acid between the pair of complementary sequences. The BsmBI sequence can be exemplified as a restriction enzyme recognition sequence; however, this is only an example, and the sequence can be appropriately selected.

The nucleic acid encoding at least one MBS may comprise two or more MBSs, and it may comprise a set of one or more pairs of complementary sequences that can form a multiple-stranded (for example, double- or quadruple-stranded) structure in one consecutive sequence. An example of the nucleic acid is a nucleic acid comprising a pair of complementary sequences that form at least one double-stranded structure and at least one MBS on each of the ends of the pair of complementary sequences. Specifically, such a nucleic acid comprises a pair of complementary sequences that can form a stem between two MBSs. This stem corresponds to the above-mentioned second double-stranded structure. Alternatively, a sequence that forms a G-quadruplex may be comprised as a second multiple-stranded structure.

Furthermore, the nucleic acid may comprise two or more structural units comprising a pair of complementary sequences that can form a double-stranded structure between two MBSs. The multiple structural units comprised can be nested inside. A sequence comprising a pair of MBSs and a pair of complementary sequences that can form a double-stranded structure between the MBSs can be further comprised between a pair of complementary sequences that can form a double-stranded structure between two MBSs (#15 or #16 of FIG. 2). The comprised multiple MBS sequences may be the same or different.

When such a nucleic acid is inserted between an above-mentioned pair of complementary sequences, a sequence that has the structure of "MBS—sequence forming a second multiple-stranded structure—MBS" has been inserted between a pair of complementary sequences (stem I of FIG. 6) forming a first double-stranded structure to obtain a nucleic acid with such structure. Specifically, for example, the nucleic acid has a structure in which a sequence that has the structure of "MBS-pair of complementary sequences forming a second double-stranded structure (stem II of FIG. 6)—MBS" has been inserted. By transcribing them, a nucleic acid encoding an RNA complex in which two strands comprising MBSs are positioned between two multiple-stranded (for example, double-stranded) structures, can be obtained (FIG. 6). A nucleic acid comprising two multiple-stranded (for example, double-stranded) structures and a pair of single strands (each of which comprises an MBS) placed between them in opposite directions, is compact and shows sufficient miRNA-inhibiting activity.

A pair of complementary sequences that can form a double-stranded structure can be appropriately linked to an MBS via a linker or spacer. The length of the linker or spacer is as described herein. Furthermore, the complementary sequences may be linked via a linker or spacer, and when a double strand is formed, the linker or spacer becomes a loop and forms a step loop together with the double strand. The length of the loop may be adjusted appropriately, and the details are as described herein. Alternatively, when a quadruple strand is formed, a sequence that forms a G-quadruplex may be used appropriately.

A nucleic acid encoding MBS and a complementary strand thereof are synthesized, and the two are annealed (for example, the synthetic oligoDNA of FIG. 6B). When this is inserted into a restriction enzyme cleavage recognition site, the ends of the annealed double-stranded nucleic acid can be accordingly and appropriately made into the same structure as the ends produced by cleavage with the restriction enzyme.

The miRNA-inhibiting complexes of the present invention, or RNAs constituting the complexes (herein, the RNAs include naturally-occurring RNAs and derivatives), or vectors expressing the RNAs can be made into compositions for inhibiting miRNAs. Since compositions of the present invention can specifically and efficiently inhibit target miRNAs, they are useful for functional regulation of genes by inhibiting miRNAs. The compositions of the present invention can be combined with a desired pharmaceutically acceptable carrier or medium as necessary. Examples include desired solutions conventionally used for suspending nucleic acids, such as distilled water, phosphate-buffered saline solution (PBS), sodium chloride solution, Ringer's solution, and culture solution. Furthermore, plant oils, suspending agents, surfactants, stabilizers, biocides, and such may be included. Preservatives or other additives may also be added. Furthermore, the compositions of the present invention can be combined with carriers including organic substances such as biopolymers, inorganic substances such as hydroxyapatite, specifically, collagen matrix, polylactic acid polymer or copolymer, polyethylene glycol polymer or copolymer, chemical derivatives thereof, etc. The compositions of the present invention can be used as desired reagents or pharmaceutical compositions. Furthermore, the present invention provides use of the compositions of the present invention, miRNA-inhibiting complexes of the present invention, or RNAs constituting the complexes or vectors that express the RNAs, for inhibiting miRNAs. The present invention also provides miRNA inhibitors comprising any one of the above.

Introduction into cells can be carried out in vitro, ex vivo, or in vivo. When administered via cells, introduction into suitable culture cells, cells collected from the animal to be inoculated, or such, is carried out. Methods for introducing nucleic acids include the calcium phosphate coprecipitation method, lipofection, DEAE dextran method, method of directly injecting a DNA solution into a tissue using an injection needle or such, and introduction using a gene gun. Viral vectors are preferable since they can introduce genes into target cells at high efficiency. The dosage differs depending on the disease, body weight, age, gender, and symptoms of the patient, purpose of administration, form of administered composition, administration method, transgene, and such. However, the dosage may be adjusted appropriately depending on the animal to be administered, site of administration, number of doses, and such, and those skilled in the art can determine it appropriately. The route of administration can be suitably selected. Preferably, the targets of administration are mammals including human and nonhuman mammals. Specific examples include humans, non-human primates such as monkeys, rodents such as mice and rats, rabbits, goats, sheep, pigs, bovine, dogs, cats, and other mammals.

EXAMPLES

Herein below, the present invention will be specifically described with reference to the Examples, but it is not to be construed as being limited thereto. All references cited herein are incorporated into this description.

Example 1

1.1 Plasmid Construction

The oligonucleotides indicated in (1) below were annealed and cloned into NotI and SalI-cleaved pMXs-GIN (Haraguchi, T. et al. (2007) FEBS Lett, 581, 4949-4954) to produce pMXs-GIN-miR140-5pT and pMXs-GIN-miR140-3pT which are GFP reporters of miR-140-5p and miR-140-3p, respectively. The 0.7 kb BamHI-EcoRI fragment of pMXs-GFP (Kitamura, T. (1998) Int. J. Hematol., 67, 351-359) was inserted into the BamHI-EcoRI site of pcDNA3.1 (Invitrogen) to produce pcDNA3.1-GFP. The BamHI site and EcoRI site of pcDNA3.1-GFP were each filled in with a Klenow fragment. The 1.7 kb BglII-EcoRV fragment of this plasmid was inserted into the BglII-EcoRV site of pQCXIH (Clonteh) to produce pSSCG The 1.3 kb HindIII-XbaI fragment of pIRES1Hyg (Clontech) was inserted into the HindIII-XbaI site of pcDNA3.1 to produce pCMV-Hyg. The 2.1 kb NruI-ApaI fragment of pCMV-Hyg was inserted into the NruI-EcoRV site of pSSCG to produce pSSCH. To construct the miR-140-5p/140-3p expression retrovirus vector plasmid, the 0.5-kb mouse miR-140-5p/140-3p fragment was amplified by PCR from a mouse genome using the primer pairs shown in (1) below, and the PCR products were cloned into pCR2.1 (Invitrogen). The 0.5-kb BamHI-XhoI fragment of this plasmid was cloned into BamHI and SalI-digested pSSCH to produce pSSCH-miR140-5p/140-3p.
Oligonucleotides Used
(1) Primer Pairs for GFP Reporter Vector Construction For pMXs-GIN-miR140-3pT, the sense strand is 5'-GGC-CGCTCCGTGGTTCTACCCTGTGGTAGGG-3' (SEQ ID NO: 1) and the antisense strand is 5'-TCGACCCTACCA-CAGGGTAGAACCACGGAGC-3' (SEQ ID NO: 2). For pMXs-GIN-miR140-5pT, the sense strand is 5'-GGC-CGCTCTACCATAGGGTAAAACCACTGGGG-3' (SEQ ID NO: 3) and the antisense strand is 5'-TCGACCCCAGTG-GTTTTACCCTATGGTAGAGC-3' (SEQ ID NO: 4). For PCR-miR140-5p/140-3p, the sense strand is 5'-TGCT-TGCTGGTGGTGTAGTC-3' (SEQ ID NO: 5) and the antisense strand is 5'-ACCAACACCCACCCAATAGA-3' (SEQ ID NO: 6).

The oligo pair indicated in (2) below was annealed and cloned into pmU6, which had been digested with BbsI and EcoRI, to produce the pmU6-TuD-shuttle. To construct a miRNA-inhibiting RNA-expressing lentiviral vector plasmid, the series of oligonucleotide pairs indicated in (3) below were synthesized. Each oligo pair was annealed and cloned into BsmBI-digested pmU6-TuD-shuttle. Thereafter, each mU6-TuD RNA cassette was subcloned into a lentiviral vector plasmid (pLSP) as described above (Haraguchi, T. et al. (2007) FEBS Lett, 581, 4949-4954). These cassettes were also inserted into the BamHI-EcoRI site of pSL1180 (Pharmacia) to produce miRNA-inhibiting RNA-expressing plasmid vectors. The oligo pair indicated in (2) below was annealed and cloned into BbsI and EcoRI-digested pmU6 to produce pmU6-protoshuttle. To construct RNA inhibitory lentiviral vector expression plasmids, the series of oligonucleotide pairs shown in (4) below were synthesized. Each oligo pair (decoy RNA #1-12, 17-21) was annealed and cloned into pmU6 digested with BbsI and EcoRI. Each oligo pair (decoy RNA #13-16) was annealed and cloned into BsmBI-digested pmU6-protoshuttle. Each oligo pair (decoy RNA #22-26) was annealed and cloned into BsmBI-digested pmU6-TuD-shuttle. For construction of the mU6-decoy RNA #27 cassette, the oligo pairs indicated in (4) below were used as primers and templates for PCR, and the PCT products were cloned into pCR2.1. The 0.2-kb BsmBI fragment of this plasmid was cloned into BsmBI-digested pmU6-TuD-shuttle. Thereafter, each mU6-decoy RNA cassette was subcloned into a lentiviral vector plasmid (pLSP) as described above (Haraguchi, T. et al. (2007) FEBS Lett, 581, 4949-4954).
Oligonucleotides Used (2) Primer Pairs for Construction of Shuttle Vectors of RNAs of the Present Invention For pmU6-TuD-shuttle, 5'-TTTGACGGCGCTAGGAT-CATCGGAGACGGTACCGTCTCGATGATC-CTAGCGCCGTC TTTTTTG-3' (SEQ ID NO: 7) was used as the sense strand and 5'-AATTCAAAAAAGACG-GCGCTAGGATCATCGAGACGGTAC-CGTCTCCGATGATCCTA GCGCCGT-3' (SEQ ID NO: 8) was used as the antisense strand; and for pmU6-protoshuttle, 5'-TTTGACGGCGCTAGGATCATCGGAGACG-GTACCGTCTCCGATGATCCTAGCGCCGT CTTTTTTG-3' (SEQ ID NO: 9) was used as the sense strand and 5'-AAT-TCAAAAAAGACGGCGCTAGGATCATCGGAGACGGT ACCGTCTCCGATGATCCT AGCGCCGT-3' (SEQ ID NO: 10) was used as the antisense strand.

(3) Primer Pairs for Construction of Expression Vectors of RNAs of the Present Invention For TuD-miR-140-5p-4ntin, 5'-CATCAACCTACCAT-AGGGTCATCAAAACCACTGCAAGTAT-TCTGGTCACAGAATAC AACCTACCATAGGGTCAT-CAAAACCACTGCAAG-3' (SEQ ID NO: 11) was used as the sense strand and 5'-TCATCTTGCAGTGGTTTTGAT-GACCCTATGGTAGGTTGTATTCTGTGACCAGAATAC TTGCAGTGGTTTTGATGACCCTATGGTAGGTT-3' (SEQ ID NO: 12) was used as the antisense strand. For TuD-miR-140-3p-4ntin, 5'-CATCAACTCCGTGGT-TCTAATCTCCCTGTGGTACAAGTAT-TCTGGTCACAGAATACA ACTCCGTGGTTCTAATCTCCCTGTGGTACAAG-3' (SEQ ID NO: 13) was used as the sense strand and 5'-TCATCTTGTACCACAGGGAGATTAGAAC-CACGGAGTTGTATTCTGTGACCAGAATA CTTGTAC-CACAGGGAGATTAGAACCACGGAGTT-3' (SEQ ID NO: 14) was used as the antisense strand. For TuD RNA-miR140-3p-pf, 5'-CATCAACTCCGTGGTTCTACCCTGTGG-TACAAGTATTCTGGTCACAGAATACAACT CCGTG-GTTCTACCCTGTGGTACAA -3' (SEQ ID NO: 15) was used as the sense strand and 5'-CATCTTGTACCACAGGG-TAGAACCACGGAGTTGTATTCTGTGAC-CAGAATACTTGT ACCACAGGGTAGAACCACG-GAGTT-3' (SEQ ID NO: 16) was used as the antisense strand. For TuD RNA-miR21-4ntin, 5'-CATCAACTCAACAT-CAGTCAATGTGATAAGCTACAAGTAT-TCTGGTCACAGAATAC AACTCAACATCAGTCAAT-GTGATAAGCTACAAG-3' (SEQ ID NO: 17) was used as the sense strand and 5'-TCATCTTGTAGCTTATCACAT-TGACTGATGTTGAGTTGTATTCTGTGAC-CAGAATACT TGTAGCTTATCACATTGACTGATGT-TGAGTT-3' (SEQ ID NO: 18) was used as the antisense strand. For TuD RNA-miR21-pf, 5'-CATCAACTCAACAT-CAGTCTGATAAGCTACAAGTATTCTGGT-CACAGAATACAACT CAACATCAGTCTGATAAGCTA-CAAG-3' (SEQ ID NO: 19) was used as the sense strand and 5'-TCATCTTGTAGCTTATCAGACTGATGT-TGAGTTGTATTCTGTGACCAGAATACTTGT AGCT-TATCAGACTGATGTTGAGTT-3' (SEQ ID NO: 20) was used as the antisense strand. For TuD RNA-NC, 5'-CATCAA-CAAGCCACAACGAATCTCTATATCAT-CAAGTATTCTGGTCACAGAATACAA CAAGCCA-CAACGAATCTCTATATCATCAAG-3' (SEQ ID NO: 21) was used as the sense strand and 5'-TCATCTTGATGATATA-GAGATTCGTTGTGGCTTGTTGTATTCT-GTGACCAGAATACTT GATGATATAGAGATTCGT-TGTGGCTTGTT-3' (SEQ ID NO: 22) was used as the antisense strand.

(4) Primer Pairs for Construction of Decoy RNA Expression Vectors

For decoy RNA #1, 5'-TTTGACGGCGCTGGATGCT-TGGATCCGTGGTTCTACCCTGTGGTAAG-GAAGCATCC AGCGCCGTCTTTTTTG-3' (SEQ ID NO: 23) was used as the sense strand and 5'-AATTCAAAAAA-GACGGCGCTGGATGCTTCCTTACCA-CAGGGTAGAACCACGGATC CAAGCATCCAGCGC-CGT-3' (SEQ ID NO: 24) was used as the antisense strand.

For decoy RNA #2, 5'-TTTGACGGCGCTAGGATGCT-TGGATCCGTGGTTCTACCCTGTGGTAAGGAAGCATC CTAGCGCCGTCTTTTTTG-3' (SEQ ID NO: 25) was used as the sense strand and 5'-AATTCAAAAAAGACG-GCGCTAGGATGCTTCCTTACCACAGGG-TAGAACCACGGAT CCAAGCATCCTAGCGCCGT-3' (SEQ ID NO: 26) was used as the antisense strand.

For decoy RNA #3, 5'-TTTGACAGCGCTCTACGAT-GAAGGCTCCGTGGTTCTACCCTGTGG-TAAGGTTCATC GTAGAGCGCTGTCTTTTTTG-3' (SEQ ID NO: 27) was used as the sense strand and 5'-AAT-TCAAAAAAGACAGCGCTCTACGATGAAC-CTTACCACAGGGTAGAACCACGGA GCCTTCATCG-TAGAGCGCTGT-3' (SEQ ID NO: 28) was used as the antisense strand.

For decoy RNA #4, 5'-TTTGACAGCGCTCTACGATG-CAAGGCTCCGTGGTTCTACCCTGTGG-TAAGGTTGCA TCGTAGAGCGCTGTCTTTTTTG-3' (SEQ ID NO: 29) was used as the sense strand and 5'-AAT-TCAAAAAAGACAGCGCTCTACGATG-CAACCTTACCACAGGGTAGAACCACGG AGCCTTG-CATCGTAGAGCGCTGT-3' (SEQ ID NO: 30) was used as the antisense strand.

For decoy RNA #5, 5'-TTTGACAGCGCTCGCAGGAT-GCTTGGCTCCGTGGTTCTACCCTGTGG-TAAGGAAGC ATCCTGCGAGCGCTGTCTTTTTTG-3' (SEQ ID NO: 31) was used as the sense strand and 5'-AAT-TCAAAAAAGACAGCGCTCGCAGGATGCT-TCCTTACCACAGGGTAGAACCACG GAGCCAAG-CATCCTGCGAGCGCTGT-3' (SEQ ID NO: 32) was used as the antisense strand.

For decoy RNA #6, 5'-TTTGACAGCGCTCAAAGCAG-GATGCTTGGCTCCGTGGTTCTACCCTGTGGTAAGGA AGCATCTGCTTTGAGCGCTGTCTTTTTTG-3' (SEQ ID NO: 33) was used as the sense strand and 5'-AAT-TCAAAAAAGACAGCGCTCAAAGCAGGAT-GCTTCCTTACCACAGGGTAGAACC ACGGAGC-CAAGCATCCTGCTTTGAGCGCTGT-3' (SEQ ID NO: 34) was used as the antisense strand.

For decoy RNA #10, 5'-TTTGACGGCGCTAGGAT-CATCTCCGTGGTTCTACCCTGTGGTAG-TATTCTGGTCACA GAATACGATGATCCTAGCGC-CGTCTTTTTTG-3' (SEQ ID NO: 35) was used as the sense strand and 5'-AATTCAAAAAAGACGGCGCTAGGAT-CATCGTATTCTGTGACCAGAATACTACCACA GGG-TAGAACCACGGAGATGATCCTAGCGCCGT-3' (SEQ ID NO: 36) was used as the antisense strand.

For decoy RNA #11, 5'-TTTGACGGCGCTAGGAT-CATCGTATTCTGGTCACAGAATACTC-CGTGGTTCTACCCT GTGGTATCTTCTCTAAC-GAGAGAAGAGATGATCCTAGCGCCGTCTTTTTTG-3' (SEQ ID NO: 37) was used as the sense strand and 5'-AAT-TCAAAAAAGACGGCGCTAGGAT-CATCTCTTCTCTCGTTAGAGAAGATACCACA GGG-TAGAACCACGGAGTATTCTGTGACCAGAATACGATG ATCCTAGCGCCGT-3' (SEQ ID NO: 38) was used as the antisense strand.

For decoy RNA #12, 5'-TTTGACGGCGCTAGGAT-CATCTCCGTGGTTCTACCCTGTGGTAG-TATTCTGGTCACA GAATACTCCGTGGTTCTACCCT-GTGGTAGATGATCCTAGCGCCGTCTTTTTTG-3' (SEQ ID NO: 39) was used as the sense strand and 5'-AAT-TCAAAAAAGACGGCGCTAGGATCATC-TACCACAGGGTAGAACCACGGAGTAT TCTGTGAC-CAGAATACTACCACAGGGTAGAACCACGGAGATGAT CCTAGCGCCGT-3' (SEQ ID NO: 40) was used as the antisense strand.

For decoy RNA #13, 5'-CATCAACTCCGTGGTTCTAC-CCTGTGGTACAAGTATTCTGGTCACAGAATACAACT CCGTGGTTCTACCCTGTGGTACAA-3' (SEQ ID NO: 41) was used as the sense strand and 5'-CATCTTGTACCA-CAGGGTAGAACCACGGAGTTGTATTCT-GTGACCAGAATACTTGT ACCACAGGGTAGAAC-CACGGAGTT-3' (SEQ ID NO: 42) was used as the antisense strand.

For decoy RNA #14, 5'-CATCTCCGTGGTTCTACCCT-GTGGTAGTATTCTGAGATCCGTGGTTC-TACCCTGTGG TAAGACAGAATACTCCGTGGTTC-TACCCTGTGGTA-3' (SEQ ID NO: 43) was used as the sense strand and 5'-CATCTACCACAGGGTAGAACCACG-GAGTATTCTGTCTTACCACAGGGTAGAACCAC GGATCTCAGAATACTACCACAGGGTA-GAACCACGGA-3' (SEQ ID NO: 44) was used as the antisense strand.

For decoy RNA #15, 5'-CATCTCCGTGGTTCTACCCT-GTGGTAGTATTCTGTCCGTGGTTCTAC-CCTGTGGTAG TATTCTGGTCACAGAATACTCCGTG-GTTCTACCCTGTGGTACAGAATACTCCGTGGTTC TACCCTGTGGTA-3' (SEQ ID NO: 45) was used as the sense strand and 5'-CATCTACCACAGGGTAGAACCACG-GAGTATTCTGTACCACAGGGTAGAACCACGG AGTATTCTGTGACCAGAATACTACCA-CAGGGTAGAACCACGGACAGAATACTACCAC AGGGTAGAACCACGGA-3' (SEQ ID NO: 46) was used as the antisense strand.

For decoy RNA #16, 5'-CATCTCCGTGGTTCTACCCT-GTGGTAGTATTCTGTCCGTGGTTCTAC-CCTGTGGTAG TATTCTGAGATCCGTGGTTCTACCCT-GTGGTAAGACAGAATACTCCGTGGTTCTACCCT GTGGTACAGAATACTCCGTGGTTCTAC-CCTGTGGTA-3' (SEQ ID NO: 47) was used as the sense strand and 5'-CATCTACCACAGGGTAGAACCACGGAG-TATTCTGTACCACAGGGTAGAACCACGG AGTATTCT-GTCTTACCACAGGGTAGAACCACG-GATCTCAGAATACTACCACAGGGTAG AACCACGGACAGAATACTACCACAGGG-TAGAACCACGGA-3' (SEQ ID NO: 48) was used as the antisense strand.

For decoy RNA #17, 5'-TTTGACGGCGCTAGGATGCT-TGGATCCGTGGTTCTAACCCTGTGGTAAGGAAGCAT CCTAGCGCCGTCTTTTTTG-3' (SEQ ID NO: 49) was used as the sense strand and 5'-AATTCAAAAAAGACG-GCGCTAGGATGCTTCCTTACCACAGGGT-TAGAACCACGGA TCCAAGCATCCTAGCGCCGT-3' (SEQ ID NO: 50) was used as the antisense strand.

For decoy RNA #18, 5'-TTTGACGGCGCTAGGATGCT-TGGATCCGTGGTTCTAATCCCTGTGG-TAAGGAAGCA TCCTAGCGCCGTCTTTTTTG-3' (SEQ ID NO: 51) was used as the sense strand and 5'-AAT-TCAAAAAAGACGGCGCTAGGATGCTTC-CTTACCACAGGGATTAGAACCACGG ATCCAAG-CATCCTAGCGCCGT-3' (SEQ ID NO: 52) was used as the antisense strand.

For decoy RNA #19, 5'-TTTGACGGCGCTAGGATGCT-TGGATCCGTGGTTCTAACTCCCTGTGG-TAAGGAAGC ATCCTAGCGCCGTCTTTTTTG-3' (SEQ ID NO: 53) was used as the sense strand and 5'-AAT-TCAAAAAAGACGGCGCTAGGATGCTTC-CTTACCACAGGGAGTTAGAACCACG GATCCAAG-CATCCTAGCGCCGT-3' (SEQ ID NO: 54) was used as the antisense strand.

For decoy RNA #20, 5'-TTTGACGGCGCTAGGATGCT-TGGATCCGTGGTTCTAATCTCCCTGTGGTAAGGAAG CATCCTAGCGCCGTCTTTTTTG-3' (SEQ ID NO: 55) was used as the sense strand and 5'-AATTCAAAAAAGACG-GCGCTAGGATGCTTCCTTACCACAGG-GAGATTAGAACCAC GGATCCAAGCATCCTAGCGC-CGT-3' (SEQ ID NO: 56) was used as the antisense strand.

For decoy RNA #21, 5'-TTTGACGGCGCTAGGATGCT-TCCATCCCAGTACACATTTAAATCTGTG-GTACCAAGC ATCCTAGCGCCGTCTTTTTTG-3' (SEQ ID NO: 57) was used as the sense strand and 5'-AAT-TCAAAAAAGACGGCGCTAGGATGCTTGG-TACCACAGATTTAAATGTGTACTGG GATGGAAG-CATCCTAGCGCCGT-3' (SEQ ID NO: 58) was used as the antisense strand.

For decoy RNA #22, 5'-CATCCTCCGTGGT-TCTAATCTCCCTGTGGTACGTATTCTG-GTCACAGAATACCTCCG TGGTTCTAATCTCCCT-GTGGTACG-3' (SEQ ID NO: 59) was used as the sense strand and 5'-TCATCGTACCACAGGGAGATTAGAAC-CACGGAGGTATTCTGTGACCAGAATACGTA CCA-CAGGGAGATTAGAACCACGGAG-3' (SEQ ID NO: 60) was used as the antisense strand.

For decoy RNA #23, 5'-CATCCTCCGTGGT-TCTAATCTCCCTGTGGTACCGTATTCTG-GTCACAGAATACCCT CCGTGGTTCTAATCTCCCT-GTGGTACCG-3' (SEQ ID NO: 61) was used as the sense strand and 5'-TCATCGGTACCACAGGGAGATTAGAAC-CACGGAGGGTATTCTGTGACCAGAATACG GTACCA-CAGGGAGATTAGAACCACGGAGG-3' (SEQ ID NO: 62) was used as the antisense strand.

For decoy RNA #24, 5'-CATCAACTCCGTGGT-TCTAATCTCCCTGTGGTACAAGTAT-TCTGGTCACAGAATACA ACTCCGTGGT-TCTAATCTCCCTGTGGTACAAG-3' (SEQ ID NO: 63) was used as the sense strand and 5'-TCATCTTGTACCA-CAGGGAGATTAGAACCACGGAGTTGTAT-TCTGTGACCAGAATA CTTGTACCACAGGGAGATTA-GAACCACGGAGTT-3' (SEQ ID NO: 64) was used as the antisense strand.

For decoy RNA #25, 5'-CATCACCCTCCGTGGT-TCTAATCTCCCTGTGGTACCCAGTAT-TCTGGTCACAGAATA CACCCTCCGTGGT-TCTAATCTCCCTGTGGTACCCAG-3' (SEQ ID NO: 65) was used as the sense strand and 5'-TCATCTGGGTACCA-CAGGGAGATTAGAACCACGGAGGGTG-TATTCTGTGACCAGA ATACTGGGTACCACAGG-GAGATTAGAACCACGGAGGGT-3' (SEQ ID NO: 66) was used as the antisense strand.

For decoy RNA #26, 5'-CATCAACCCTCCGTGGT-TCTAATCTCCCTGTGGTACCCAAGTAT-TCTGGTCACAGAA TACAACCCTCCGTGGT-TCTAATCTCCCTGTGGTACCCAAG-3' (SEQ ID NO: 67) was used as the sense strand and 5'-TCATCTTGGGTACCA-CAGGGAGATTAGAACCACGGAGGGTTG-TATTCTGTGACCAG AATACTTGGGTACCACAGG-GAGATTAGAACCACGGAGGGTT-3' (SEQ ID NO: 68) was used as the antisense strand.

For decoy RNA #27, 5'-CGTCTCACATCAACTCCGTG-GTTCTAATCTCCCTGTGGTACAAGCGACAAGAACTCCGTGGTTCTAATCTCCCTGTGGTACAAG-TATTCTGAACTCCGTGGTTCTAATCTCCCTG TGGT-3' (SEQ ID NO: 69) was used as the sense strand and 5'-CGTCT-CATCATCTTGTACCACAGGGAGATTA-GAACCACGGAGTTGCGACAAGTTGT ACCACAGG-GAGATTAGAACCACGGAGTTGTATTCTGTTGTACCA CAGGGAGATTAGA ACCACGG-3' (SEQ ID NO: 70) was used as the antisense strand.

To construct the microRNA CMV sponge miR21-expressing vector plasmid, the oligo pair indicated in (5) below was used as PCR primers and templates, and the PCR products were cloned into pCR2.1. The 0.2-kb XhoI-AgeI fragment of this plasmid was cloned into XhoI and AgeI-digested pLenti6N5-GW/lacZ (Invitrogen) to produce pLenti6/CMV-sponge-miR21/lacZ. The 0.3-kb XbaI-ApaI fragment of pCS2-Venus was cloned into the XbaI-ApaI site of pSL1180 to produce pSL1180-polyA. The 3.9-kb HindIII-AgeI fragment of pLenti6/CMV-sponge-miR21/lacZ was cloned into the HindIII-AgeI site of pSL1180-polyA to produce pSL1180-CMVsponge21. To construct the Antagomir21 expression vector plasmid (Scherr, M. et al. (2007) Nucleic Acids Res, 35(22):e149), the oligo pair indicated in (5) below was used as PCR primers, and pSilencer 3.1-H1 hygro (Ambion) was used as the template. The PCR products were cloned into pCR2.1, and the 0.2-kb BglII-EcoRI fragment of this plasmid was cloned into the BamHI-EcoRI fragment of pSL1180 to produce pSL1180-H1Antagomir21. To construct the miR-21 eraser-expressing vector plasmid (Sayed, D. et al. (2008) Mol Biol Cell, 19(8):3272-82), the oligo pair indicated in (5) below was used as PCR primers, and pmU6 was used as the template. PCR products were digested using BamHI and EcoRI and cloned into the BamHI-EcoRI fragment of pSL1180 to produce pSL1180-miR-21 eraser.

To construct the luciferase reporter plasmid, the 0.8-kb KpnI-HindIII fragment of pGL4.74 (Promega) was cloned into KpnI and HindIII-digested pGL4.12 (Promega) to produce pTK4.12. The oligonucleotide pair indicated in (6) below was annealed and ligated to the 4.9-kb EcoRI-XbaI fragment of pTK4.12 to produce pTK4.12C.P. The oligonucleotide pair indicated in (6) below was annealed and cloned into XbaI and FseI-digested pGL4.74 to produce pGL4.74-miR21T.

Oligonucleotides Used (5) Primer Pairs Used for Construction of the AntagomiR, miNRA Eraser, and CMV Sponge Expression Vectors For CMVsponge21, 5'-CTCGAGTAACTCAACATCAG-GACATAAGCTAAGTCTCAACATCAGGACATAAGCTA TCAGTCAACATCAGGACATAAGCTACT-GATCAACATCAGGACATAAGCTA-3' (SEQ ID NO: 71) was used as the sense strand and 5'-ACCGGTTAGCTTAT-GTCCTGATGTTGACCGATAGCTTATGTC-CTGATGTTGACAGTT AGCTTATGTCCTGATGT-TGAGTTCTAGCTTATGTCCTGATGTTGATCAG-3' (SEQ ID NO: 72) was used as the antisense strand. For AntagomiR21, 5'-AGATCTAATTCATATTTGCAT-GTCGCT-3' (SEQ ID NO: 73) was used as the forward primer and 5'-GAATTCAAAAAATAGCTTATGTCCTGAT-GTTGAGGATCCGAGTGGTCTCATACAGA ACTTATA-3' (SEQ ID NO: 74) was used as the reverse primer. For miR-21 eraser, 5'-CGGGATCCATCCGACGCCGC-CATCTCTA-3' (SEQ ID NO: 133) was used as the forward primer and 5'-GGAATTCAAAAAATAGCTTATCAGACT-GATGTTGATAGCTTATCAGACTGATGTTGA AAA-CAAGGCTTTTCTCCAA-3' (SEQ ID NO: 134) was used as the reverse primer.

(6) Primer Pairs Used for Construction of the Luciferase Reporter Vector

For the insert of pTK4.12C.P-, 5'-AATTAATAATGACTC-GAGT-3' (SEQ ID NO: 75) was used as the sense strand and 5'-CTAGACTCGAGTCATTATT-3' (SEQ ID NO: 76) was used as the antisense strand. For pGL4.74-miR21T, 5'-AAT-TCTCAACATCAGTCTGATAAGCTAC-3' (SEQ ID NO: 77) was used as the sense strand and 5'-TCGAGTAGGCT-TATCAGACTGATGTTGAG-3' (SEQ ID NO: 78) was used as the antisense strand.

1.2 Cell Culture and Construction of Stable Cell Lines

HeLaS3 cells (Puck et al., J. Exp. Med. 103: 273-284 (1956)), PA-1 cells (Giovanella, B C et al., In Vitro Cell Dev. Biol., 10: 382, 1974, 10:382; Giovanella, B. C. et al., J Natl Cancer Inst, 1974, 52:921-30), HCT-116 cells (Cancer Res 1981;41:1751; J Nat Cancer Inst 1982; 69:767), SW480 cells (Leibovitz et al., Cancer Res. 36: 4562-4569 (1976)), HT29 cells (Fogh & Trempe in Human Tumor Cells in Vitro (ed. Fogh J.), Plenum Press, New York, 1975, pp. 115-159), TIG-3/E/TERT cells (Akagi T et al., Proc Natl Acad Sci USA, 100, 13567-13572. (2003)), and 3Y1 cells (Ushijima T et al., Jpn. J. Cancer Res. 85:455-458, 1994; Kimura G et al., Int. J. Cancer, 15: 694-706, 1975) were cultured at 37° C. in DMEM containing 10% fetal bovine serum (FBS). HeLaS3 cells were seeded at $1 \times 10^5$ cells per well in a 6-well plate, and 24 hours later, the pMXs-GIN, pMXs-GIN-miR140-5pT, and pMXs-GIN-miR140-3pT viral stocks ($<1 \times 10^4$ TU)) were each introduced in the presence of 8 μg/mL of polybrene. Twenty-four hours after transduction, selection was carried out with G418 (1 mg/mL). After two weeks of selection, G418 was removed from the medium. HeLaS3 cells carrying the miR-140-5p reporter or miR-140-3p reporter were plated at $1 \times 10^5$ cells per well in a 6-well plate, and 24 hours later, the pSSCH-miR140-5p/140-3p viral stock ($<1 \times 10^4$ TU)) was introduced in the presence of 8 μg/mL of polybrene. Twenty-four hours after transduction, selection was carried out with hygromycin (0.5 mg/mL). After two weeks of selection, hygromycin was removed from the medium.

1.3 Viral Transduction and FACS Analysis

HeLaS3 cells carrying both the miR-140-5p reporter and miR140-5p/140-3p vector, and HeLaS3 cells carrying both the miR-140-3p reporter and miR140-5p/140-3p vector were seeded in DMEM containing 10% fetal bovine serum (FCS) at $1 \times 10^5$ cells per well in a 6-well plate, and 24 hours later, the miRNA-inhibiting RNA-expressing viral stock ($2 \times 10^5$ TU) or decoy RNA-expressing viral stock ($2 \times 10^5$ TU) was each introduced in the presence of 8 μg/mL of polybrene. Furthermore, 24 hours later, the medium was replaced with DMEM containing 10% fetal bovine serum (FBS) and puromycin (1 μg/mL). After seven days of selection, puromycin was removed from the medium. The GFP expression level was measured using FACS Calibur (BD).

1.4 RNA Isolation, miR-RT-PCR

Total RNAs were prepared using the mirVana™ miRNA Isolation Kit (Ambion) from HeLaS3 cells transfected with a miRNA-inhibiting RNA-expressing lentiviral vector and HCT-116 cells transfected with a miRNA-inhibiting RNA-expressing vector, which carry both the miR-140-5p reporter and miR140-5p/140-3p vector. Expression of mature miRNA was determined by miR-qRT-PCR using miRNA-specific looped RT primers and a TaqMan probe following recommendations made by the manufacturer (Applied Biosystems, Foster City, USA). U6 snRNA was used as the internal control. PCR was performed in triplicate using 7300 Real Time PCR System (Applied Biosystems).

1.5 Luciferase Assay

In a 24-well plate, PA-1 cells, HCT-116 cells, SW480 cells, HT29 cells, TIG-3/E/TERT cells, and 3Y1 cells were seeded the day before introduction at $1\times10^5$ cells per well, $1.7\times10^5$ cells per well, $3.5\times10^5$ cells per well, $3.0\times10^5$ cells per well, $7.0\times10^4$ cells per well, and $1.2\times10^5$ cells per well, respectively, in DMEM containing 10% fetal bovine serum (FBS); and Lipofectamine 2000 (Invitrogen) and 10 ng of pTK4.12C.P- (Firefly luciferase plasmid), 100 ng of RLuc target reporter plasmid, and 500 ng of miRNA-inhibiting RNA expression plasmid were transfected in triplicate. A locked nucleic acid (LNA/DNA) antisense oligonucleotide was cotransfected at 50 nM. The LNA/DNA antisense oligonucleotide was synthesized at ThermoELECTRON Co., and contains locked nucleic acids at eight nucleotides positioned continuously in the center (Naguibneva, I. et al. (2006) Biomed Pharmacother, 60, 633-638). LNA/DNA antisense oligonucleotides have the sequences indicated in the following (7). All assays were performed 48 hours after transfection using GLOMAX™ (Promega) by dual luciferase assay (Promega).

Oligonucleotides Used (7) The Sequences of LNA/DNA Antisense Oligos

For LNA-miR21, 5'-TCAACAT CAGTCTGATAAGCTA-3' (SEQ ID NO: 79) was used. For LNA-NC, 5'-CATTAATGTCGGACAACTCAAT-3' (SEQ ID NO: 80) was used. The LNA is indicated by underline.

1.6 Western Blotting

Total protein was extracted from cells using 1.5×SDS Buffer, and protein concentrations were measured by using a Bio-Rad protein assay kit. The protein extract was separated on 10% SDS-PAGE and transferred to a PVDF-membrane (Milipore). Immunoblotting was performed by incubating the membrane with an anti-PDCD4 (ab51495, Abcam) antibody and an anti-Actin (612656, BD transduction) antibody at room temperature for one hour. After washing three times with Tween 20-containing phosphate-buffered saline, the membranes were incubated with horseradish peroxidase-conjugated secondary antibodies at room temperature for one hour. The signals were detected using an ECL reagent (Amersham).

1.7 Measurement of Cell Growth and Apoptosis Activity

PA-1 cells were seeded in DMEM containing 10% fetal bovine serum (FBS) at $1\times10^4$ cells per well in a 48-well plate, and 24 hours later, TuD-miR21-4ntin and TuD-NC-expressing lentiviral stocks ($1\times10^5$ TU)) were each introduced in the presence of 8 µg/mL of polybrene. The medium was replaced 24 hours after transduction. The metabolic activity of cells immediately before transduction and 24, 48, 72, and 96 hours after transduction were measured using GLOMAX™ by CellTiter-Glo™ (Promega) to measure cell growth.

PA-1 cells were seeded in DMEM containing 10% fetal bovine serum (FBS) at $3\times10^3$ cells per well in a 48-well plate, and 18 hours later, TuD-miR21-4ntin and TuD-NC-expressing lentiviral stocks ($3\times10^4$ TU)) were each introduced in the presence of 8 µg/mL of polybrene. The medium was replaced 24 hours after transduction. Furthermore, 72 hours after transduction, the activities of caspase 3 and 7 were measured by Caspase-Glo™ 3/7 (Promega) using GLOMAX™.

1.8 Northern Blotting

Nuclear fractions and cytoplasmic fractions from noninfected HeLaS3 cells or HeLaS3 cells expressing TuD-miR-140-3p-4ntin or TuD-miR-140-5p-4ntin were separated and collected fourteen days after vector introduction. Cells from fourteen 10-cm dishes were used. Each dish was washed twice with cold PBS. 2 mL of cold PBS was further added to the dish, the cells were collected using a scraper, and centrifugation was carried out at 4° C. for five minutes at 1500 rpm. The cell precipitates were suspended in NP40 lysis Buffer (10 mM Tris-HCl (pH 7.4), 10 mM NaCl, 3 mM $MgCl_2$, 0.5% Nonidet P-40), left to stand on ice for ten minutes, and then centrifuged at 4° C. for five minutes at 1400 rpm. The supernatant was collected as the cytoplasmic fraction and cytoplasmic RNAs were collected using ISOGEN (Wako Pure Chemical Industries, Osaka, Japan). Furthermore, the precipitate which is the nuclear fraction was washed twice with 4 mL of NP40 lysis buffer. Using the mirVana™ miRNA Isolation Kit (Ambion, Austin, Tex.), only RNAs that are smaller than 200 bp were purified from the cytoplasmic RNAs and the precipitate (which is the nuclear fraction). For comparison, an equivalent amount of 5% of the RNA collected from the same number of original cells was used for Northern blot analysis.

Small RNAs were separated on 18% denaturing acrylamide gel. In this case, electrophoresis was carried out in an 80° C. incubator. Then they were transferred to Hybond-XL membranes (Amersham BioSciences) and crosslinked using 60 $mJ/cm^2$ UV. DNA probes were labeled at the 5' end with [$\gamma$-$^{32}$P] ATP using T4 polynucleotide kinase (TAKARA). Hybridization was carried out at 37° C. using Ultrahyb-Oligo buffer (Ambion). The membranes were washed using 2×SSC, 0.5% SDS buffer. RI signals were measured using FLA-5100 (FUJI FILM). Furthermore, deprobing was performed using an aqueous 0.5% SDS solution.

Oligonucleotides Used (8) Sequences of DNA Probes Used for Northern Blotting

5'-GTTGATGATCCTAGCGCCGTC-3' (SEQ ID NO: 135) was used as the probe for detecting a miRNA-inhibiting RNA. 5'-TCAACATCAGTCTGATAAGCTA-3' (SEQ ID NO: 136) was used as the probe for detecting miR-21. 5'-GCAGTGGGGGGTTGTATACCAAC-3' (SEQ ID NO: 137) was used as the probe for detecting Y4 scRNA. 5'-GTGATGGAAGCATAACCTGTCTC-3' (SEQ ID NO: 138) was used as the probe for detecting ACA1 snoRNA.

Example 2

Highly Sensitive Assay System for Detecting miR-140-3p Activity

HeLaS3 which endogenously expresses only a small amount of miR-140-3p and miR-140-5p (Landgraf, P. et al. (2007) Cell, 129, 1401-1414) was used to construct a very highly sensitive assay system for miR-140-3p activity. For this purpose, retrovirus-based GFP reporters, having a 21-bp insertion completely complementary to mature miR-140-3p immediately downstream of the GFP gene, were constructed (miR-140-3p reporter) (FIG. 15A). They were introduced into HeLaS3 cells, and mixed cell populations stably expressing GFP were established.

Figure 16:
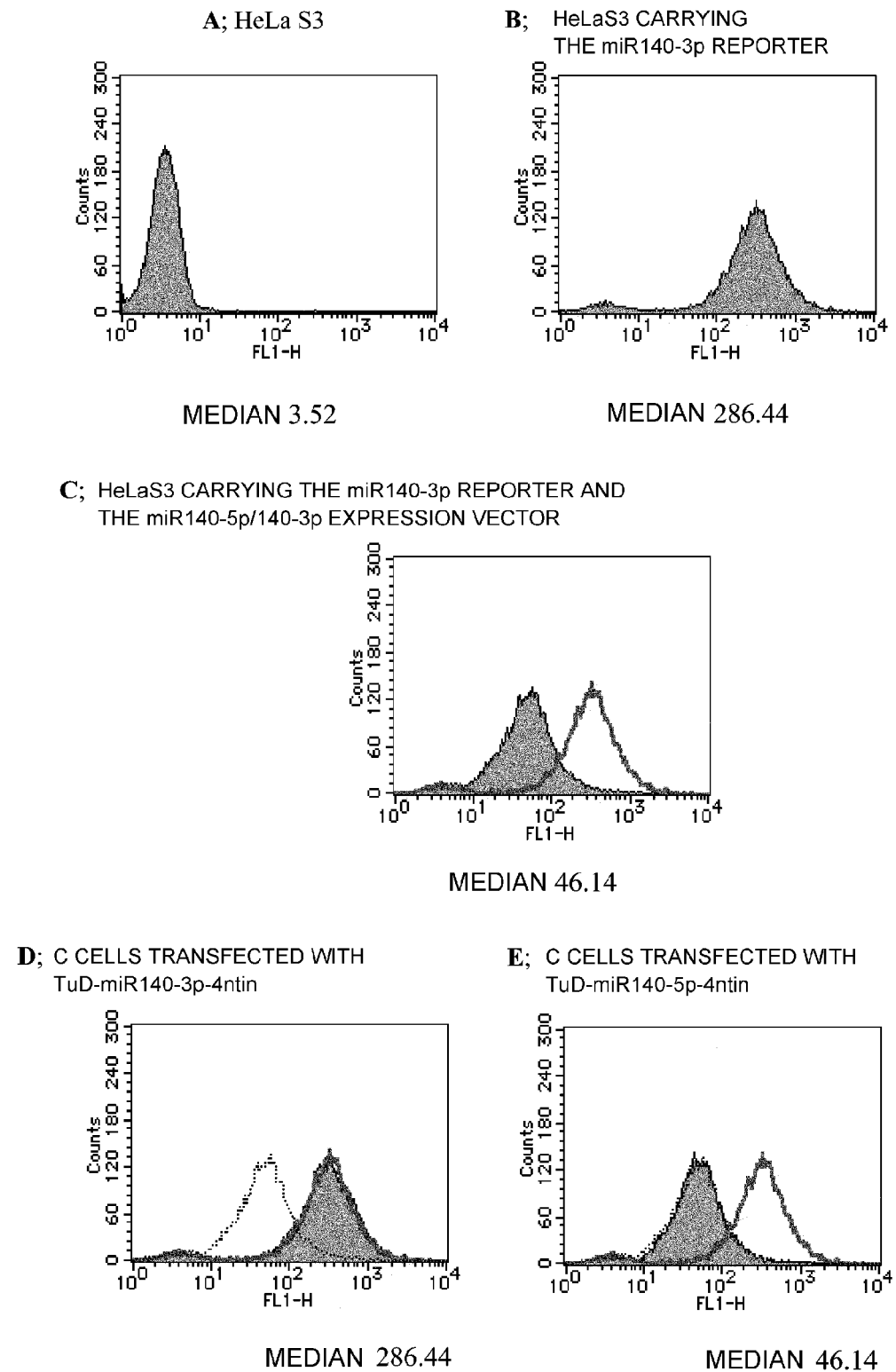
FIG. 16 shows the establishment of a highly sensitive assay system for miR140-3p activity, and the effect of introducing miRNA-inhibiting RNAs (Panels A to E).

Next, a retrovirus vector that drives RNAs comprising the whole pre-miRNA containing both miR140-5p and miR140-3p from a Pol II promoter was constructed (miR140-5p/140-3p vector) (FIG. 15C). This was introduced into HeLaS3 cells carrying the miR-140-3p reporter to establish mixed cell populations. Compared to non-introduced HeLaS3 cells that have the miR-140-3p reporter, the level of GFP expression was less than 20% (FIGS. 16A, B, and C).

Example 3

Design and Effectiveness of Prototype Decoy RNA

As prototypes of decoy RNA, decoy RNAs having a simple secondary structure which are expected to expose an RNA sequence completely complementary to the RNA sequence of mature miR-140-3p were designed. These prototype decoy RNAs (FIG. 1A) formed a stem-loop structure, and that loop was composed of an MBS completely complementary to mature miR-140-3p and 3-nucleotide linkers present at both ends. To stably express these decoy RNAs in cells, the use of a lentiviral vector loaded with a cassette for short RNA expression which is driven by a polymerase III promoter (mU6) present in both LTRs after integration was selected (FIG. 15D). Since the RNA transcription products by RNA polymerase III are designed to end with UU (or UUUU), RNA decoys are expected to have a 3'-protruding end of two (to four) nucleotides in the stem (FIG. 1A).

The synthesized decoy RNAs are supposed to be transported from the cell nucleus to the cytoplasm, and there they will act on RISC containing the corresponding miRNA miR-140-3p. So far, nuclear transport of small RNAs having a stem-loop structure has been studied in detail, and the stem length has been shown to be important for the efficiency of Exp-5-mediated extranuclear transport (Zeng, Y. and Cullen, B. R. (2004) Nucleic Acids Res, 32, 4776-4785). The binding activity of hairpin RNA to Exp-5 has been shown to decrease dramatically when the length of the stem sequence becomes shorter than 16 bp; therefore, the stem lengths of the prototype RNA decoys were changed to 17 bp-24 bp (decoy #1 to #6, FIG. 1B). shRNA that targets the coding region of the bacteriophage gene Cre recombinase (shCre) was used as a negative control (NC) for the decoy RNA vector. A prototype RNA decoy having an 18-bp stem showed a slightly higher inhibitory effect than others, and since dsRNA exceeding 20 bp may become potential targets for Dicer-mediated cleavage in the cytoplasm, the 18 bp stem length was used in all subsequent tests.

Example 4

Two-Dimensional Structure of Prototype Decoy RNA and Optimization of Inhibitory Power by MBS Modification To increase the inhibitory effect, decoy RNAs were designed to have a secondary structure more complex than those of the prototypes (FIG. 2A), those expression cassettes were inserted into lentiviral vectors and introduced into the same assay cells as those used in FIG. 1B. The RNAs tested herein (decoy #10 to #16, FIG. 2A) showed a higher efficiency than the prototype decoy RNA (decoy RNA #2) (FIG. 2AB). Importantly, when three-nucleotide linker sequences were inserted into both ends of the MBS of decoy RNA #12 (decoy RNA #13), GFP expression nearly completely recovered, and the GFP expression due to decoy #13 introduction reached the same level as that of HeLaS3 which only has the miR-140-3p reporter (99.5%) (FIG. 2B). This recovery shows that the miR-140-3p activity provided by the miR-140-5p/miR-140-3p vector is completely offset.

Next, to accomplish a more efficient decoy activity, several sequences for MBS were screened. It has been reported that in mammals, attenuation of translation is caused more by an MBS containing four extra nucleotides between the nucleotide at position 8 and the nucleotide at position 9 from the 3' end of a completely complementary than by RNA cleavage (Kiriakidou, M. et al. (2004) Genes Dev, 18, 1165-1178; Vermeulen, A. et al. (2007) RNA, 13: 723-730). Therefore, since MBS containing four extra nucleotides can avoid cleavage of the decoy RNA molecule itself, it may inhibit miRNA function more efficiently than a completely complementary MBS (MBS-pf). To screen for MBSs that are efficient for inhibition, prototype decoy (FIG. 1A) was modified by inserting an extra sequence of one to four nucleotides between the nucleotides of positions 10 and 11 from the 3' end of a completely complementary MBS, which is a site where the Ago2 protein in RISC cleaves the target mRNA. Investigation of effects of such decoys showed that of the investigated decoys, MBS having an insertion of four nucleotides (MBS-4ntin) shows the largest GFP expression recovery (52%) (FIG. 3).

Figure 4:
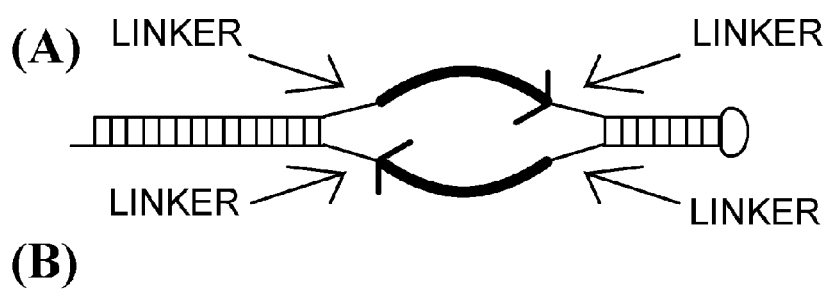
FIG. 4 shows comparison of the effects of the linker sequence length of the decoy RNAs. (A) The structure of decoy RNAs #22 to #26. The black thick curved arrows represent MBSs (5' to 3'). The arrows indicate linker sequences. (B) Relative GFP expression was determined as mentioned in the description of FIG. 1B. The lengths of the linker sequences are also shown in the panel.

Since inhibitory effects also improved dramatically by inserting linkers between the MBS and stems of a prototype decoy (FIG. 2B, compare decoy RNAs #12 and #13), decoy #12-type RNA in which MBS is replaced with MBS-4ntin was used to carefully change the linker length to one to five nucleotides. Insertion of one to three nucleotides resulted in high inhibitory effects, and insertion of four or five nucleotides showed moderate activity although the effect was lower (FIG. 4). Therefore, in subsequent analyses, the length of linker between MBS and stem RNA was set to three nucleotides.

The inventors tried to improve the inhibitory effect of decoy #16 shown in FIG. 2 by integrating the above-mentioned results. Decoy #27 was produced by inserting a three-nucleotide linker between the stem sequence and MBS, and by additionally substituting MBS-pf with MBS-4ntin. Decoy #27 was hugely improved (from 55.2% to 80.1%, FIGS. 2 and 5). On the other hand, while decoy #13 was subjected to structural modification according to the same principles to produce decoy #24, this did not improve the inhibitory ability. This is probably because the decoy activity of decoy #24 was already nearly saturated and the exogenously introduced miR-140-3p activity was completely offset.

Tentatively, decoy RNAs having the structures of decoy #13 and #24 (FIG. 6A) were concluded to be very promising since these RNAs inhibited the function of miRNA very efficiently. These decoy RNAs have two MBSs, and they are adjacent to two stem structures. For example, the two MBSs are individually positioned between the two stem structures, and the nucleic acid chains of the respective MBSs are in opposite directions. The two stem structures may be double-strands or quadruplexes. As shown in FIG. 6B, the expression cassette for such RNA can be easily constructed. This way, a decoy RNA having a structure comprising two MBS, wherein the two MBS are positioned between two stem structures (called Tough Decoy (TuD)), was found to result in particularly strong miRNA-inhibiting effects.

Example 5

Figure 7:
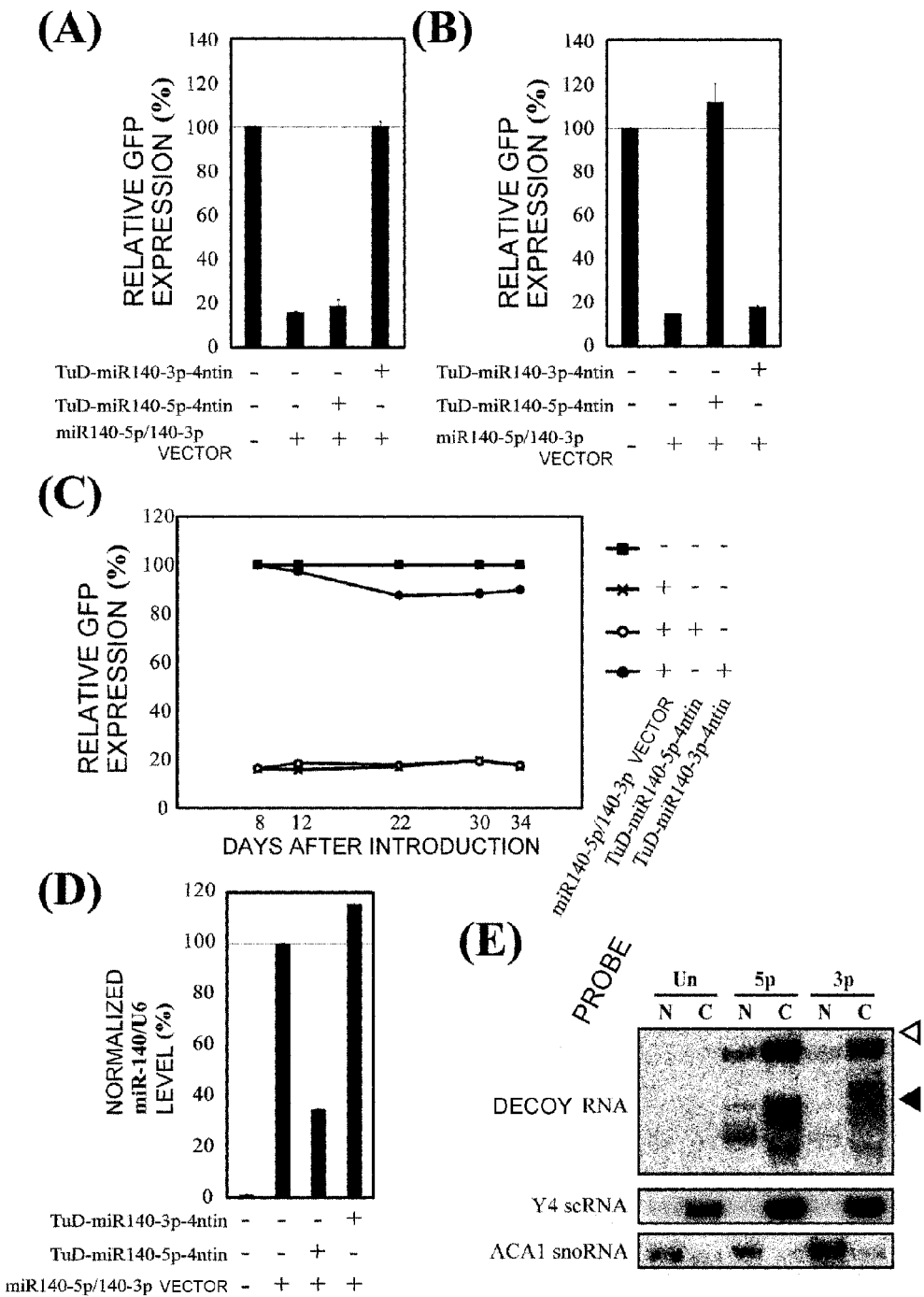
FIG. 7 shows the versatility, specificity, and duration of the inhibitory effect of the miRNA-inhibiting complexes of the present invention. (A) The effect of TuD-miR140-5p-4ntin or TuD-miR140-3p-4ntin on miR140-3p activity that was detected by the GFP reporter cell system for FIG. 1B. The GFP expression level was determined eight to twelve days after introduction (FIGS. 16D and E). (B) The effect of TuD-miR140-5p-4ntin or TuD-miR140-3p-4ntin on miR140-5p activity. Lentiviral vectors for expressing these miRNA-inhibiting RNAs were individually introduced into HeLaS3 cells carrying both the miR-140-5p reporter and miR140-5p/140-3p vector. Eight to twelve days after introduction, GFP expression levels were determined. The expression levels were normalized against the expression level of HeLaS3 cells carrying the miR-140-5p reporter alone, and presented as mean±SEM. (C) Time-dependent changes in the inhibitory effect of TuD-miR140-3p-4ntin against miR140-3p activity described in FIG. 1B. Relative GFP expression levels were normalized against those of HeLaS3 cells carrying the miR-140-3p reporter alone. (D) Mature miR140-5p levels in cells described in panel (B) as determined by quantitative realtime RT-PCR. The miR140-5p expression level was normalized against that of HeLaS3 cells carrying both the miR-140-5p reporter and the miR140-5p/140-3p vector, and presented as mean±SEM (n =3). U6 snRNA was used as the internal control. (E) Analysis of the intracellular localization of miRNA-inhibiting RNAs. The mobilities of Y4 small cytoplasmic RNA (Y4 scRNA, 93nt) and ACA1 small nucleolar RNA (ACA1 snoRNA, 130nt) are indicated with triangles. Y4 scRNA and ACA1 snoRNA PA-1 are shown as cell fraction markers. Un, 5p, 3p, N, and C indicate uninfected cells, TuD-miR140-5p-infected cells, TuD-miR140-3p-infected cells, nuclear fraction, and cytoplasmic fraction, respectively.

Versatility, Specificity, and Duration of Inhibitory Effects of the RNA Complexes of the Present Invention To investigate the versatility and specificity of inhibitory effects of the RNA complexes of the present invention, a reporter cell system for miR-140-5p in which the insertion sequence of the miR-140-3p reporter was simply replaced with a sequence completely complementary to miR-140-5p was constructed (FIG. 15(B)). The inhibitory effects of TuD-miR-140-3p (TuD-miR-140-3p-4ntin) (decoy #24) and TuD-miR-140-5p-4ntin (FIG. 18) which contain four extra nucleotides in MBS were determined using both of the reporter cell systems. In the miR-140-3p reporter system, introduction of TuD-miR-140-3p-4ntin showed a complete recovery of GFP expression, but expression of TuD miR-140-5p-4ntin did not show effects (FIG. 7A). In the miR-140-5p reporter system, introduction of the TuD-miR-140-5p-4ntin vector showed a complete recovery of GFP expression, but introduction of the TuD-miR-140-3p-4ntin vector did not show effects on this reporter (FIG. 7B). These results indicate that the inhibitory effects of these RNAs are highly efficient and specific for their target miRNA, and suggest that RNA complexes of the present invention can be applied to various miRNAs with high specificity.

One of the important advantages of lentivirus-based vectors is that expression of decoy RNA may be maintained for a long period of time. Therefore, the TuD-miR-140-3p-4ntin vector was introduced into HeLaS3 cells carrying both the miR-140-3p reporter and the miR140-5p/140-33p vector, and the change in GFP expression level over time was monitored for over one month (FIG. 7C). Those results indicated that TuD-miR-140-3p-4ntin efficiently inhibited the target miR-140-3p in HeLaS3 cells for over one month, and TuD-miR-140-5p-4ntin maintained the condition of absolutely no inhibition.

Next, the miR-140-5p level was directly investigated using quantitative real time RT-PCR. It was shown that when this method was used for detection, TuD-miR-140-5p-4ntin decreased the apparent expression level of miR-140-5p by approximately 65%, but TuD-miR-140-3p-4ntin did not cause such decrease (FIG. 7D). The results showed that the amount of free miR-140-5p decreased to approximately ⅓, but dsRNA formed between RNA decoy and mature miRNA may be too stable for detection of mature miRNA by realtime PCR, for example, even after RNA production.

Intracellular localization of the RNA expressed in HeLaS3 cells expressing TuD-miR-140-3p-4ntin or TuD-miR-140-5p-4ntin was investigated. Fourteen days after introduction of the TuD-miR-140-3p-4ntin vector or TuD-miR-140-5p-4ntin vector, nuclear fraction RNA and cytoplasmic fraction RNA of the cells were each prepared. To minimize intramolecular and intermolecular bonding, PAGE was performed at high temperature and analyses were carried out by Northern blotting. With probes against the expressed miRNA-inhibiting RNAs, a 120 nt band and a broad band near 90 nt were observed (FIG. 7E). Since this broad band intensified when the same RNA sample was subjected to PAGE at room temperature and then analyzed by Northern blotting, this is an intramolecularly bonded full-length RNA. TuD-miR-140-3p-4ntin and TuD-miR-140-5p-4ntin were mainly present in the cytoplasm, and a small amount of TuD-miR-140-5p-4ntin was present in the nucleus. This confirmed that the transcribed RNAs are efficiently transported to the outside of the nucleus. Furthermore, while the MBS sequence affects the efficiency of extranuclear transport of RNA to some degree, its effect was shown to be minimal.

Example 6

Inhibitory Effects of RNA Complexes of the Present Invention Against Endogenous miRNA To confirm that the inhibitory function of the RNA complexes of the present invention has versatility, several experiments were subsequently carried out using a different target miRNA (endogenous miR-21) and a different assay system that allows comparison with conventional synthetic miRNA inhibitors. Using the same principles as TuD-miR-140-3p-4ntin and TuD-miR-140-3p-pf, two TuD-miR21, TuD-miR-21-4ntin and TuD-miR-21-pf were constructed, respectively (FIG. 18). Next, to attempt suppression of endogenous miR-21 activity in PA-1 cells, DNA-based vectors that express TuD-miR-21-4ntin or TuD-miR-21-pf (FIG. 18) were transiently transfected into PA-1 cells together with a *Renilla* luciferase reporter which may optionally have insertion of a 21-bp DNA sequence completely complementary to mature miR-21 in 3'-UTR and a control Firefly luciferase reporter as a control for transfection (FIG. 17 (A to C)). As compared to the expression in cells transfected with a DNA-based vector (TuD-NC) expressing the negative control, the TuD-miR21-4ntin-expressing cell population showed an approximately 25-fold increase in miR21 reporter expression, specifically *Renilla* luciferase activity after normalization with Firefly luciferase activity (FIG. 8A). TuD-miR-21-pf showed lower inhibitory effects, but still resulted in a significant recovery corresponding to approximately 14-fold activity. Importantly, the recovered reporter activity level was close to that of the control reporter without the miR-21 target sequence. As expected, the activity of this control reporter was independent of the introduced decoy RNA and was nearly constant.

Next, the inhibitory effect of the transiently transfected expression vector which produces the RNA complexes of the present invention was compared with that of the LNA/DNA antisense oligonucleotide as described in Section 1.5 of Example 1 (FIG. 8A). Transfection of PA-1 cells by a locked nucleic acid (LNA/DNA) antisense oligonucleotide (LNA-miR21) caused a two-fold increase in the expression of the miR21 target reporter compared to that of PA-1 cells transfected with LNA/DNA-NC used as the negative control. These results show that the RNA complexes of the present invention have a much higher ability to inhibit miRNA under these transfection conditions than conventional synthetic reagents.

Figure 9:
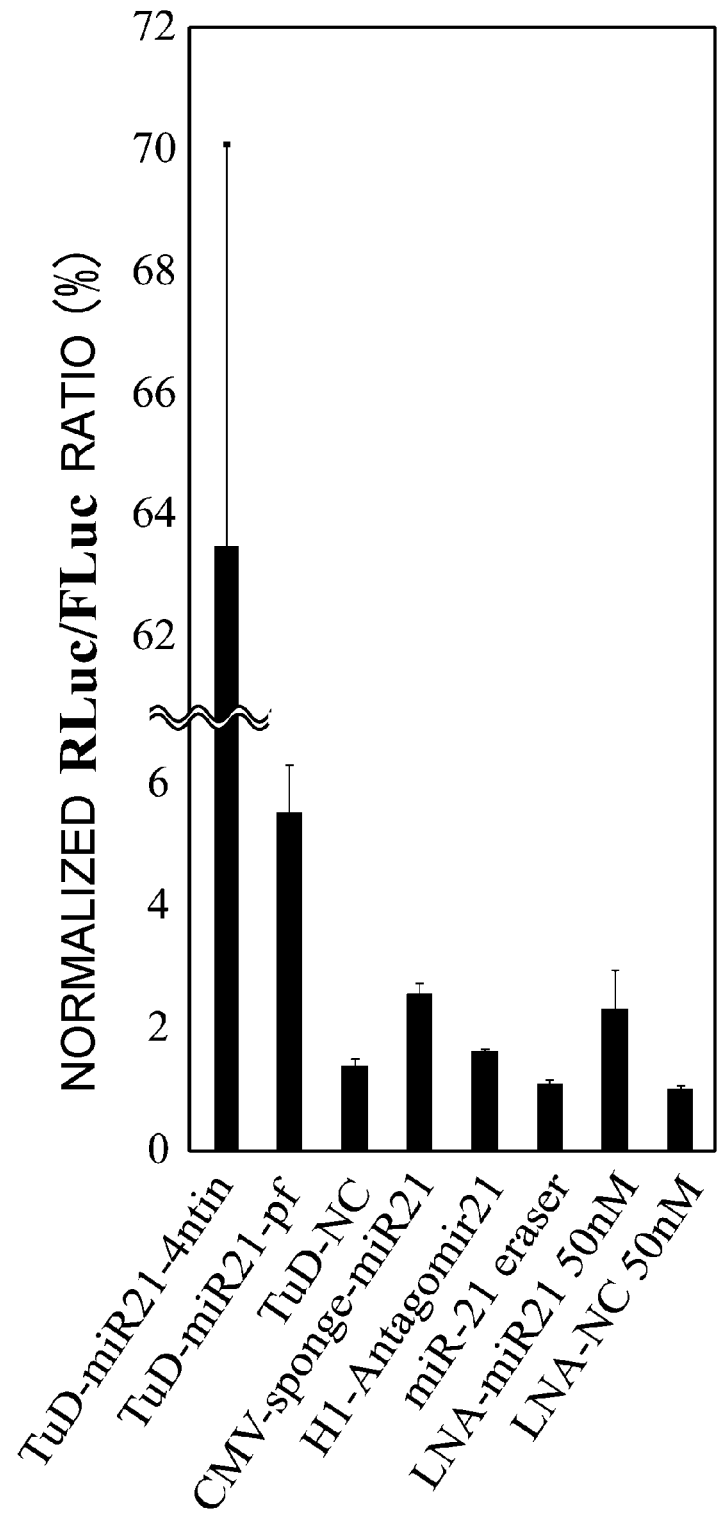
FIG. 9 shows comparison of the effects of the miRNA-inhibiting RNA expression plasmid vectors, CMV sponge expression plasmid vector, H1-Antagomir expression plasmid vector, miRNA eraser expression plasmid vector, and LNA/DNA antisense oligonucleotides. Dual luciferase assay was performed 72 hours after transfection using HCT-116 cells. The expression levels were normalized against those of HCT-116 cells transfected with the non-targeted control Renilla luciferase reporter, and presented as mean±SEM.

The cell line for the assay was changed from PA-1 used above to HCT-116, and comparison of the miRNA-inhibiting effects of plasmid vectors that express RNA complexes of the present invention with those of a CMV sponge expression plasmid vector, H1-Antagomir expression plasmid vector, miRNA eraser expression plasmid vector, and LNA/DNA antisense oligonucleotide was carried out as described in Section 1.5 of Example 1 (FIG. 9). As a result, the RNA complexes of the present invention were shown to be very highly effective compared to other methods.

Next, the cell line for assay was changed from PA-1 to HCT-116, and similar experiments were carried out. HCT-116 has been reported to have higher endogenous miR-21 than that of PA-1. The overall results were very similar except that the inhibitory effect of TuD-miR-21-pf was dramatically decreased (FIG. 8B). These results may be showing that as a result of very efficient cleavage of the TuD-miR-21-pf molecule by a large amount of endogenous miR-21, the physical concentration of this decoy is significantly decreased compared to the concentration of TuD-miR-21-4ntin.

Figure 10:
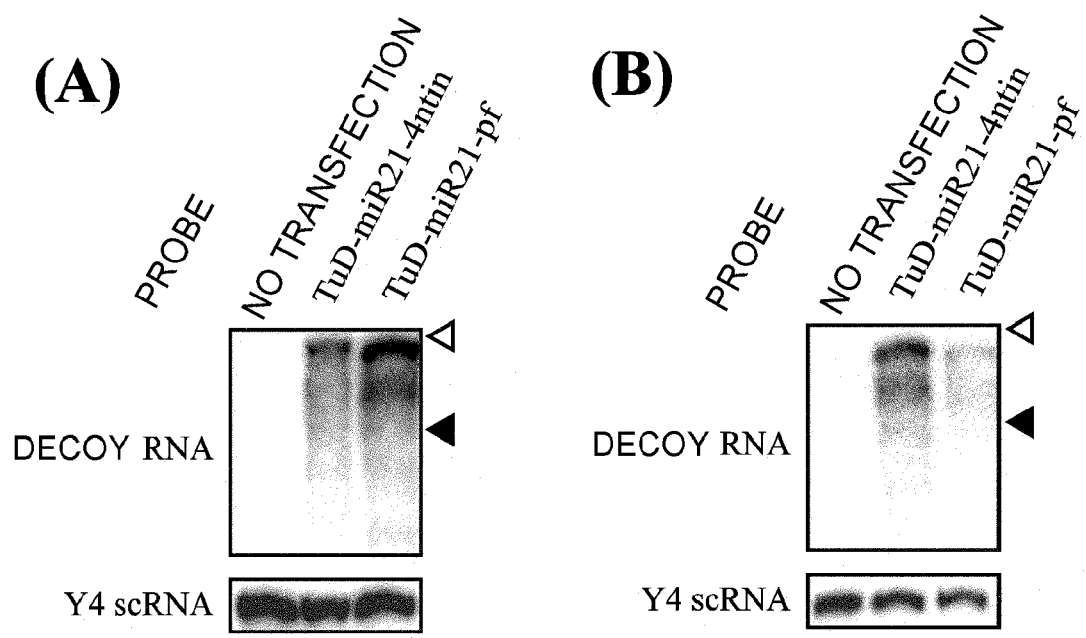
FIG. 10 shows Northern blotting analysis of miRNA-inhibiting RNA expression levels. The expression levels of TuD-miR-21-4ntin and TuD-miR-21-pf in PA-1 (A) and HCT-116 cells (B) transfected with the miRNA-inhibiting RNA expression vectors were analyzed by Northern blotting. The mobilities of Y4 scRNA and ACA1 snoRNA are indicated with triangles. Y4 scRNA was shown as a loading control.

In PA-1 cells and HCT-116 cells transfected with expression vectors of miRNA-inhibiting RNAs (TuD-miR-21-4ntin and TuD-miR-21-pf), the expression levels of TuD-miR-21-4ntin and TuD-miR-21-pf were each analyzed by Northern blotting. In PA-1 cells, TuD-miR-21-4ntin and TuD-miR-21-pf were both strongly expressed (FIG. 10A). In HCT-116 cells, TuD-miR-21-4ntin was strongly expressed but TuD-miR-21-pf only showed weak expression in comparison (FIG. 10B). These phenomena match well with the above-mentioned hypothesis that under conditions of high miR-21 concentration, TuD-miR-21-4ntin is stable against degradation by miRNA, whereas TuD-miR-21-pf is susceptible to degradation.

The miR-21 level was investigated using quantitative real-time RT-PCR. As a result, TuD-miR-21-4ntin and TuD-miR-21-pf greatly reduced the apparent expression level of miR-21 (FIG. 8D). However, investigation of the miR-21 level by Northern blotting showed that decrease was not observed in pre-miR-21 or mature-miR-21 (FIG. 8E). As an explanation for this result, one can consider that although the actual amount of miR-21 was not decreased, detection by RT-PCR was inhibited due to strong binding between miR-21 and TuD-miR-21. Such phenomena have been pointed out by other research groups as well.

The dependency of miR-21 inhibiting effects on the amount of TuD-miR-21-4ntin expression plasmid was investigated in HCT-116 cells. The experiments of FIG. 8A, B, and FIG. 9 were performed at 500 ng/well in a 24-well plate, but when the quantity dependency was investigated, the effect was saturated at 300 ng/well, and even at 10 ng/well, one third or so of that miRNA-inhibiting effect was observed (FIG. 19).

The RNA of the present invention showed high miRNA-inhibiting effects even in colon cancer cells (SW480, HT29), immortalized human lung embryonic fibroblasts (TIG-3/E/TERT), and rat fibroblasts (3Y1) (FIG. 20).

To directly monitor effects of miR21 on its endogenous target, the PDCD4 protein, a series of miRNA-inhibiting RNA expression vectors were individually transfected into PA-1 cells, total proteins were collected, and the expression level of PDCD4 was examined by Western blotting (FIG. 8C). Expression of PDCD4 increased due to TuD-miR-21-4ntin or TuD-miR-21-pf, but TuD-NC did not show effects. This result indicates that RNA complexes of the present invention can specifically inhibit the function of endogenous miRNA.

Figure 11:
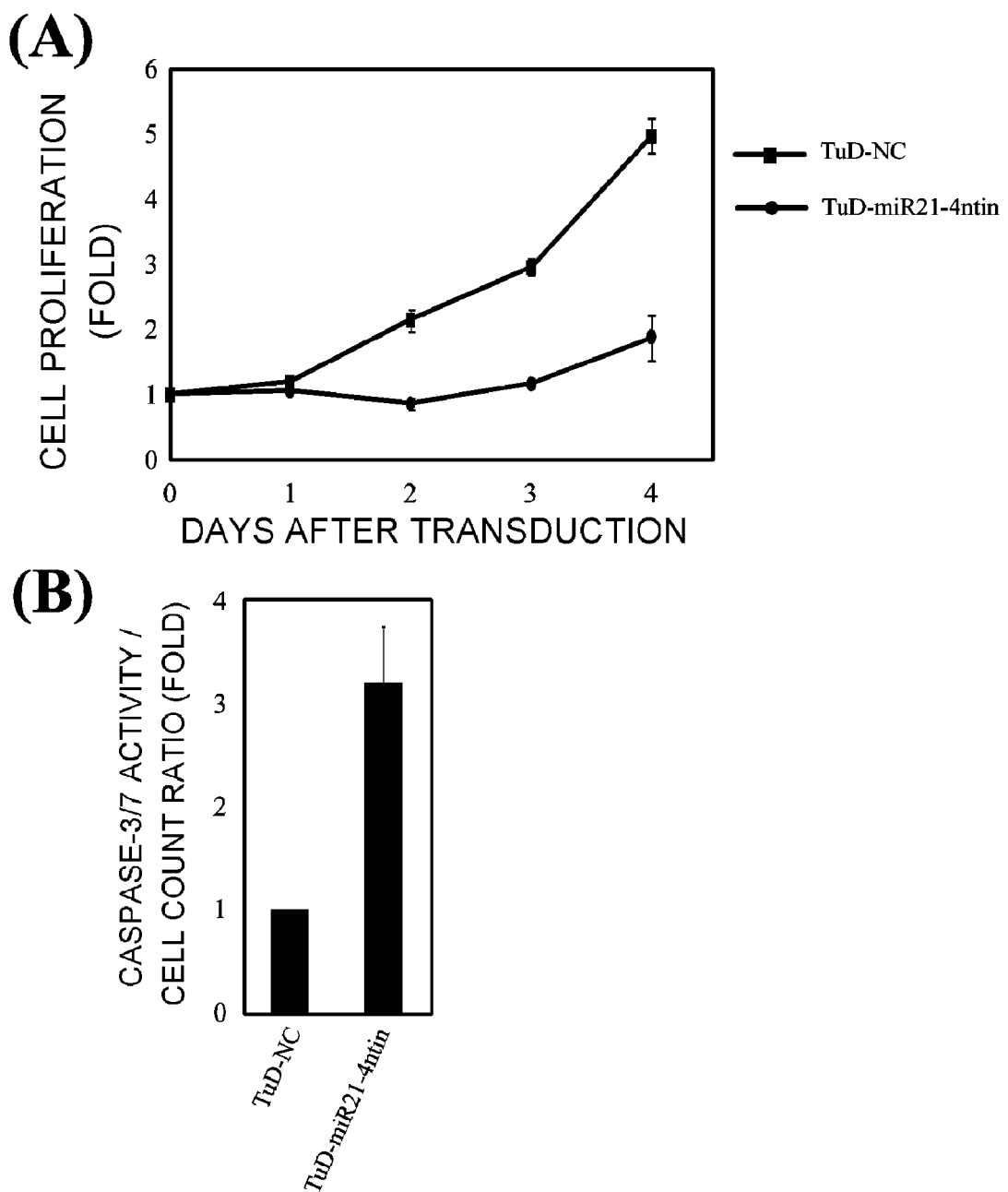
FIG. 11 shows the biological activity induced by introduction of a miRNA-inhibiting RNA. (A) Analysis of the cell growth activity of PA-1 cells after introduction of TuD-miR21. The miRNA-inhibiting RNA expression vector was introduced into PA-1 cells, and the cell count was measured for four days after vector introduction. (B) Analysis of apoptosis induction in PA-1 cells after introduction of TuD-miR21. The miRNA-inhibiting RNA expression vector was introduced into PA-1 cells, and caspase-3 activity and caspase-7 activity were measured three days after vector introduction. The activities were normalized against the number of PA-1 cells transfected with each miRNA-inhibiting RNA expression vector, and presented as mean±SEM.

Whether the above-mentioned miRNA-inhibiting RNA induces biological activity by suppressing miRNA function was investigated using the PA-1 cell line. Lentiviral vectors that express TuD-miR21-4ntin and TuD-NC were introduced into PA-1 cells at MOI 10, and the cell growth activity was measured (FIG. 11A). Cells transfected with TuD-NC proliferated up to five times or more in four days, but cells transfected with TuD-miR21-4ntin proliferated only up to 1.6 times or so. Furthermore, using a similar culture, the activities of caspase 3 and 7 were measured to evaluate apoptosis (FIG. 11B). As compared with TuD-NC-transfected cells, cells transfected with TuD-miR21-4ntin showed an increase of three times or so. This suggests that induction of apoptosis might be one of the reasons that the degree of cell proliferation was low in cells transfected with TuD-miR21-4ntin. The above showed that RNAs of the present invention sufficiently suppressed the function of miRNA, and this inhibited the apoptosis-suppressing activity and growth stimulating activity of miR-21 (Corsten, M. F., (2007) Cancer Res. 67, 8994-9000).

It is thought that among miRNAs, there are miRNA families that have identical seed sequences and common target genes. To investigate whether the miRNA-inhibiting RNA of the present invention has inhibitory effects against a family of target miRNAs, experiments were carried out using the miRNA-15a, 15b, 16, 195, 424, 497 family as targets. A luciferase reporter vector for miR-16, in which the inserted sequence of the miR-21 luciferase reporter was substituted with a sequence completely complementary to miR-16, was constructed (FIG. 17D). HCT-116 cells which were observed by miRNA micro array to express miRNA-15a, 15b, and 16, but not miRNA-195,424, and 497 were used (FIG. 21). As shown in FIG. 12A, miRNA-16 and 195 have high homology, and miRNA-16 and 497 have low homology except at the seed site. Therefore, TuD-miR-16-4ntin, TuD-miR-195-4ntin, and TuD-miR497-4ntin were constructed (FIGS. 18 and 12B). Since miRNA-195 and 497 were not expressed under this condition, inhibitory effects of TuD-miR-195-4ntin and TuD-miR497-4ntin on miRNA-15a, 15b, and 16 could be observed. When luciferase assay was performed, cell populations expressing TuD-miR-16-4ntin, TuD-miR-195-4ntin, and TuD-miR497-4ntin showed respectively a 3.1-fold, 5.2-fold, and 2.6-fold increase in miR16 reporter expression, specifically *Renilla* luciferase activity normalized with Firefly luciferase activity, as compared to the expression in a cell population transfected with TuD-NC (FIG. 12C). In particular, the level of reporter activity recovered by TuD-miR-16-4ntin and TuD-miR-195-4ntin was at the same level as the activity of the control reporter which does not have the miR-16 targeting sequence. Furthermore, the activity of the control reporter did not depend on the introduced miRNA-inhibiting RNA and was nearly constant. From this experiment, the inhibitory effects of an RNA of the present invention was confirmed to be effective not only towards the target miRNA but also to its family. Furthermore, while the inhibitory effect was higher towards a highly homologous family than against a family with low homology, inhibitory effects were shown to be present even when the homology was low.

Example 7 miRNA Inhibition by Synthetic Oligonucleotides

RNA complexes of the present invention were produced using oligonucleotides and inhibitory effects against endogenous miRNA were investigated.

Cell Culture

HCT-116 cells (Cancer Res 1981; 41:1751; J Nat Cancer Inst 1982; 69:767) were cultured at 37° C. in DMEM containing 10% fetal bovine serum (FBS).

Luciferase Assay

HCT-116 cells were seeded in DMEM containing 10% fetal bovine serum (FCS) at $1 \times 10^5$ cells per well in a 24-well plate. Lipofectamine 2000 (Invitrogen) and 10 ng of pTK4.12C.P- (Firefly luciferase plasmid; internal control), 100 ng of pGL4.74-miR21T (RLuc target reporter plasmid), or pGL4.74 without a target sequence, and 1, 3, 10, 50, and 200 nM 2'-O-Methyl-TuD-RNA oligonucleotide, and 2'-O-Methyl-RNA antisense oligonucleotide•LNA/DNA antisense oligonucleotide•PNA antisense oligonucleotide were transfected in triplicate. The LNA/DNA antisense oligonucleotide was synthesized at ThermoELECTRON Co., and contains locked nucleic acids at eight nucleotides positioned continuously at the center (Naguibneva, I. et al. (2006) Biomed Pharmacother, 60, 633-638). TuD-2'-O-Methyl-RNA oligonucleotide, 2'-O-Methyl-RNA antisense oligonucleotide, LNA/DNA antisense oligonucleotide, and PNA antisense oligonucleotide have the sequences shown in (1) below. miRIDIAN Inhibitor is a synthetic oligo purchased from Thermo Scientific Dharmacon Co. All assays were performed 48 hours after transfection by dual luciferase assay (Promega) using GLOMAX™ (Promega).

Oligonucleotides That Were Used (1) Sequences of 2'-O-Methyl-RNA Antisense Oligos and LNA/DNA Antisense Oligos For 2'-O-Methyl-TuD-miR21, a mixture of 5'-GACG-GCGCUAGGAUCAUCAACUCAACAUCAGU-CAAUGUGAUAAGCUACAAGUA UUCUGGU-3' (SEQ ID NO: 148) and 5'-ACCAGAAUACAACUCAACAU-CAGUCAAUGUGAUAAGCUACAAGAUGAUCCUAG CGCCGUC-3' (SEQ ID NO: 149) were annealed and then used. All nucleotides were 2'-O-Methylated.

For 2'-O-Methyl-miR21, 5'-GUCAACAUCAGU-CUGAUAAGCUA-3' (SEQ ID NO: 150) was used. For 2'-O-Methyl-NC, 5'-AAGGCAAGCUGACCCUGAAGU-3' (SEQ ID NO: 151) was used. All nucleotides were 2'-O-Methylated.

For LNA-miR21, 5'-TCAACAT CAGTCTGATAAGCTA-3' (SEQ ID NO: 79) was used. For LNA-NC, 5'-CATTAATGTCGGACAACTCAAT-3' (SEQ ID NO: 80) was used. The sequence subjected to LNA modification is indicated by underline.

For PNA-miR21, 5'-RRRQRRKKR-OO-ATTAATGTCGGACAA-3' (SEQ ID NO: 152, 153) was used. For PNA-NC, 5'-RRRQRRKKR-OO-TCAACATCAGTCTGA-3' (SEQ ID NO: 152, 154) was used. All nucleotides were PNAs. The cell penetrating peptide and the AEEA linker (AEEA: 8-amino-3,6-dioxaoctanoic acid) are indicated by underline.

Results

To investigate the inhibitory functions of 2'-O-Methyl-TuD-RNA oligonucleotides, various antisense oligos were transiently transfected into HCT-116 cells together with a *Renilla* luciferase reporter which may optionally have the insertion of a 21-bp DNA sequence completely complementary to mature miR-21 in 3'-UTR and a Firefly luciferase reporter pTK4.12C.P- as an internal control for transfection (FIG. 22). The cell population transfected with 2'-O-Methyl-TuD-miR21 showed an approximately 21-fold, 43-fold, 51-fold, 58-fold, and 69-fold increase in miR21 reporter expression, specifically *Renilla* luciferase activity normalized with Firefly luciferase activity, at concentrations of 1 nM, 3 nM, 10 nM, 50 nM, and 200 nM, respectively, when compared to the expression in cells transfected with 2'-O-Methyl-NC (FIGS. 22 and 23). On the other hand, 2'-O-Methyl-miR21, LNA-miR21, and PNA-miR21 only showed an approximately six-fold, two-fold, and 11-fold increase or so, respectively, even at 200 nM. The miR-21-inhibiting effects of the 2'-O-Methyl-TuD-RNA oligonucleotide and the miRIDIAN inhibitor were compared at concentrations of 0.1 nM, 0.3 nM, 1 nM, and 3 nM. At the respective concentrations, 2'-O-Methyl-TuD-miR21 showed an approximately 3.0-fold, 9.1-fold, 28.9-fold, and 45.9-fold increase or so, and miRIDIAN Inhibitor-miR21 showed an approximately 2.5-fold, 5.2-fold, 11.6-fold, and 20.1-fold increase or so (FIG. 24). On the other hand, the activity of the *Renilla* luciferase reporter which does not carry a target sequence was nearly constant at low concentration and independent of the introduced antisense oligo. These results show that 2'-O-Methyl-TuD-miR21 has a much higher ability to inhibit miRNA than conventional synthetic reagents under these transfection conditions.

Example 8 miRNA Inhibition Using Other Promoters

Plasmid Construction

PCR was performed using human genomic DNA and the primers indicated in (2) below, and cloned into pCR2.1 to produce ph7SK-protoshuttle (FIG. 27(A)). ph7SK-protoshuttle was digested with KpnI-HindIII, and oligonucleotides shown in (2) below were annealed. Cloning was carried out to produce ph7SK-TuD-shuttle. Each oligo pair shown in (3) below was annealed and cloned into BsmBI-digested ph7SK-TuD-shuttle to produce ph7SK-TuD-miR21-4ntin. Thereafter, the BamHI-EcoRI fragment of ph7SK-TuD-miR21-4ntin was inserted to the BamHI-EcoRI site of pSL1180 (Pharmacia) to produce the miRNA-inhibiting RNA expression plasmid vector pSL1180-TuD-mR21-4ntin.

Oligonucleotides Used
(2) Primer Pairs for Construction of Shuttle Vectors for the RNAs of the Present Invention For ph7SK-protoshuttle, 5'-GGATCCTGCAGTATTTAG-CATGCCCCA-3' (SEQ ID NO: 155) was used as the forward primer and 5'-GAATTCAAAAAAGGATGTGAGGGCGT-CATCGAGACGGTACCGTCTCCGATGACGC CCTCA-CATCCGAGGGTACCCAGGCGGCGCACAAGC-3' (SEQ ID NO: 156) was used as the reverse primer; and for ph7SK-TuD-shuttle, 5'-CTCGGATGTGAGGGCGTCATCG-GAGACGACACCATCCACAGCCAGCGTCTCGATG ACGCCCTCACATCCTTTTTTGAATTCA-3' (SEQ ID NO: 157) was used as the sense strand and 5'-AGCTTGAAT-TCAAAAAAGGATGTGAGGGCGTCATC-GAGACGCTGGCTGTGGATGG TGTCGTCTCCGAT-GACGCCCTCACATCCGAGGTAC-3' (SEQ ID NO: 158) was used as the antisense strand.
(3) Primer Pair for Construction of an Expression Vector of the RNA of the Present Invention For TuD RNA-miR21-4ntin, 5'-CATCAACTCAACAT-CAGTCAATGTGATAAGCTACAAGTAT-TCTGGTCACAGAATAC AACTCAACATCAGTCAAT-GTGATAAGCTACAAG-3' (SEQ ID NO: 17) was used as the sense strand and 5'-TCATCTTGTAGCTTATCACAT-TGACTGATGTTGAGTTGTATTCTGTGAC-CAGAATACT TGTAGCTTATCACATTGACTGATGT-TGAGTT-3' (SEQ ID NO: 18) was used as the antisense strand.

Results

Comparison of Inhibitory Effects of the mU6 Promoter and h7SK Promoter

To compare the inhibitory effects of the mU6 promoter and h7SK promoter, a miRNA-inhibiting RNA expression plasmid vector was transiently transfected into HCT-116 cells together with a *Renilla* luciferase reporter (pGL4.74-miR21T and pGL4.74, respectively) which may be inserted with a 21 bp DNA sequence completely complementary to mature miR-21in3'-UTR and a Firefly luciferase reporter (pTK4.12C.P-) as an internal control for transfection. The cell population transfected with mU6 promoter-TuD-miR21 showed an approximately 59-fold increase in miR21 reporter expression, specifically *Renilla* luciferase activity normalized with Firefly luciferase activity, as compared to the expression of cells transfected with mU6 promoter-TuD-NC (FIG. 27(B)). On the other hand, h7SK promoter-TuD-miR21 showed an approximately 77-fold increase compared to the expression of cells transfected with h7SK promoter-TuD-NC. These results indicate that under these transfection conditions, the h7SK promoter has a higher ability.

Example 9

Effects of Higher Order Structure

Plasmid Construction

Each oligo pair shown in (4) below was annealed and cloned into BsmBI-digested pmU6-TuD-shuttle to produce pmU6-TuD-miR21-4ntin-GqL111, pmU6-TuD-miR21-4ntin-GqL333, pmU6-TuD-miR21-4ntin-1MBS-1, and pmU6-TuD-miR21-4ntin-1MBS-2. The BamHI-EcoRI fragments of these plasmids were inserted to the BamHI-EcoRI site of pSL1180 (Pharmacia) to produce miRNA-inhibiting RNA expression plasmid vectors pSL1180-TuD-miR21-4ntin-GqL111, pSL1180-TuD-miR21-4ntin-GqL333, pSL1180-TuD-miR21-4ntin-1MBS-1, and pSL1180-TuD-miR21-4ntin-1MBS-2.

Oligonucleotides That Were Used
(4) Primer Pairs for Construction of Expression Vectors of the RNAs of the Present Invention For TuD RNA-miR21-4ntin-GqL111, 5'-CATCAACT-CAACATCAGTCAATGTGATAAGCTA-CAAGGGAGGGCGGGAGGGAACT CAACATCAGT-CAATGTGATAAGCTACAAG-3' (SEQ ID NO: 159) was used as the sense strand, and 5'-TCATCTTGTAGCTTATCA-CATTGACTGATGTTGAGTTCCCTCCCGC-CCTCCCTTGTA GCTTATCACATTGACTGATGT-TGAGTT-3' (SEQ ID NO: 160) was used as the antisense strand.

For TuD RNA-miR21-4ntin-GqL333, 5'-CATCAACT-CAACATCAGTCAATGTGATAAGCTA-CAAGGGAGAGGGGCGGGGCGCG GGAACTCAA-CATCAGTCAATGTGATAAGCTACAAG-3' (SEQ ID NO: 161) was used as the sense strand, and 5'-TCATCTTG-TAGCTTATCACATTGACTGATGTTGAGT-TCCCGCGCCCCGCCCCTCCC CTTGTAGCTTATCA-CATTGACTGATGTTGAGTT-3' (SEQ ID NO: 162) was used as the antisense strand.

For TuD RNA-miR21-4ntin-1MBS-1, 5'-CATCAACT-CAACATCAGTCAATGTGATAAGCTA-CAAGTATTCTGGTCACAGAATAC AACATCGAATAGT-GTAACTGACTACAACTCAAG-3' (SEQ ID NO: 163) was used as the sense strand, and 5'-TCATCTTGAGTTGTAGT-CAGTTACACTATTCGATGTTGTATTCT-GTGACCAGAATAC TTGTAGCTTATCACATTGACT-GATGTTGAGTT-3' (SEQ ID NO: 164) was used as the antisense strand.

For TuD RNA-miR21-4ntin-1MBS-2, 5'-CATCAACT-CAACATCAGTCAATGTGATAAGCTA-CAAGTATTCTGGTCACAGAATAC AACAAGCCA-CAACGAATCTCTATATCATCAAG-3' (SEQ ID NO: 165) was used as the sense strand, and 5'-TCATCTTGAT-GATATAGAGATTCGTTGTGGCTTGTTG-TATTCTGTGACCAGAATACTT GTAGCTTATCACAT-TGACTGATGTTGAGTT-3' (SEQ ID NO: 166) was used as the antisense strand.

Results
(i) Comparison of Effects of Each Structure on Inhibitory Effects (G-Quadruplex)

An miRNA-inhibiting RNA was produced in which the shorter one of the two stem structures is replaced with a G-quadruplex which is known to be a rigid structure (FIG. 25). The sequence of a G-quadruplex is GGG-loop-GGG-loop-GGG-loop-GGG. When the length of this loop sequence is 1-1-1, the structure is referred to as being parallel, and when it is 3-3-3, the structure transitions between a parallel structure and an antiparallel structure. These were referred to as GqL111 and GqL333, respectively. Effects of the miRNA-inhibiting RNAs of each structure were compared by a luciferase reporter assay system using HCT-116 cells. mU6-TuD-miR21-4ntin increased the miR21 reporter expression approximately 40 fold compared to the mU6 promoter-TuD-NC. On the other hand, mU6-TuD-miR21-4ntin-GqL111 and mU6-TuD-miR21-4ntin-GqL333 increased approximately 33 fold and 20 fold, respectively (FIG. 25(C)).

(ii) Comparison of the Influence of Each Structure on Inhibitory Effects (1 MBS)

Two types of miRNA-inhibiting RNAs with one MBS were produced by substituting one of the two MBSs that face each other in a single molecule with an MBS that does not bind to the target miRNA (FIG. 26(A)). Effects of the miRNA-inhibiting RNAs of each structure were compared by a luciferase reporter assay system using HCT-116 cells. mU6 promoter-TuD-miR21 increased the miR21 reporter expression approximately 59 fold compared to mU6 promoter-TuD-NC. On the other hand, mU6-TuD-miR21-4ntin-1MBS-1 and mU6-TuD-miR21-4ntin-1MBS-2 increased approximately 22 fold and 6.5 fold, respectively (FIG. 26(B)).

According to the above-mentioned results, the number of MBS greatly affects the inhibitory effect. miRNA-inhibiting RNAs comprising one or three MBSs showed high inhibitory effects, but miRNA-inhibiting RNAs carrying two MBSs were most effective. In particular, TuD-miR21 carrying two MBSs exhibited a high inhibitory effect that significantly exceeds twice the effect of TuD-miR21-4ntin-1MBS-1 or TuD-miR21-4ntin-1MBS-2 carrying one MBS. It was shown that when the region facing MBS in a nucleotide sequence is not an MBS, the nucleotide sequence is able to affect the inhibitory effect significantly.

Example 10

Biological Activity Due to miR-200 Family Inhibition 1.1 Plasmid Construction

Each oligo pair shown in (5) below was annealed and cloned into pmU6-TuD-shuttle and ph7SK-TuD-shuttle digested with BsmBI to produce pmU6-TuD-miR200c-4ntin-3L, pmU6-TuD-miR200c-4ntin-3pL, ph7SK-TuD-miR200c-4ntin-3L, and ph7SK-TuD-miR200c-4ntin-3pL. The BamHI-EcoRI fragments of these plasmids were inserted into the BamHI-EcoRI site of pSL1180 (Pharmacia) to produce miRNA-inhibiting RNA expression plasmid vectors pSL1180-mU6-TuD-miR200c-4ntin-3L, pSL1180-mU6-TuD-miR200c-4ntin-3pL, pSL1180-h7SK-TuD-miR200c-4ntin-3L, and pSL1180-h7SK-TuD-miR200c-4ntin-3pL. Similar BamHI-EcoRI fragments were inserted into the BamHI-EcoRI site of pLCG (HIV-1-based GFP gene-containing lentiviral vector) to produce miRNA-inhibiting RNA expression lentiviral vectors pLCG-mU6-TuD-miR200c-4ntin-3L and pLCG-h7SK-TuD-miR200c-4ntin-3pL.

To construct a luciferase reporter plasmid, the oligonucleotide pair shownd below was annealed and cloned into pGL4.74 (Promega) digested with XbaI and FseI to produce pGL4.74-miR200cT.

1.2 Cell Culture and Construction of Stable Cell Lines

HCT-116 cells (Cancer Res 1981; 41:1751; J Nat Cancer Inst 1982; 69:767) were cultured in DMEM containing 10% fetal bovine serum (FBS) at 37° C.

HCT-116 cells were seeded at $1 \times 10^5$ cells per well in a 6-well plate, and 24 hours later, pLCG-mU6-TuD-miR200c-4ntin-3L, pLCG-mU6-TuD-NC, pLCG-h7SK-TuD-miR200c-4ntin-3pL, and pLCG-h7SK-TuD-NC viral stocks ($1 \times 10^6$ TU)) were each introduced in the presence of 8 μg/mL of polybrene. Eight days after transduction, GFP-expressing cells were fractionated using FACS Area.

1.3 Luciferase Assay

On the day before introduction, HCT-116 cells were seeded in DMEM containing 10% fetal bovine serum (FCS) at $1.0 \times 10^5$ cells per well in a 24-well plate. Lipofectamine 2000 (Invitrogen) and 10 ng of pTK4.12C.P- (Firefly luciferase plasmid; internal control), 100 ng of pGL4.74-miR200cT (RLuc target reporter plasmid), or pGL4.74 without a target sequence (FIG. 28A), and 1 ng and 10 ng of pSL1180-mU6-TuD-miR200c-4ntin-3L and pSL1180-mU6-TuD-NC•pSL1180-mU6-TuD-miR200c-4ntin-3pL•pSL1180-h7SK-TuD-NC were transfected in triplicate. Furthermore, 21 days after introduction of pLCG-mU6-TuD-miR200c-4ntin-3L lentivirus or pLCG-h7SK-TuD-miR200c-4ntin-3pL lentivirus, the respectively transduced cells were seeded in DMEM containing 10% fetal bovine serum (FCS) at 1.0×10⁵ cells per well in a 24-well plate. Lipofectamine 2000 (Invitrogen) and 10 ng of pTK4.12C.P- (Firefly luciferase plasmid; internal control), 100 ng of pGL4.74-miR200cT (RLuc target reporter plasmid), or pGL4.74 without a target sequence (FIG. 28A) were transfected in triplicate. All assays were performed 48 hours post-transfection using GLOMAX™ (Promega) by dual luciferase assay (Promega).

1.4 Western Blotting

Protein concentrations were measured using the Bio-Rad protein assay kit by extracting total protein from cells using 1.5×SDS Buffer 15 days after lentiviral transduction. The protein extract was separated on 10% SDS-PAGE and transferred to a PVDF-membrane (Milipore). Immunoblotting was performed by incubating the membrane with an anti-E-cadherin (ab76055, Abcam) antibody, anti-vimentin (sc6260, Santa cruz) antibody, and anti-Actin (612656, BD transduction) antibody at room temperature for two hours. After washing three times with phosphate-buffered saline containing Tween 20, the membranes were incubated with a horseradish peroxidase-conjugated secondary antibody at room temperature for one hour. The signals were detected using an ECL reagent (Amersham).

Oligonucleotides Used (5) Primer Pairs for Constructing Expression Vectors of the RNAs of the Present Invention For pmU6-TuD-miR200c-4ntin-3L and ph7SK-TuD-miR200c-4ntin-3L, 5'-CATCAACTCCATCATTAC-CCCACTGGCAGTATTACAAGTATTCTG-GTCACAGAATAC AACTCCATCATTACCCCACTGGCAGTATTACAAG-3' (SEQ ID NO: 179) was used as the sense strand, and 5'-TCATCTTGTAATACTGCCAGTGGGG-TAATGATGGAGTTGTATTCTGTGACCAGAATA CTTG-TAATACTGCCAGTGGGGTAATGATGGAGTT-3' (SEQ ID NO: 180) was used as the antisense strand.

For pmU6-TuD-miR200c-4ntin-3pL and ph7SK-TuD-miR200c-4ntin-3pL, 5'-CATCTCCATCATTACCCCACTG-GCAGTATTACGTATTCTGGTCACAGAATACTCCATC ATTACCCCACTGGCAGTATTACG-3' (SEQ ID NO: 181) was used as the sense strand, and 5'-TCATCGTAATACTGC-CAGTGGGGTAATGATGGAGTATTCTGT-GACCAGAATACGTAA TACTGCCAGTGGGGTAAT-GATGGA-3' (SEQ ID NO: 182) was used as the antisense strand.

For pGL4.74-miR200cT, 5'-CTAGACCGGAATTCTC-CATCATTACCCGGCAGTATTACTC-GAGCGGAGGCCGG-3' (SEQ ID NO: 183) was used as the sense strand, and 5'-CCTCCGCTCGAGTAATACTGC-CGGGTAATGATGGAGAATTCCGGT-3' (SEQ ID NO: 184) was used as the antisense strand.

Results

Examination of the miR200 Inhibition Effect of TuD200 by Luciferase Assay

The luciferase reporter assay system was used to investigate the effects of miRNA-inhibiting RNAs expressed from two types of promoters, the mU6 promoter and h7SK promoter. Furthermore, two types of miRNA-inhibiting RNAs: TuD-miR200c-4ntin-3L and TuD-miR200c-4ntin-3pL, which have different linker sequence lengths, were examined. In the experiment where 1 ng of the miRNA-inhibiting RNA (TuD200) expression plasmid vector of the present invention targeting miR200 was transfected, mU6-TuD-miR200c-4ntin-3L, mU6-TuD-miR200c-4ntin-3pL, h7SK-TuD-miR200c-4ntin-3L, and h7SK-TuD-miR200c-4ntin-3pL increased the miR200c reporter expression to approximately 5.7 fold, 6.7 fold, 6.1 fold, and 6.7 fold that of mU6-TuD-NC, respectively. On the other hand, h7SK-TuD-NC was nearly equivalent (FIG. 28B). In the experiment where 10 ng of the TuD RNA expression plasmid vector was transfected, mU6-TuD-miR200c-4ntin-3L, mU6-TuD-miR200c-4ntin-3pL, h7SK-TuD-miR200c-4ntin-3L, and h7SK-TuD-miR200c-4ntin-3pL increased the miR200c reporter expression to approximately 8.2 fold, 8.7 fold, 8.0 fold, and 8.5 fold that of mU6-TuD-NC, respectively. On the other hand, h7SK-TuD-NC was nearly equivalent. Furthermore, 1 ng transfection exhibited an effect that is little different from the 10 ng result (FIG. 28C). The above-mentioned results showed that introduction of a small amount of TuD-220c may sufficiently inhibit endogenous miR-200. miR-200 experiments also indicate that the mU6 promoter, h7SK promoter, and RuD-miR200C-4ntin-3L, TuD-miR200c-4ntin-3pL all showed high inhibitory activities.

Furthermore, when luciferase reporter assay was performed 23 days after viral transduction in cells stably expressing TuD RNA produced by introducing the TuD-miR200c expression lentiviral vector, mU6-TuD-miR200c-4ntin-3L-expressing cells and h7SK-TuD-miR200c-4ntin-3pL-expressing cells respectively increased the miR200c reporter expression by approximately 6.9 fold and 6.9 fold that of mU6-TuD-NC-expressing cells. On the other hand, h7SK-TuD-NC-expressing cells were nearly equivalent (FIG. 28D). These results showed that miR-200 can be inhibited for a long time with high efficiency using TuD-miR200c expression lentiviral vectors.

Induction of Epithelial-Mesenchymal Transformation by miR200 Inhibition

The miRNA-inhibiting RNA expression lentiviral vectors, pLCG-mU6-TuD-miR200c-4ntin-3L, pLCG-mU6-TuD-NC, pLCG-h7SK-TuD-miR200c-4ntin-3pL, and pLCG-h7SK-TuD-NC were each introduced into HCT116 cells which are epithelial cells, and GFP-expressing cells were fractionated. Proteins of these cells were collected, and the expression levels of E-cadherin and vimentin which are gene markers of epithelial cells and mesenchymal cells were analyzed by Western blotting. The expression level of E-cadherin was remarkably decreased in cells transfected with pLCG-mU6-TuD-miR200c-4ntin-3L or pLCG-h7SK-TuD-miR200c-4ntin-3pL compared to cells transfected with pLCG-mU6-TuD-NC or pLCG-h7SK-TuD-NC (FIG. 28E). While the expression of vimentin was not observed in cells transfected with pLCG-mU6-TuD-NC or pLCG-h7SK-TuD-NC, it was expressed in cells transfected with pLCG-mU6-TuD-miR200c-4ntin-3L or pLCG-h7SK-TuD-miR200c-4ntin-3pL (FIG. 28E). The above-mentioned results indicate that as result of TuD-miR200c-mediated inhibition of the miR-200 family, HCT116 which are epithelial cells were transformed into mesenchymal cells.

Example 11 miRNA Inhibition Using Synthetic Oligonucleotides 1.1 miRNA Inhibitors

For the preparation of S-TuD RNA (FIG. 31(B) type), a series of fully 2'-O-methylated RNA oligonucleotide pairs listed below were synthesized and each pair was annealed before transfection.

2'-O-Methylated RNA oligo pairs for S-TuD preparation

S-TuD-miR21-pf:
(sense, SEQ ID NO: 185)
5'-gacggcgcuaggaucaucaacucaacaucagucugauaagcuaca
aguauucuggu-3',
and (antisense, SEQ ID NO: 186)
5'-accagaauacaacucaacaucagucugauaagcuacaagaugauc
cuagcgccguc-3'

S-TuD-miR21-4ntin:
(sense, SEQ ID NO: 148)
5'-gacggcgcuaggaucaucaacucaacaucagucaaugugauaagc
uacaaguauucuggu-3',
and (antisense, SEQ ID NO: 149)
5'-accagaauacaacucaacaucagucaaugugauaagcuacaagau
gauccuagcgccguc-3'

S-TuD-miR21-10mut:
(sense, SEQ ID NO: 187)
5'-gacggcgcuaggaucaucaacucaacaucaguccgauaagcuaca
aguauucuggu-3',
and (antisense, SEQ ID NO: 188)
5'-accagaauacaacucaacaucaguccgauaagcuacaagaugauc
cuagcgccguc-3'

S-TuD-miR200c-pf:
(sense, SEQ ID NO: 189)
5'-gacggcgcuaggaucaucaacuccaucauuacccggcaguauuac
aaguauucuggu-3',
and (antisense, SEQ ID NO: 190)
5'-accagaauacaacuccaucauuacccggcaguauuacaagaugau
ccuagcgccguc-3'

S-TuD-miR200c-4ntin-CACU:
(sense, SEQ ID NO: 191)
5'-gacggcgcuaggaucaucaacuccaucauuaccccacuggcagua
uuacaaguauucuggu-3',
and (antisense, SEQ ID NO: 192)
5'-accagaauacaacuccaucauuaccccacuggcaguauuacaaga
ugauccuagcgccguc-3'

S-TuD-miR200c-4ntin-AUUA:
(sense, SEQ ID NO: 193)
5'-gacggcgcuaggaucaucaacuccaucauuacccauuaggcagua
uuacaaguauucuggu-3',
and (antisense, SEQ ID NO: 194)
5'-accagaauacaacuccaucauuacccauuaggcaguauuacaaga
ugauccuagcgccguc-3'

S-TuD-miR200c-10mut:
(sense, SEQ ID NO: 195)
5'-gacggcgcuaggaucaucaacuccaucauuacccagcaguauuac
aaguauucuggu-3',
and (antisense, SEQ ID NO: 196)
5'-accagaauacaacuccaucauuacccagcaguauuacaagaugau
ccuagcgccguc-3'

S-TuD-miR16-pf:
(sense, SEQ ID NO: 197)
5'-gacggcgcuaggaucaucaaccgccaauauuuacgugcugcuaca
aguauucuggu-3',
and (antisense, SEQ ID NO: 198)
5'-accagaauacaaccgccaauauuuacgugcugcuacaagaugauc
cuagcgccguc-3'

S-TuD-miR16-4ntin:
(sense, SEQ ID NO: 199)
5'-gacggcgcuaggaucaucaaccgccaauauuuaguuccgugcugc
uacaaguauucuggu-3',
and (antisense, SEQ ID NO: 200)
5'-accagaauacaaccgccaauauuuaguuccgugcugcuacaagau
gauccuagcgccguc-3'

S-TuD-miR16-10mut-CtoU:
(sense, SEQ ID NO: 201)
5'-gacggcgcuaggaucaucaaccgccaauauuuaugugcugcuaca
aguauucuggu-3',
and (antisense, SEQ ID NO: 202)
5'-accagaauacaaccgccaauauuuaugugcugcuacaagaugauc
cuagcgccguc-3'

S-TuD-miR16-10mut-CtoA:
(sense, SEQ ID NO: 203)
5'-gacggcgcuaggaucaucaaccgccaauauuuaagugcugcuaca
aguauucuggu-3',
and (antisense, SEQ ID NO: 204)
5'-accagaauacaaccgccaauauuuaagugcugcuacaagaugauc
cuagcgccguc-3'

S-TuD-NC:
(sense, SEQ ID NO: 209)
5'-gacggcgcuaggaucaucaacuaucgcgaguaucgacgucgaggc
ccaaguauucuggu-3',
and (antisense, SEQ ID NO: 210)
5'-accagaauacaacuaucgcgaguaucgacgucgaggcccaagaug
auccuagcgccguc-3'

Anti-miR21 Hairpin-inhibitor (miRIDIAN-miR21) was purchased from Thermo Scientific (IH-300492-05). The anti-miR200c LNA oligonucleotide antisense (miRCURY-miR200c) was purchased from Exiqon (410126-00). Anti-miR21 PNA oligonucleotide antisense and negative control PNA oligonucleotide antisense were supplied from PANAGENE (PI-1050 and PN-1001, respectively). Negative control LNA/DNA oligonucleotides antisense was synthesized by GeneDesign. Negative control 2'-O-Methylated RNA oligonucleotides antisense and anti-miR21 2'-O-Methylated RNA oligonucleotide antisense were synthesized by Hokkaido System Science. Sequences of 2'-O-Methylated RNA AMOs and negative control LNA/DNA AMO are listed below.

Sequences of 2'-O-Methyl Antisense Oligos and LNA/DNA Antisense Oligos

2'OMe-miR21: 5'-GUCAACAUCAGUCUGAUAAGCUA-3' (SEQ ID NO: 150; all of bases are 2'-O-Methylated RNA)

2'OMe-NC: 5'- AAGGCAAGCUGACCCUGAAGU -3' (SEQ ID NO: 151; all of bases are 2'-O-Methylated RNA)

LNA-NC: 5'-CATTAATGTCGGACAACTCAAT-3' (SEQ ID NO: 80; LNAs are indicated by underline and other bases are DNA)

1.2 Cell Culture and Construction of Stable Cell Line

Human colorectal adenocarcinoma cell lines, HCT-116 was obtained from ATCC. These cells were cultured at 37° C. in DMEM containing 10% foetal bovine serum (FBS). HCT-116 cells were seeded at $1 \times 10^5$ cells per well (six-well plates) and transduced with pMXs-GIN-miR-200cT (FIG. 29), viral stock (<1×10⁴ TU) in the presence of 8 μg/ml of Polybrene and selected with G418 (1 mg/ml) from 24 hours after the transfection. After 2 weeks of selection, the G418 was removed from the medium. By limiting dilutions, several stable clones were isolated and one clone designated as HCT-116-T200c, was used for GFP reporter analysis.

1.3 Plasmid Donstruction

For the construction of luciferase reporter plasmids, the oligonucleotide pairs, listed below were annealed and cloned into the XbaI-FseI sites of pGL4.74 (Promega) to generate pGL4.74-T21, pGL4.74-T200c, and pGL4.74-T16, respectively.

Primer Pairs Used for Luciferase Reporter Vectors

```
pGL4.74-T21:
                                  (sense, SEQ ID NO: 211)
5'-CTAGACCGGAATTCTCAACATCAGTCTGATAAGCTACTCGAGCGG
AGGCCGG-3',
and (antisense, SEQ ID NO: 212)
5'-CCTCCGCTCGAGTAGCTTATCAGACTGATGTTGAGAATTCCGG
T-3' pGL4.74-T200c:
                                  (sense, SEQ ID NO: 183)
5'-CTAGACCGGAATTCTCCATCATTACCCGGCAGTATTACTCGAGCG
GAGGCCGG-3',
and (antisense, SEQ ID NO: 184)
5'-CCTCCGCTCGAGTAATACTGCCGGGTAATGATGGAGAATTCCGG
T-3' pGL4.74-T16:
                                  (sense, SEQ ID NO: 213)
5'-CTAGACCGGAATTCCGCCAATATTTACGTGCTGCTACTCGAGCGG
AGGCCGG-3',
and (antisense, SEQ ID NO: 214)
5'-CCTCCGCTCGAGTAGCAGCACGTAAATATTGGCGGAATTCCGG
T-3'
```

For the construction of GFP reporter plasmids, the oligonucleotide pair listed below was annealed and cloned into the NotI-SalI sites of pMXs-GIN vector to generate pMXs-GIN-miR200cT (FIG. 29).

Primer Pairs Used for Reporter Vectors

```
pMXs-GIN-miR200cT:
                                  (sense, SEQ ID NO: 217)
5'-GGCCGCTTCCATCATTACCCGGCAGTATTAGGG-3',
and (antisense, SEQ ID NO: 218)
5'-TCGACCCTAATACTGCCGGGTAATGATGGAAGC-3'
```

For the construction of h7SK (human 7SK) promoter type miRNA-inhibiting RNA shuttle vector, 0.3-kb human 7SK promoter fragment was amplified by PCR from human genomic DNA using the primers listed below, followed by cloning into pCR2.1 (Invitrogen).

Primer Pairs Used for the Construction of h7SK Promoter TuD RNA Shuttle Vectors

```
h7SK promoter PCR:
                            (Forward primer, SEQ ID NO: 155)
5'-GGATCCTGCAGTATTTAGCATGCCCCA-3',
and (Reverse primer, SEQ ID NO: 156)
5'-GAATTCAAAAAAGGATGTGAGGGCGTCATCGAGACGGTACCGTCT
CCGATGACGCCCTCACATCCGAGGTACCCAGGCGGCGCACAAGC-3' h7SK TuD RNA shuttle:
                                  (sense, SEQ ID NO: 157)
5'-CTCGGATGTGAGGGCGTCATCGGAGACGACACCATCCACAGCCAG
CGTCTCGATGACGCCCTCACATCCTTTTTTGAATTCA-3',
and (antisense, SEQ ID NO: 158)
'-AGCTTGAATTCAAAAAAGGATGTGAGGGCGTCATCGAGACGCTGGC
TGTGGATGGTGTCGTCTCCGATGACGCCCTCACATCCGAGGTAC-3'
```

An oligo pair, listed above, was annealed and cloned into this product digested with KpnI and HindIII to generate ph7SK-TuD-shuttle. For the construction of miRNA-inhibiting RNA expression cassettes, a series of oligonucleotide pairs were synthesized as listed above. Each oligo pair was annealed and cloned into the ph7SK-TuD-shuttle digested with BsmBI and h7SK-TuD-miR200c and h7SK-TuD-NC cassettes, the 0.4kb BamHI-EcoRI fragments, were then subcloned into the lentivirus vector pLSP digested with BamHI and EcoRI to generate pLSP-h7SK-TuD-miR200c and pLSP-h7SK-TuD-NC, respectively.

1.4 Transfection and Luciferase Assays

Cells were seeded at densities of 1.0×10⁵ cells per well in 24-well plates in DMEM containing 10% foetal bovine serum (FBS) the day before transfection. The cells were transfected in triplicate with Lipofectamine 2000 (Invitrogen) and 10 ng of Firefly luciferase plasmid pTK4.12 (FIG. 30A), 100 ng of RLuc target reporter plasmid and various concentrations of miRNA inhibitors (0.003 and 25 nM) (FIG. 30B-E). All assays were performed at 48 h after the transfection using the dual luciferase assay (Promega, Madison, Wis.) on GLO-MAX (Promega).

1.5 Oligonucleotides Transfection, FACS Analysis and Sorting

HCT-116-200cT cells were seeded at 1×10⁵ cells per well (six-well plates) in DMEM containing 10% foetal bovine serum (FBS). After 24 hours, the cells were transfected with 1-50 nM of S-TuD-miR200c-pf using siPORT NeoFX transfection reagent (Ambion) according to manufacturer's instructions. The GFP expression profiles were measured using FACS BD-LSR (BD). To specifically isolate miRNA inhibitor transfected cells, cells expressing GFP at high levels were sorted using FACS Aria (BD).

Results

Synthesis of Two Modified RNA Strands that Form a Structure Resembling TuD-miR21-4ntin After Hybridization Among several TuD-miR21s described above, TuD-miR21 with 4 nt insertion between position 10 and 11 from the 3'end of the perfect complementary MBS where the RISC cleaves the target mRNAs (TuD-miR21-4ntin) exhibited most potent inhibitory effects when expressed by plasmid vectors. Therefore synthetic 2'-O-Methylated RNA oligonucleotides that have the same sequence to that of TuD-miR21-4ntin may also work well. However, the synthesis of the full length molecule of TuD-miR21-4ntin (122 nucleotides) in large amounts would not be most cost-effective. Considering that the both sides of the two MBS sequences in an miRNA-inhibiting RNA molecule are flanked by two dsRNA stems, it should be possible to separate the entire TuD-miR21-4ntin molecule into 2 strands (60 nucleotides each) by cutting at the middle of the loop region so that the structure formed after the hybridization of both strands resemble the structure of TuD-miR21-4ntin (FIG. 31B).

To confirm that such hybridized 2'-O-Methylated RNA suppresses endogenous miR-21 activity in HCT-116 cells (expressing high levels of miR-21), the two-strand type TuD-miR21-4ntin (S-TuD-miR21-4ntin) was transiently cotransfected with Dual Luciferase Reporters (DLR), which are composed of the *Renilla* luciferase reporter with or without the insertion of a 22-bp DNA sequence fully complementary to the mature miR-21 into its 3'-UTR as well as the Firefly luciferase reporter as a transfection control (FIG. 30A-C and FIG. 31C). It inhibited the endogenous miR-21 activity much more efficiently than the conventional 2'-O-Methylated RNA oligonucleotides AMO, when 1-3 nM of the inhibitors were introduced, respectively. Significant inhibitory effects of AMO were observed only at the concentration of 50-200 nM (FIG. 32). This 2'-O-Methylated ribonucleotide-based inhibitor of miRNA was further modified to optimize the inhibitory effects as described below.

Modulation of MBS Sequence of S-TuD for the Optimum Inhibitory Effects

TuD-miR21-4ntin has two miRNA binding sites (MBS) which carry a 4nt-insertion between positions 10 and 11 from the 3' end of the perfectly complementary sequence to miR-21, where RISCs cleave the target mRNAs. This insertion sequence is designed to form a 4nt-bulge when the target miRNA binds to the MBS of the corresponding miRNA inhibitor. By the presence of this bulge, TuD-miR21-4ntin efficiently escaped from the cleavage and has much higher inhibitory effect than TuD-miR21-pf (TuD-miR21 harboring MBSs perfectly complementary to miR-21). Since the synthesized miRNA inhibitor is composed of fully 2'-O-Methylated RNA, it would be very possible that this 4nt insertion is not required to escape from the cleavage. To confirm the effect of the 4nt insertion, inhibitory effects of the synthesized miRNA inhibitor carrying MBSs with or without a 4nt-bulge was compared to each other, using synthetic miRNA inhibitors targeting miR-21 and miR-200c, respectively. Whereas S-TuD-miR21-4ntin inhibited miR-21 more efficiently than S-TuD-miR2l-pf at the same dosage (FIG. 33A), inhibitory effect by 0.1 nM S-TuD-miR200c-pf was even higher than that by 0.3 nM S-TuD-miR200c-4ntin (FIG. 33B).

To further analyze the requirement of the bulge for the potent inhibitory effect, possible secondary structures of these synthetic miRNA inhibitors were constructed using CentroidFold (www.ncrna.org/centroidfold; Computational Biology Research Center (CBRC), Tokyo, Japan). Since CentroidFold supports prediction of secondary structure composed of a single RNA molecule but not that composed of two strands of 2'-O-Methylated RNA molecules, the single stranded miRNA inhibitor that has the same MBS sequences as the corresponding double stranded miRNA inhibitor, to obtain approximate secondary structures of these molecules (FIG. 34).

When the base-pair formation between the two MBSs in the miRNA inhibitors targeting miR-21 were compared, it was much stronger in S-TuD-miR2l-pf than in S-TuD-miR21-4ntin. Interaction between the two MBSs of S-TuD-miR200c-4ntin is much stronger than that of S-TuD-miR200c-pf. From these observations, it is suggested that the stronger the interaction between the two MBSs of the inhibitor RNA molecule, the weaker the accessibility to the target miRNA. To confirm this, a point mutation was introduced in MBSs to reduce the base-pair formation between the two MBSs of S-TuD-miR21-pf. Because of the presence of linker sequences that flank MBSs, regions close to the 5' end or 3' end of MBS would not be tend to form base pairing. Since point mutations at positions complementary to the seed or 3' compensatory regions would drastically reduce miRNA inhibitory effects, a point mutation was introduced at the middle region of MBS. A synthesized S-TuD-miR21 with MBS mutated at position 10 from the 3' end of MBS, S-TuD-miR21-10mut, consists of the two MBSs which would form less base paring compared with those of S-TuD-miR21-pf (FIG. 34). When miRNA inhibitory effects of S-TuD-miR21-pf, S-TuD-miR21-4ntin and S-TuD-miR21-10mut were tested (FIG. 33A), S-TuD-miR21-10mut was much more efficient as expected. In a case of miR-200c, however, S-TuD-miR200c-pf was found to be more inhibitory than S-TuD-miR200c-10mut (FIG. 33B). It may be because both S-TuD-miR200c-pf and S-TuD-miR200c-10mut did not form significant base-pairing between the two MBS sequences. In such cases, the presence of mismatch between MBS and miRNA would rather reduce inhibitory effects.

These results suggest that for the optimum conditions for designing an efficient miRNA-inhibiting molecule, two MBSs in it should not significantly form base pairs. If MBS perfectly complementary to miRNA does not satisfy this, introduction of a point mutation in the middle region or 1 to 4 nt insertion would be one way to improve the inhibitory effects of miRNA-inhibiting molecules, even considering the possible loss of binding affinity. For example, in the case of S-TuD-miR16-pf, S-TuD-miR16-4ntin and S-TuD-miR16-10mut (FIG. 34), the two MBS of which do not form strong base-pairing, S-TuD-miR16-pf was shown to be the most efficient inhibitor as expected when tested by miR-16 luciferase reporter system (FIG. 33C). However, it should be understood that the present invention is not limited to the particular conditions described above, and that the miRNA inhibiting molecules of the present invention that fall outside of the conditions also exhibit significant miRNA-inhibiting activities and are within the scope of the present invention.

Dose Dependency on the miRNA Inhibitory Activity

The dose response of the miRNA-inhibiting RNAs targeting miR-21 and miR-200c on their corresponding miRNAs were determined. The dose dependency of S-TuD-miR21-10mut as well as of 2'-O-methylated RNA based Hairpin-inhibitor targeting miR-21 was investigated (FIG. 35A). S-TuD-miR21-10mut showed inhibitory effects at the concentration of 0.2 nM and they reached the saturation levels, which almost correspond to luciferase activity of the reporter without perfect complementary insertion to miR-21 at the concentration of 5 nM. On the other hand, Hairpin-inhibitor-miR21 showed inhibitory effects at the concentration of 1 nM and they saturated at the concentration of 25 nM.

Next, the dose dependency of S-TuD-miR200c-pf and LNA oligonucleotides antisense inhibitor targeting miR-200c was determined (FIG. 35B). S-TuD-miR200c-pf showed inhibitory effects at the concentration of 0.003 nM and inhibitory effects were saturated at the concentration of 0.3 nM, whereas inhibitory effects of LNA-miR200c did not reach saturation point even at the concentration of 3 nM. These results show that synthetic miRNA-inhibitors of the present invention inhibit target miRNA by transfection at very high efficiencies.

As described above, if the miRNA-inhibiting RNA is composed of native RNA, it is preferable that MBS sequence has 4nt insertion into perfect complementary sequence to target miRNA to escape from cleavage by RISC containing Ago2. However, when the miRNA-inhibiting molecule is composed of modified RNA, this insertion sequence is not required to improve the inhibitory activity, because, unlike native RNA, the modified RNA such as 2'-O-Methylated RNA was resistant to the cleavage. By testing several MBS sequences, the inventors have found that the two MBSs within a single molecule of the miRNA-inhibiting RNA should not form significant number of base-pairs (preferably, the base-paring within the MBS should be less than 9) when assessed by Centroid-Fold. Although secondary structure composed of 2'-O-Methylated RNA would be different from that composed of native RNA, the inventors have found that inhibitory activity of a 2'-O-Methylated miRNA-inhibiting RNA molecule and the predicted secondary structure formed between their two MBSs had relatively good correlation. The miRNA-inhibiting RNA of the present invention showed highly efficient inhibitory activity even at very low concentrations compared with other currently available inhibitors. Considering these characteristics, the present invention will make a significant contribution to provide not only very useful tools for miRNA research but also promising therapeutics drugs.

Example 12

Duration of the Inhibitory Effect of the miRNA-Inhibiting RNAs

The duration of the inhibitory effect of the synthetic miRNA-inhibiting RNAs was investigated. A retrovirus-based GFP reporter vector harbouring a 23bp insert downstream of the GFP gene that was fully complementary to the mature miR-200c was used to evaluate the miRNA-inhibiting activity. HCT116 was transduced with the reporter vector to obtain a clone designated the HCT-116-200cT, which could be used as a sensitive assay system for miR-200c activity. This cell clone was transfected with S-TuD-miR200c-pf or S-TuD-NC at the concentrations of 1 or 5 nM, and GFP expression levels were measured by FACS 2 days after transfection and sorted the cellular fraction expressing higher GFP than untransfected cells. The GFP expressing cells from S-TuD-NC transfected cells were also sorted as negative control. These sorted cells were cultured and GFP expression levels were measured at the time indicated (FIG. 36). Oligonucleotides transfection, FACS analysis and sorting were performed as described in section 1.5 of Example 11.

The inhibitory effect of S-TuD-miR200c-pf was very high 2 days after the transfection and significant inhibitory effect was maintained even 7 days after transfection. Furthermore, the inhibitory effect was observed 9-11 days after transfection and marginal inhibitory effect was observed 13-15 days after transfection. The inhibitory effect of S-TuD-miR200c-pf disappeared completely 17 days after transfection. These results indicated that the inhibitory effect of the chemically synthesized miRNA-inhibiting RNA is long-lasting and is tolerable after several round of cell division.

INDUSTRIAL APPLICABILITY

The present invention provides miRNA inhibitor complexes that can efficiently and specifically inhibit miRNAs. The miRNA inhibitor complexes of the present invention can stably inhibit miRNA for a long time, for example, by retroviral vector expression, and enable, for example, in vivo assays such as knockdown mouse. Furthermore, miRNA knockdown can be carried out in a time- and tissue-specific manner using Cre-loxP. As exemplified in FIG. 6, expression cassettes for miRNA-inhibiting RNAs of the present invention can be constructed easily. Therefore, an RNA library for comprehensive analysis of miRNAs can be constructed. This way, the present invention provides tools that are very useful for studying miRNAs. Furthermore, a significant proportion of genes in a living body are predicted to be targets of miRNAs, and miRNAs have been suggested to play important roles in various scenes including differentiation, development, tumorigenesis, and cellular defense against infections. The methods of the present invention are useful for regulating functions of miRNAs in gene therapy and such for tumors and infections, and elucidating gene regulatory mechanisms.

What is claimed is:

1. An isolated miRNA-inhibiting complex comprising an RNA or analog thereof, which comprises:
   (a) a double-stranded structure
   (b) a multiple-stranded structure, and
   (c) a plurality of strands that each comprise an miRNA-binding sequence, wherein the strands are each bound at one end to one of two strands on one end of said double-stranded structure, and wherein the other ends of the strands are each bound to one of two strands of the multiple-stranded structure, so that the strands are placed between the double-stranded structure and the multiple-stranded structure.

2. The complex of claim 1, wherein the multiple-stranded structure is a double or quadruple strand.

3. The complex of claim 1, wherein the two strands on one end of said double-stranded structure are linked together.

4. The complex of claim 3, which is composed of a single-stranded linear RNA or analog thereof.

5. The complex of claim 1, which is composed of two single-stranded linear RNAs or analogs thereof.

6. The complex of claim 1, which comprises two to five miRNA-binding sequences.

7. The complex of claim 6, which comprises two miRNA-binding sequences.

8. The complex of claim 1, which comprises a structure shown in FIG. 2(C), wherein I and II of the structure is double-stranded, and wherein each of a and b of the structure comprises an miRNA-binding sequence.

9. The complex of claim 4, which comprises a structure shown in FIG. 2(D), wherein I of the structure is double-stranded and the end of each strand is present on one side of I, and wherein II of the structure is a hairpin, and each of a and b of the structure comprises an miRNA-binding sequence.

10. An isolated RNA or analog thereof which composes an miRNA-inhibiting complex comprising an RNA or analog thereof, which comprises:
   (a) a double-stranded structure
   (b) a multiple-stranded structure, and
   (c) a plurality of strands that each comprise an miRNA-binding sequence, wherein the strands are each bound at one end to one of two strands on one end of said double-stranded structure, and wherein the other ends of the strands are each bound to one of two strands of the multiple-stranded structure, so that the strands are placed between the double-stranded structure and the multiple-stranded structure.

11. An isolated nucleic acid which encodes an RNA or analog thereof which composes an miRNA-inhibiting complex comprising an RNA or analog thereof, which comprises:
   (a) a double-stranded structure
   (b) a multiple-stranded structure, and
   (c) a plurality of strands that each comprise an miRNA-binding sequence, wherein the strands are each bound at one end to one of two strands on one end of said double-stranded structure, and wherein the other ends of the strands are each bound to one of two strands of the multiple-stranded structure, so that the strands are placed between the double-stranded structure and the multiple-stranded structure.

12. The nucleic acid of claim 11, which is bound downstream of a promoter.

13. The nucleic acid of claim 12, wherein the promoter is a polymerase III promoter.

14. The nucleic acid of claim 12, which is carried by a retroviral vector.

15. The nucleic acid of claim 11, wherein the promoter is a polymerase II promoter.

16. The complex of claim 1, wherein the complex comprises equivalent miRNA-binding sequences.

17. The complex of claim 1, wherein the complex comprises different miRNA-binding sequences.

* * * * *

SEQUENCE LISTING

```
<160> NUMBER OF SEQ ID NOS: 222

<210> SEQ ID NO 1
<211> LENGTH: 31
<212> TYPE: DNA
<213> ORGANISM: Artificial
<220> FEATURE:
<223> OTHER INFORMATION: an artificially synthesized sequence

<400> SEQUENCE: 1
ggccgctccg tggttctacc ctgtggtagg g                              31

<210> SEQ ID NO 2
<211> LENGTH: 31
<212> TYPE: DNA
<213> ORGANISM: Artificial
<220> FEATURE:
<223> OTHER INFORMATION: an artificially synthesized sequence

<400> SEQUENCE: 2
tcgaccctac cacagggtag aaccacggag c                              31

<210> SEQ ID NO 3
<211> LENGTH: 32
<212> TYPE: DNA
<213> ORGANISM: Artificial
<220> FEATURE:
<223> OTHER INFORMATION: an artificially synthesized sequence
```

```
<400> SEQUENCE: 3
ggccgctcta ccatagggta aaaccactgg gg                                32

<210> SEQ ID NO 4
<211> LENGTH: 32
<212> TYPE: DNA
<213> ORGANISM: Artificial
<220> FEATURE:
<223> OTHER INFORMATION: an artificially synthesized sequence

<400> SEQUENCE: 4 tcgacccag tggttttacc ctatggtaga gc                                 32

<210> SEQ ID NO 5
<211> LENGTH: 20
<212> TYPE: DNA
<213> ORGANISM: Artificial
<220> FEATURE:
<223> OTHER INFORMATION: an artificially synthesized sequence

<400> SEQUENCE: 5
tgcttgctgg tggtgtagtc                                              20

<210> SEQ ID NO 6
<211> LENGTH: 20
<212> TYPE: DNA
<213> ORGANISM: Artificial
<220> FEATURE:
<223> OTHER INFORMATION: an artificially synthesized sequence

<400> SEQUENCE: 6
accaacaccc acccaataga                                              20

<210> SEQ ID NO 7
<211> LENGTH: 63
<212> TYPE: DNA
<213> ORGANISM: Artificial
<220> FEATURE:
<223> OTHER INFORMATION: an artificially synthesized sequence

<400> SEQUENCE: 7
tttgacggcg ctaggatcat cggagacggt accgtctcga tgatcctagc gccgtctttt  60
ttg                                                                63

<210> SEQ ID NO 8
<211> LENGTH: 63
<212> TYPE: DNA
<213> ORGANISM: Artificial
<220> FEATURE:
<223> OTHER INFORMATION: an artificially synthesized sequence

<400> SEQUENCE: 8
aattcaaaaa agacggcgct aggatcatcg agacggtacc gtctccgatg atcctagcgc  60
cgt                                                                63

<210> SEQ ID NO 9
<211> LENGTH: 64
<212> TYPE: DNA
<213> ORGANISM: Artificial
<220> FEATURE:
<223> OTHER INFORMATION: an artificially synthesized sequence

<400> SEQUENCE: 9
tttgacggcg ctaggatcat cggagacggt accgtctccg atgatcctag cgccgtcttt  60
```

```
tttg                                                              64

<210> SEQ ID NO 10
<211> LENGTH: 64
<212> TYPE: DNA
<213> ORGANISM: Artificial
<220> FEATURE:
<223> OTHER INFORMATION: an artificially synthesized sequence

<400> SEQUENCE: 10
aattcaaaaa agacggcgct aggatcatcg gagacggtac cgtctccgat gatcctagcg   60
ccgt                                                              64

<210> SEQ ID NO 11
<211> LENGTH: 89
<212> TYPE: DNA
<213> ORGANISM: Artificial
<220> FEATURE:
<223> OTHER INFORMATION: an artificially synthesized sequence

<400> SEQUENCE: 11
catcaaccta ccatagggtc atcaaaacca ctgcaagtat tctggtcaca gaatacaacc   60 taccatagggg tcatcaaaac cactgcaag                                   89

<210> SEQ ID NO 12
<211> LENGTH: 89
<212> TYPE: DNA
<213> ORGANISM: Artificial
<220> FEATURE:
<223> OTHER INFORMATION: an artificially synthesized sequence

<400> SEQUENCE: 12
tcatcttgca gtggttttga tgaccctatg gtaggttgta ttctgtgacc agaatacttg   60
cagtggtttt gatgaccta tggtaggtt                                     89

<210> SEQ ID NO 13
<211> LENGTH: 89
<212> TYPE: DNA
<213> ORGANISM: Artificial
<220> FEATURE:
<223> OTHER INFORMATION: an artificially synthesized sequence

<400> SEQUENCE: 13
catcaactcc gtggttctaa tctccctgtg gtacaagtat tctggtcaca gaatacaact   60
ccgtggttct aatctccctg tggtacaag                                    89

<210> SEQ ID NO 14
<211> LENGTH: 89
<212> TYPE: DNA
<213> ORGANISM: Artificial
<220> FEATURE:
<223> OTHER INFORMATION: an artificially synthesized sequence

<400> SEQUENCE: 14
tcatcttgta ccacagggag attagaacca cggagttgta ttctgtgacc agaatacttg   60
taccacaggg agattagaac cacggagtt                                    89

<210> SEQ ID NO 15
<211> LENGTH: 80
<212> TYPE: DNA
<213> ORGANISM: Artificial
<220> FEATURE:
<223> OTHER INFORMATION: an artificially synthesized sequence
```

```
<400> SEQUENCE: 15
catcaactcc gtggttctac cctgtggtac aagtattctg gtcacagaat acaactccgt    60
ggttctaccc tgtggtacaa                                                80

<210> SEQ ID NO 16
<211> LENGTH: 80
<212> TYPE: DNA
<213> ORGANISM: Artificial
<220> FEATURE:
<223> OTHER INFORMATION: an artificially synthesized sequence

<400> SEQUENCE: 16
catcttgtac cacagggtag aaccacggag ttgtattctg tgaccagaat acttgtacca    60
cagggtagaa ccacggagtt                                                80

<210> SEQ ID NO 17
<211> LENGTH: 89
<212> TYPE: DNA
<213> ORGANISM: Artificial
<220> FEATURE:
<223> OTHER INFORMATION: an artificially synthesized sequence

<400> SEQUENCE: 17
catcaactca acatcagtca atgtgataag ctacaagtat tctggtcaca gaatacaact    60
caacatcagt caatgtgata agctacaag                                      89

<210> SEQ ID NO 18
<211> LENGTH: 89
<212> TYPE: DNA
<213> ORGANISM: Artificial
<220> FEATURE:
<223> OTHER INFORMATION: an artificially synthesized sequence

<400> SEQUENCE: 18
tcatcttgta gcttatcaca ttgactgatg ttgagttgta ttctgtgacc agaatacttg    60
tagcttatca cattgactga tgttgagtt                                      89

<210> SEQ ID NO 19
<211> LENGTH: 81
<212> TYPE: DNA
<213> ORGANISM: Artificial
<220> FEATURE:
<223> OTHER INFORMATION: an artificially synthesized sequence

<400> SEQUENCE: 19
catcaactca acatcagtct gataagctac aagtattctg gtcacagaat acaactcaac    60
atcagtctga taagctacaa g                                              81

<210> SEQ ID NO 20
<211> LENGTH: 81
<212> TYPE: DNA
<213> ORGANISM: Artificial
<220> FEATURE:
<223> OTHER INFORMATION: an artificially synthesized sequence

<400> SEQUENCE: 20
tcatcttgta gcttatcaga ctgatgttga gttgtattct gtgaccagaa tacttgtagc    60
ttatcagact gatgttgagt t                                              81

<210> SEQ ID NO 21
<211> LENGTH: 87
```

```
<212> TYPE: DNA
<213> ORGANISM: Artificial
<220> FEATURE:
<223> OTHER INFORMATION: an artificially synthesized sequence

<400> SEQUENCE: 21
catcaacaag ccacaacgaa tctctatatc atcaagtatt ctggtcacag aatacaacaa      60
gccacaacga atctctatat catcaag                                         87

<210> SEQ ID NO 22
<211> LENGTH: 87
<212> TYPE: DNA
<213> ORGANISM: Artificial
<220> FEATURE:
<223> OTHER INFORMATION: an artificially synthesized sequence

<400> SEQUENCE: 22
tcatcttgat gatatagaga ttcgttgtgg cttgttgtat tctgtgacca gaatacttga      60
tgatatagag attcgttgtg gcttgtt                                         87

<210> SEQ ID NO 23
<211> LENGTH: 72
<212> TYPE: DNA
<213> ORGANISM: Artificial
<220> FEATURE:
<223> OTHER INFORMATION: an artificially synthesized sequence

<400> SEQUENCE: 23
tttgacggcg ctggatgctt ggatccgtgg ttctaccctg tggtaaggaa gcatccagcg      60
ccgtcttttt tg                                                         72

<210> SEQ ID NO 24
<211> LENGTH: 72
<212> TYPE: DNA
<213> ORGANISM: Artificial
<220> FEATURE:
<223> OTHER INFORMATION: an artificially synthesized sequence

<400> SEQUENCE: 24
aattcaaaaa agacggcgct ggatgcttcc ttaccacagg gtagaaccac ggatccaagc      60
atccagcgcc gt                                                         72

<210> SEQ ID NO 25
<211> LENGTH: 74
<212> TYPE: DNA
<213> ORGANISM: Artificial
<220> FEATURE:
<223> OTHER INFORMATION: an artificially synthesized sequence

<400> SEQUENCE: 25
tttgacggcg ctaggatgct tggatccgtg gttctaccct gtggtaagga agcatcctag      60
cgccgtcttt tttg                                                       74

<210> SEQ ID NO 26
<211> LENGTH: 74
<212> TYPE: DNA
<213> ORGANISM: Artificial
<220> FEATURE:
<223> OTHER INFORMATION: an artificially synthesized sequence

<400> SEQUENCE: 26
aattcaaaaa agacggcgct aggatgcttc cttaccacag ggtagaacca cggatccaag      60
catcctagcg ccgt                                                       74
```

<210> SEQ ID NO 27
<211> LENGTH: 76
<212> TYPE: DNA
<213> ORGANISM: Artificial
<220> FEATURE:
<223> OTHER INFORMATION: an artificially synthesized sequence

<400> SEQUENCE: 27
tttgacagcg ctctacgatg aaggctccgt ggttctaccc tgtggtaagg ttcatcgtag    60
agcgctgtct tttttg                                                    76

<210> SEQ ID NO 28
<211> LENGTH: 76
<212> TYPE: DNA
<213> ORGANISM: Artificial
<220> FEATURE:
<223> OTHER INFORMATION: an artificially synthesized sequence

<400> SEQUENCE: 28
aattcaaaaa agacagcgct ctacgatgaa ccttaccaca gggtagaacc acggagcctt    60
catcgtagag cgctgt                                                    76

<210> SEQ ID NO 29
<211> LENGTH: 78
<212> TYPE: DNA
<213> ORGANISM: Artificial
<220> FEATURE:
<223> OTHER INFORMATION: an artificially synthesized sequence

<400> SEQUENCE: 29
tttgacagcg ctctacgatg caaggctccg tggttctacc ctgtggtaag gttgcatcgt    60
agagcgctgt ctttttg                                                   78

<210> SEQ ID NO 30
<211> LENGTH: 78
<212> TYPE: DNA
<213> ORGANISM: Artificial
<220> FEATURE:
<223> OTHER INFORMATION: an artificially synthesized sequence

<400> SEQUENCE: 30
aattcaaaaa agacagcgct ctacgatgca accttaccac agggtagaac cacggagcct    60
tgcatcgtag agcgctgt                                                  78

<210> SEQ ID NO 31
<211> LENGTH: 80
<212> TYPE: DNA
<213> ORGANISM: Artificial
<220> FEATURE:
<223> OTHER INFORMATION: an artificially synthesized sequence

<400> SEQUENCE: 31
tttgacagcg ctcgcaggat gcttggctcc gtggttctac cctgtggtaa ggaagcatcc    60
tgcgagcgct gtctttttg                                                 80

<210> SEQ ID NO 32
<211> LENGTH: 80
<212> TYPE: DNA
<213> ORGANISM: Artificial
<220> FEATURE:
<223> OTHER INFORMATION: an artificially synthesized sequence

<400> SEQUENCE: 32

-continued aattcaaaaa agacagcgct cgcaggatgc ttccttacca cagggtagaa ccacggagcc    60
aagcatcctg cgagcgctgt                                                80

<210> SEQ ID NO 33
<211> LENGTH: 86
<212> TYPE: DNA
<213> ORGANISM: Artificial
<220> FEATURE:
<223> OTHER INFORMATION: an artificially synthesized sequence

<400> SEQUENCE: 33
tttgacagcg ctcaaagcag gatgcttggc tccgtggttc taccctgtgg taaggaagca    60
tcctgctttg agcgctgtct tttttg                                         86

<210> SEQ ID NO 34
<211> LENGTH: 86
<212> TYPE: DNA
<213> ORGANISM: Artificial
<220> FEATURE:
<223> OTHER INFORMATION: an artificially synthesized sequence

<400> SEQUENCE: 34
aattcaaaaa agacagcgct caaagcagga tgcttcctta ccacagggta gaaccacgga    60
gccaagcatc ctgctttgag cgctgt                                         86

<210> SEQ ID NO 35
<211> LENGTH: 88
<212> TYPE: DNA
<213> ORGANISM: Artificial
<220> FEATURE:
<223> OTHER INFORMATION: an artificially synthesized sequence

<400> SEQUENCE: 35
tttgacggcg ctaggatcat ctccgtggtt ctaccctgtg gtagtattct ggtcacagaa    60
tacgatgatc ctagcgccgt ctttttg                                        88

<210> SEQ ID NO 36
<211> LENGTH: 88
<212> TYPE: DNA
<213> ORGANISM: Artificial
<220> FEATURE:
<223> OTHER INFORMATION: an artificially synthesized sequence

<400> SEQUENCE: 36
aattcaaaaa agacggcgct aggatcatcg tattctgtga ccagaatact accacagggt    60
agaaccacgg agatgatcct agcgccgt                                       88

<210> SEQ ID NO 37
<211> LENGTH: 108
<212> TYPE: DNA
<213> ORGANISM: Artificial
<220> FEATURE:
<223> OTHER INFORMATION: an artificially synthesized sequence

<400> SEQUENCE: 37
tttgacggcg ctaggatcat cgtattctgg tcacagaata ctccgtggtt ctaccctgtg    60
gtatcttctc taacgagaga agagatgatc ctagcgccgt ctttttg                  108

<210> SEQ ID NO 38
<211> LENGTH: 108
<212> TYPE: DNA
<213> ORGANISM: Artificial

```
<220> FEATURE:
<223> OTHER INFORMATION: an artificially synthesized sequence

<400> SEQUENCE: 38
aattcaaaaa agacggcgct aggatcatct cttctctcgt tagagaagat accacagggt      60
agaaccacgg agtattctgt gaccagaata cgatgatcct agcgccgt                  108

<210> SEQ ID NO 39
<211> LENGTH: 110
<212> TYPE: DNA
<213> ORGANISM: Artificial
<220> FEATURE:
<223> OTHER INFORMATION: an artificially synthesized sequence

<400> SEQUENCE: 39
tttgacggcg ctaggatcat ctccgtggtt ctaccctgtg gtagtattct ggtcacagaa     60
tactccgtgg ttctaccctg tggtagatga tcctagcgcc gtcttttttg               110

<210> SEQ ID NO 40
<211> LENGTH: 110
<212> TYPE: DNA
<213> ORGANISM: Artificial
<220> FEATURE:
<223> OTHER INFORMATION: an artificially synthesized sequence

<400> SEQUENCE: 40
aattcaaaaa agacggcgct aggatcatct accacagggt agaaccacgg agtattctgt     60
gaccagaata ctaccacagg gtagaaccac ggagatgatc ctagcgccgt               110

<210> SEQ ID NO 41
<211> LENGTH: 80
<212> TYPE: DNA
<213> ORGANISM: Artificial
<220> FEATURE:
<223> OTHER INFORMATION: an artificially synthesized sequence

<400> SEQUENCE: 41
catcaactcc gtggttctac cctgtggtac aagtattctg gtcacagaat acaactccgt     60
ggttctaccc tgtggtacaa                                                 80

<210> SEQ ID NO 42
<211> LENGTH: 80
<212> TYPE: DNA
<213> ORGANISM: Artificial
<220> FEATURE:
<223> OTHER INFORMATION: an artificially synthesized sequence

<400> SEQUENCE: 42
catcttgtac cacagggtag aaccacggag ttgtattctg tgaccagaat acttgtacca     60
cagggtagaa ccacggagtt                                                 80

<210> SEQ ID NO 43
<211> LENGTH: 92
<212> TYPE: DNA
<213> ORGANISM: Artificial
<220> FEATURE:
<223> OTHER INFORMATION: an artificially synthesized sequence

<400> SEQUENCE: 43
catctccgtg gttctaccct gtggtagtat tctgagatcc gtggttctac cctgtggtaa     60
gacagaatac tccgtggttc taccctgtgg ta                                   92
```

```
<210> SEQ ID NO 44
<211> LENGTH: 92
<212> TYPE: DNA
<213> ORGANISM: Artificial
<220> FEATURE:
<223> OTHER INFORMATION: an artificially synthesized sequence

<400> SEQUENCE: 44
catctaccac agggtagaac cacggagtat tctgtcttac cacagggtag aaccacggat      60
ctcagaatac taccacaggg tagaaccacg ga                                   92

<210> SEQ ID NO 45
<211> LENGTH: 128
<212> TYPE: DNA
<213> ORGANISM: Artificial
<220> FEATURE:
<223> OTHER INFORMATION: an artificially synthesized sequence

<400> SEQUENCE: 45
catctccgtg gttctaccct gtggtagtat tctgtccgtg gttctaccct gtggtagtat      60
tctggtcaca gaatactccg tggttctacc ctgtggtaca gaatactccg tggttctacc     120
ctgtggta                                                              128

<210> SEQ ID NO 46
<211> LENGTH: 128
<212> TYPE: DNA
<213> ORGANISM: Artificial
<220> FEATURE:
<223> OTHER INFORMATION: an artificially synthesized sequence

<400> SEQUENCE: 46
catctaccac agggtagaac cacggagtat tctgtaccac agggtagaac cacggagtat      60
tctgtgacca gaatactacc acagggtaga accacggaca gaatactacc acagggtaga     120
accacgga                                                              128

<210> SEQ ID NO 47
<211> LENGTH: 152
<212> TYPE: DNA
<213> ORGANISM: Artificial
<220> FEATURE:
<223> OTHER INFORMATION: an artificially synthesized sequence

<400> SEQUENCE: 47
catctccgtg gttctaccct gtggtagtat tctgtccgtg gttctaccct gtggtagtat      60
tctgagatcc gtggttctac cctgtggtaa gacagaatac tccgtggttc taccctgtgg     120
tacagaatac tccgtggttc taccctgtgg ta                                   152

<210> SEQ ID NO 48
<211> LENGTH: 152
<212> TYPE: DNA
<213> ORGANISM: Artificial
<220> FEATURE:
<223> OTHER INFORMATION: an artificially synthesized sequence

<400> SEQUENCE: 48
catctaccac agggtagaac cacggagtat tctgtaccac agggtagaac cacggagtat      60
tctgtcttac cacagggtag aaccacggat ctcagaatac taccacaggg tagaaccacg     120
gacagaatac taccacaggg tagaaccacg ga                                   152

<210> SEQ ID NO 49
<211> LENGTH: 75
```

```
<212> TYPE: DNA
<213> ORGANISM: Artificial
<220> FEATURE:
<223> OTHER INFORMATION: an artificially synthesized sequence

<400> SEQUENCE: 49
tttgacggcg ctaggatgct tgatccgtg gttctaaccc tgtggtaagg aagcatccta      60
gcgccgtctt ttttg                                                     75

<210> SEQ ID NO 50
<211> LENGTH: 75
<212> TYPE: DNA
<213> ORGANISM: Artificial
<220> FEATURE:
<223> OTHER INFORMATION: an artificially synthesized sequence

<400> SEQUENCE: 50
aattcaaaaa agacggcgct aggatgcttc cttaccacag ggttagaacc acggatccaa     60
gcatcctagc gccgt                                                     75

<210> SEQ ID NO 51
<211> LENGTH: 76
<212> TYPE: DNA
<213> ORGANISM: Artificial
<220> FEATURE:
<223> OTHER INFORMATION: an artificially synthesized sequence

<400> SEQUENCE: 51
tttgacggcg ctaggatgct tgatccgtg gttctaatcc ctgtggtaag gaagcatcct      60
agcgccgtct tttttg                                                    76

<210> SEQ ID NO 52
<211> LENGTH: 76
<212> TYPE: DNA
<213> ORGANISM: Artificial
<220> FEATURE:
<223> OTHER INFORMATION: an artificially synthesized sequence

<400> SEQUENCE: 52
aattcaaaaa agacggcgct aggatgcttc cttaccacag ggattagaac cacggatcca     60
agcatcctag cgccgt                                                    76

<210> SEQ ID NO 53
<211> LENGTH: 77
<212> TYPE: DNA
<213> ORGANISM: Artificial
<220> FEATURE:
<223> OTHER INFORMATION: an artificially synthesized sequence

<400> SEQUENCE: 53
tttgacggcg ctaggatgct tgatccgtg gttctaactc cctgtggtaa ggaagcatcc      60
tagcgccgtc ttttttg                                                   77

<210> SEQ ID NO 54
<211> LENGTH: 77
<212> TYPE: DNA
<213> ORGANISM: Artificial
<220> FEATURE:
<223> OTHER INFORMATION: an artificially synthesized sequence

<400> SEQUENCE: 54
aattcaaaaa agacggcgct aggatgcttc cttaccacag ggagttagaa ccacggatcc     60
aagcatccta gcgccgt                                                   77
```

<210> SEQ ID NO 55
<211> LENGTH: 78
<212> TYPE: DNA
<213> ORGANISM: Artificial
<220> FEATURE:
<223> OTHER INFORMATION: an artificially synthesized sequence

<400> SEQUENCE: 55
tttgacggcg ctaggatgct tggatccgtg gttctaatct ccctgtggta aggaagcatc    60
ctagcgccgt cttttttg                                                  78

<210> SEQ ID NO 56
<211> LENGTH: 78
<212> TYPE: DNA
<213> ORGANISM: Artificial
<220> FEATURE:
<223> OTHER INFORMATION: an artificially synthesized sequence

<400> SEQUENCE: 56
aattcaaaaa agacggcgct aggatgcttc cttaccacag ggagattaga accacggatc    60
caagcatcct agcgccgt                                                  78

<210> SEQ ID NO 57
<211> LENGTH: 78
<212> TYPE: DNA
<213> ORGANISM: Artificial
<220> FEATURE:
<223> OTHER INFORMATION: an artificially synthesized sequence

<400> SEQUENCE: 57
tttgacggcg ctaggatgct tccatcccag tacacattta aatctgtggt accaagcatc    60
ctagcgccgt cttttttg                                                  78

<210> SEQ ID NO 58
<211> LENGTH: 78
<212> TYPE: DNA
<213> ORGANISM: Artificial
<220> FEATURE:
<223> OTHER INFORMATION: an artificially synthesized sequence

<400> SEQUENCE: 58
aattcaaaaa agacggcgct aggatgcttg gtaccacaga tttaaatgtg tactgggatg    60
gaagcatcct agcgccgt                                                  78

<210> SEQ ID NO 59
<211> LENGTH: 81
<212> TYPE: DNA
<213> ORGANISM: Artificial
<220> FEATURE:
<223> OTHER INFORMATION: an artificially synthesized sequence

<400> SEQUENCE: 59
catcctccgt ggttctaatc tccctgtggt acgtattctg gtcacagaat acctccgtgg    60
ttctaatctc cctgtggtac g                                              81

<210> SEQ ID NO 60
<211> LENGTH: 81
<212> TYPE: DNA
<213> ORGANISM: Artificial
<220> FEATURE:
<223> OTHER INFORMATION: an artificially synthesized sequence

<400> SEQUENCE: 60

```
tcatcgtacc acagggagat tagaaccacg gaggtattct gtgaccagaa tacgtaccac    60
agggagatta gaaccacgga g                                              81

<210> SEQ ID NO 61
<211> LENGTH: 85
<212> TYPE: DNA
<213> ORGANISM: Artificial
<220> FEATURE:
<223> OTHER INFORMATION: an artificially synthesized sequence

<400> SEQUENCE: 61
catccctccg tggttctaat ctccctgtgg taccgtattc tggtcacaga ataccctccg    60
tggttctaat ctccctgtgg taccg                                          85

<210> SEQ ID NO 62
<211> LENGTH: 85
<212> TYPE: DNA
<213> ORGANISM: Artificial
<220> FEATURE:
<223> OTHER INFORMATION: an artificially synthesized sequence

<400> SEQUENCE: 62
tcatcggtac cacagggaga ttagaaccac ggagggtatt ctgtgaccag aatacggtac    60
cacagggaga ttagaaccac ggagg                                          85

<210> SEQ ID NO 63
<211> LENGTH: 89
<212> TYPE: DNA
<213> ORGANISM: Artificial
<220> FEATURE:
<223> OTHER INFORMATION: an artificially synthesized sequence

<400> SEQUENCE: 63
catcaactcc gtggttctaa tctccctgtg gtacaagtat tctggtcaca gaatacaact    60
ccgtggttct aatctccctg tggtacaag                                      89

<210> SEQ ID NO 64
<211> LENGTH: 89
<212> TYPE: DNA
<213> ORGANISM: Artificial
<220> FEATURE:
<223> OTHER INFORMATION: an artificially synthesized sequence

<400> SEQUENCE: 64
tcatcttgta ccacagggag attagaacca cggagttgta ttctgtgacc agaatacttg    60
taccacaggg agattagaac cacggagtt                                      89

<210> SEQ ID NO 65
<211> LENGTH: 93
<212> TYPE: DNA
<213> ORGANISM: Artificial
<220> FEATURE:
<223> OTHER INFORMATION: an artificially synthesized sequence

<400> SEQUENCE: 65
catcaccctc cgtggttcta atctccctgt ggtacccagt attctggtca cagaatacac    60
cctccgtggt tctaatctcc ctgtggtacc cag                                 93

<210> SEQ ID NO 66
<211> LENGTH: 93
<212> TYPE: DNA
<213> ORGANISM: Artificial
```

```
<220> FEATURE:
<223> OTHER INFORMATION: an artificially synthesized sequence

<400> SEQUENCE: 66
tcatctgggt accacaggga gattagaacc acggagggtg tattctgtga ccagaatact    60
gggtaccaca gggagattag aaccacggag ggt                                 93

<210> SEQ ID NO 67
<211> LENGTH: 97
<212> TYPE: DNA
<213> ORGANISM: Artificial
<220> FEATURE:
<223> OTHER INFORMATION: an artificially synthesized sequence

<400> SEQUENCE: 67
catcaaccct ccgtggttct aatctccctg tggtacccaa gtattctggt cacagaatac    60
aaccctccgt ggttctaatc tccctgtggt acccaag                             97

<210> SEQ ID NO 68
<211> LENGTH: 97
<212> TYPE: DNA
<213> ORGANISM: Artificial
<220> FEATURE:
<223> OTHER INFORMATION: an artificially synthesized sequence

<400> SEQUENCE: 68
tcatcttggg taccacaggg agattagaac cacggagggt tgtattctgt gaccagaata    60
cttgggtacc acaggagat tagaaccacg gagggtt                              97

<210> SEQ ID NO 69
<211> LENGTH: 119
<212> TYPE: DNA
<213> ORGANISM: Artificial
<220> FEATURE:
<223> OTHER INFORMATION: an artificially synthesized sequence

<400> SEQUENCE: 69
cgtctcacat caactccgtg gttctaatct ccctgtggta caagcgacaa gaactccgtg    60
gttctaatct ccctgtggta caagtattct gaactccgtg gttctaatct ccctgtggt    119

<210> SEQ ID NO 70
<211> LENGTH: 120
<212> TYPE: DNA
<213> ORGANISM: Artificial
<220> FEATURE:
<223> OTHER INFORMATION: an artificially synthesized sequence

<400> SEQUENCE: 70
cgtctcatca tcttgtacca caggagatt agaaccacgg agttgcgaca agttgtacca    60
cagggagatt agaaccacgg agttgtattc tgttgtacca cagggagatt agaaccacgg   120

<210> SEQ ID NO 71
<211> LENGTH: 106
<212> TYPE: DNA
<213> ORGANISM: Artificial
<220> FEATURE:
<223> OTHER INFORMATION: an artificially synthesized sequence

<400> SEQUENCE: 71
ctcgagtaac tcaacatcag gacataagct aagtctcaac atcaggacat aagctatcag    60
tcaacatcag gacataagct actgatcaac atcaggacat aagcta                  106
```

```
<210> SEQ ID NO 72
<211> LENGTH: 106
<212> TYPE: DNA
<213> ORGANISM: Artificial
<220> FEATURE:
<223> OTHER INFORMATION: an artificially synthesized sequence

<400> SEQUENCE: 72
accggttagc ttatgtcctg atgttgaccg atagcttatg tcctgatgtt gacagttagc    60
ttatgtcctg atgttgagtt ctagcttatg tcctgatgtt gatcag                  106

<210> SEQ ID NO 73
<211> LENGTH: 27
<212> TYPE: DNA
<213> ORGANISM: Artificial
<220> FEATURE:
<223> OTHER INFORMATION: an artificially synthesized sequence

<400> SEQUENCE: 73
agatctaatt catatttgca tgtcgct                                        27

<210> SEQ ID NO 74
<211> LENGTH: 63
<212> TYPE: DNA
<213> ORGANISM: Artificial
<220> FEATURE:
<223> OTHER INFORMATION: an artificially synthesized sequence

<400> SEQUENCE: 74
gaattcaaaa aatagcttat gtcctgatgt tgaggatccg agtggtctca tacagaactt    60
ata                                                                  63

<210> SEQ ID NO 75
<211> LENGTH: 19
<212> TYPE: DNA
<213> ORGANISM: Artificial
<220> FEATURE:
<223> OTHER INFORMATION: an artificially synthesized sequence

<400> SEQUENCE: 75
aattaataat gactcgagt                                                 19

<210> SEQ ID NO 76
<211> LENGTH: 19
<212> TYPE: DNA
<213> ORGANISM: Artificial
<220> FEATURE:
<223> OTHER INFORMATION: an artificially synthesized sequence

<400> SEQUENCE: 76
ctagactcga gtcattatt                                                 19

<210> SEQ ID NO 77
<211> LENGTH: 28
<212> TYPE: DNA
<213> ORGANISM: Artificial
<220> FEATURE:
<223> OTHER INFORMATION: an artificially synthesized sequence

<400> SEQUENCE: 77
aattctcaac atcagtctga taagctac                                       28

<210> SEQ ID NO 78
<211> LENGTH: 29
<212> TYPE: DNA
<213> ORGANISM: Artificial
```

```
<220> FEATURE:
<223> OTHER INFORMATION: an artificially synthesized sequence

<400> SEQUENCE: 78
tcgagtaggc ttatcagact gatgttgag                                    29

<210> SEQ ID NO 79
<211> LENGTH: 22
<212> TYPE: DNA
<213> ORGANISM: Artificial
<220> FEATURE:
<223> OTHER INFORMATION: an artificially synthesized sequence

<400> SEQUENCE: 79
tcaacatcag tctgataagc ta                                           22

<210> SEQ ID NO 80
<211> LENGTH: 22
<212> TYPE: DNA
<213> ORGANISM: Artificial
<220> FEATURE:
<223> OTHER INFORMATION: an artificially synthesized sequence

<400> SEQUENCE: 80
cattaatgtc ggacaactca at                                           22

<210> SEQ ID NO 81
<211> LENGTH: 22
<212> TYPE: RNA
<213> ORGANISM: Artificial
<220> FEATURE:
<223> OTHER INFORMATION: an artificially synthesized sequence

<400> SEQUENCE: 81
uccgugguuc uacccugugg ua                                           22

<210> SEQ ID NO 82
<211> LENGTH: 22
<212> TYPE: RNA
<213> ORGANISM: Homo sapiens

<400> SEQUENCE: 82
uaccacaggg uagaaccacg ga                                           22

<210> SEQ ID NO 83
<211> LENGTH: 23
<212> TYPE: RNA
<213> ORGANISM: Artificial
<220> FEATURE:
<223> OTHER INFORMATION: an artificially synthesized sequence

<400> SEQUENCE: 83
uccgugguuc uaacccugug gua                                          23

<210> SEQ ID NO 84
<211> LENGTH: 24
<212> TYPE: RNA
<213> ORGANISM: Artificial
<220> FEATURE:
<223> OTHER INFORMATION: an artificially synthesized sequence

<400> SEQUENCE: 84
uccgugguuc uaaucccugu ggua                                         24

<210> SEQ ID NO 85
<211> LENGTH: 25
```

```
<212> TYPE: RNA
<213> ORGANISM: Artificial
<220> FEATURE:
<223> OTHER INFORMATION: an artificially synthesized sequence

<400> SEQUENCE: 85
uccgugguuc uaacucccug uggua                                             25

<210> SEQ ID NO 86
<211> LENGTH: 26
<212> TYPE: RNA
<213> ORGANISM: Artificial
<220> FEATURE:
<223> OTHER INFORMATION: an artificially synthesized sequence

<400> SEQUENCE: 86
uccgugguuc uaaucucccu guggua                                            26

<210> SEQ ID NO 87
<211> LENGTH: 122
<212> TYPE: RNA
<213> ORGANISM: Artificial
<220> FEATURE:
<223> OTHER INFORMATION: an artificially synthesized sequence
<220> FEATURE:
<221> NAME/KEY: misc_feature
<222> LOCATION: (22)..(47)
<223> OTHER INFORMATION: n is any one of a, g, c, or u
<220> FEATURE:
<221> NAME/KEY: misc_feature
<222> LOCATION: (74)..(99)
<223> OTHER INFORMATION: n is any one of a, g, c, or u

<400> SEQUENCE: 87
gacggcgcua ggaucaucaa cnnnnnnnnn nnnnnnnnnn nnnnnnncaa guauucuggu        60
cacagaauac aacnnnnnnn nnnnnnnnnn nnnnnnnnnc aagaugaucc uagcgccguc       120
uu                                                                     122

<210> SEQ ID NO 88
<211> LENGTH: 69
<212> TYPE: DNA
<213> ORGANISM: Artificial
<220> FEATURE:
<223> OTHER INFORMATION: an artificially synthesized sequence

<400> SEQUENCE: 88
agccttgttt gacggcgcta ggatcatcgg agacggtacc gtctcgatga tcctagcgcc       60
gtcttttttt                                                              69

<210> SEQ ID NO 89
<211> LENGTH: 69
<212> TYPE: DNA
<213> ORGANISM: Artificial
<220> FEATURE:
<223> OTHER INFORMATION: an artificially synthesized sequence

<400> SEQUENCE: 89
aaaaaagacg gcgctaggat catcgagacg gtaccgtctc cgatgatcct agcgccgtca       60
aacaaggct                                                               69

<210> SEQ ID NO 90
<211> LENGTH: 24
<212> TYPE: DNA
<213> ORGANISM: Artificial
<220> FEATURE:
<223> OTHER INFORMATION: an artificially synthesized sequence
```

<400> SEQUENCE: 90
agccttgttt gacggcgcta ggat                                              24

<210> SEQ ID NO 91
<211> LENGTH: 28
<212> TYPE: DNA
<213> ORGANISM: Artificial
<220> FEATURE:
<223> OTHER INFORMATION: an artificially synthesized sequence

<400> SEQUENCE: 91
gatgatccta gcgccgtcaa acaaggct                                          28

<210> SEQ ID NO 92
<211> LENGTH: 23
<212> TYPE: DNA
<213> ORGANISM: Artificial
<220> FEATURE:
<223> OTHER INFORMATION: an artificially synthesized sequence

<400> SEQUENCE: 92
atgatcctag cgccgtcttt ttt                                               23

<210> SEQ ID NO 93
<211> LENGTH: 19
<212> TYPE: DNA
<213> ORGANISM: Artificial
<220> FEATURE:
<223> OTHER INFORMATION: an artificially synthesized sequence

<400> SEQUENCE: 93
aaaaaagacg gcgctagga                                                    19

<210> SEQ ID NO 94
<211> LENGTH: 30
<212> TYPE: DNA
<213> ORGANISM: Artificial
<220> FEATURE:
<223> OTHER INFORMATION: an artificially synthesized sequence
<220> FEATURE:
<221> NAME/KEY: misc_feature
<222> LOCATION: (1)..(2)
<223> OTHER INFORMATION: n is any one of a, g, c, or t
<220> FEATURE:
<221> NAME/KEY: misc_feature
<222> LOCATION: (29)..(30)
<223> OTHER INFORMATION: n is any one of a, g, c, or t

<400> SEQUENCE: 94
nncaagtatt ctggtcacag aatacaacnn                                        30

<210> SEQ ID NO 95
<211> LENGTH: 10
<212> TYPE: DNA
<213> ORGANISM: Artificial
<220> FEATURE:
<223> OTHER INFORMATION: an artificially synthesized sequence
<220> FEATURE:
<221> NAME/KEY: misc_feature
<222> LOCATION: (9)..(10)
<223> OTHER INFORMATION: n is any one of a, g, c, or t

<400> SEQUENCE: 95 tcatcttgnn                                                              10

<210> SEQ ID NO 96
<211> LENGTH: 30

-continued

```
<212> TYPE: DNA
<213> ORGANISM: Artificial
<220> FEATURE:
<223> OTHER INFORMATION: an artificially synthesized sequence
<220> FEATURE:
<221> NAME/KEY: misc_feature
<222> LOCATION: (1)..(2)
<220> FEATURE:
<221> NAME/KEY: misc_feature
<222> LOCATION: (1)..(2)
<223> OTHER INFORMATION: n is any one of a, g, c, or t
<220> FEATURE:
<221> NAME/KEY: misc_feature
<222> LOCATION: (29)..(30)
<220> FEATURE:
<221> NAME/KEY: misc_feature
<222> LOCATION: (29)..(30)
<223> OTHER INFORMATION: n is any one of a, g, c, or t

<400> SEQUENCE: 96
nngttgtatt ctgtgaccag aatacttgnn                                  30

<210> SEQ ID NO 97
<211> LENGTH: 33
<212> TYPE: DNA
<213> ORGANISM: Artificial
<220> FEATURE:
<223> OTHER INFORMATION: an artificially synthesized sequence
<220> FEATURE:
<221> NAME/KEY: misc_feature
<222> LOCATION: (32)..(33)
<223> OTHER INFORMATION: n is any one of a, g, c, or t

<400> SEQUENCE: 97
agccttgttt gacggcgcta ggatcatcaa cnn                              33

<210> SEQ ID NO 98
<211> LENGTH: 29
<212> TYPE: DNA
<213> ORGANISM: Artificial
<220> FEATURE:
<223> OTHER INFORMATION: an artificially synthesized sequence
<220> FEATURE:
<221> NAME/KEY: misc_feature
<222> LOCATION: (1)..(2)
<223> OTHER INFORMATION: n is any one of a, g, c, or t

<400> SEQUENCE: 98
nncaagatga tcctagcgcc gtcttttt                                    29

<210> SEQ ID NO 99
<211> LENGTH: 29
<212> TYPE: DNA
<213> ORGANISM: Artificial
<220> FEATURE:
<223> OTHER INFORMATION: an artificially synthesized sequence
<220> FEATURE:
<221> NAME/KEY: misc_feature
<222> LOCATION: (28)..(29)
<223> OTHER INFORMATION: n is any one of a, g, c, or t

<400> SEQUENCE: 99
aaaaaagacg gcgctaggat catcttgnn                                   29

<210> SEQ ID NO 100
<211> LENGTH: 33
<212> TYPE: DNA
<213> ORGANISM: Artificial
<220> FEATURE:
<223> OTHER INFORMATION: an artificially synthesized sequence
<220> FEATURE:
<221> NAME/KEY: misc_feature
```

```
<222> LOCATION: (1)..(2)
<223> OTHER INFORMATION: n is any one of a, g, c, or t

<400> SEQUENCE: 100
nngttgatga tcctagcgcc gtcaaacaag gct                                    33

<210> SEQ ID NO 101
<211> LENGTH: 64
<212> TYPE: RNA
<213> ORGANISM: Artificial
<220> FEATURE:
<223> OTHER INFORMATION: an artificially synthesized sequence

<400> SEQUENCE: 101
gacggcgcug gaugcuugga uccgugguuc uacccugugg uaaggaagca uccagcgccg        60
ucuu                                                                    64

<210> SEQ ID NO 102
<211> LENGTH: 66
<212> TYPE: RNA
<213> ORGANISM: Artificial
<220> FEATURE:
<223> OTHER INFORMATION: an artificially synthesized sequence

<400> SEQUENCE: 102
gacggcgcua ggaugcuugg auccgugguu cuacccugug guaaggaagc auccagcgc        60 cgucuu                                                                  66

<210> SEQ ID NO 103
<211> LENGTH: 68
<212> TYPE: RNA
<213> ORGANISM: Artificial
<220> FEATURE:
<223> OTHER INFORMATION: an artificially synthesized sequence

<400> SEQUENCE: 103
gacagcgcuc uacgaugaag gcuccguggu ucuacccugu gguaagguuc aucguagagc        60
gcugucuu                                                                68

<210> SEQ ID NO 104
<211> LENGTH: 70
<212> TYPE: RNA
<213> ORGANISM: Artificial
<220> FEATURE:
<223> OTHER INFORMATION: an artificially synthesized sequence

<400> SEQUENCE: 104
gacagcgcuc uacgaugcaa ggcuccgugg uucuacccug ugguaagguu gcaucguaga        60
gcgcugucuu                                                              70

<210> SEQ ID NO 105
<211> LENGTH: 72
<212> TYPE: RNA
<213> ORGANISM: Artificial
<220> FEATURE:
<223> OTHER INFORMATION: an artificially synthesized sequence

<400> SEQUENCE: 105
gacagcgcuc gcaggaugcu uggcuccgug guucuacccu gugguaagga agcauccugc        60
gagcgcuguc uu                                                           72

<210> SEQ ID NO 106
<211> LENGTH: 78
```

```
<212> TYPE: RNA
<213> ORGANISM: Artificial
<220> FEATURE:
<223> OTHER INFORMATION: an artificially synthesized sequence

<400> SEQUENCE: 106
gacagcgcuc aaagcaggau gcuuggcucc gugguucuac ccugugguaa ggaagcaucc    60
ugcuuugagc gcugucuu                                                 78

<210> SEQ ID NO 107
<211> LENGTH: 80
<212> TYPE: RNA
<213> ORGANISM: Artificial
<220> FEATURE:
<223> OTHER INFORMATION: an artificially synthesized sequence

<400> SEQUENCE: 107
gacggcgcua ggaucaucuc cgugguucua cccuggggua guauucuggu cacagaauac    60
gaugauccua gcgccgucuu                                               80

<210> SEQ ID NO 108
<211> LENGTH: 100
<212> TYPE: RNA
<213> ORGANISM: Artificial
<220> FEATURE:
<223> OTHER INFORMATION: an artificially synthesized sequence

<400> SEQUENCE: 108
gacggcgcua ggaucaucgu auucggguca cagaauacuc cgugguucua cccuggggua    60
ucuucucuaa cgagagaaga gaugauccua gcgccgucuu                         100

<210> SEQ ID NO 109
<211> LENGTH: 102
<212> TYPE: RNA
<213> ORGANISM: Artificial
<220> FEATURE:
<223> OTHER INFORMATION: an artificially synthesized sequence

<400> SEQUENCE: 109
gacggcgcua ggaucaucuc cgugguucua cccuggggua guauucuggu cacagaauac    60
uccgugguuc uacccugugg uagaugaucc uagcgccguc uu                      102

<210> SEQ ID NO 110
<211> LENGTH: 114
<212> TYPE: RNA
<213> ORGANISM: Artificial
<220> FEATURE:
<223> OTHER INFORMATION: an artificially synthesized sequence

<400> SEQUENCE: 110
gacggcgcua ggaucaucaa cuccgugguu cuacccugug guacaaguau ucggucaca     60 gaauacaacu ccgugguucu acccuguggu acaagaugau ccuagcgccg ucuu         114

<210> SEQ ID NO 111
<211> LENGTH: 126
<212> TYPE: RNA
<213> ORGANISM: Artificial
<220> FEATURE:
<223> OTHER INFORMATION: an artificially synthesized sequence

<400> SEQUENCE: 111
gacggcgcua ggaucaucuc cgugguucua cccuggggua guauucugag auggugucuu    60
cuaccggugc cuaagacaga auacuccgug guucuacccu guguagaug auccuagcgc    120
```

```
cgucuu                                                           126

<210> SEQ ID NO 112
<211> LENGTH: 162
<212> TYPE: RNA
<213> ORGANISM: Artificial
<220> FEATURE:
<223> OTHER INFORMATION: an artificially synthesized sequence

<400> SEQUENCE: 112
gacggcgcua ggaucaucuc cgugguucua cccugugggua guauucuguc cgugguucua    60 cccugugggua guauucuggu cacagaauac uccgugguuc uacccugugg uacagaauac   120
uccgugguuc uacccugugg uagaugaucc uagcgccguc uu                      162

<210> SEQ ID NO 113
<211> LENGTH: 186
<212> TYPE: RNA
<213> ORGANISM: Artificial
<220> FEATURE:
<223> OTHER INFORMATION: an artificially synthesized sequence

<400> SEQUENCE: 113
gacggcgcua ggaucaucuc cgugguucua cccugugggua guauucuguc cgugguucua    60 cccugugggua guauucugag augguggucuu cuaccggugc cuaagacaga auacccgug   120 guucacccu gugguacaga auacccgug guucacccu gugguagaug auccuagcgc      180
cgucuu                                                              186

<210> SEQ ID NO 114
<211> LENGTH: 67
<212> TYPE: RNA
<213> ORGANISM: Artificial
<220> FEATURE:
<223> OTHER INFORMATION: an artificially synthesized sequence

<400> SEQUENCE: 114
gacggcgcua ggaugcuugg auccgugguu cuaacccugu gguaaggaag cauccuagcg    60
ccgucuu                                                              67

<210> SEQ ID NO 115
<211> LENGTH: 68
<212> TYPE: RNA
<213> ORGANISM: Artificial
<220> FEATURE:
<223> OTHER INFORMATION: an artificially synthesized sequence

<400> SEQUENCE: 115
gacggcgcua ggaugcuugg auccgugguu cuaaucccug ugguaaggaa gcauccuagc    60
gccgucuu                                                             68

<210> SEQ ID NO 116
<211> LENGTH: 69
<212> TYPE: RNA
<213> ORGANISM: Artificial
<220> FEATURE:
<223> OTHER INFORMATION: an artificially synthesized sequence

<400> SEQUENCE: 116
gacggcgcua ggaugcuugg auccgugguu cuaacucccu gugguaagga agcauccuag    60
cgccgucuu                                                            69
```

```
<210> SEQ ID NO 117
<211> LENGTH: 70
<212> TYPE: RNA
<213> ORGANISM: Artificial
<220> FEATURE:
<223> OTHER INFORMATION: an artificially synthesized sequence

<400> SEQUENCE: 117
gacggcgcua ggaugcuugg auccgugguu cuaaucuccc ugugguaagg aagcauccua      60
gcgccgucuu                                                             70

<210> SEQ ID NO 118
<211> LENGTH: 114
<212> TYPE: RNA
<213> ORGANISM: Artificial
<220> FEATURE:
<223> OTHER INFORMATION: an artificially synthesized sequence

<400> SEQUENCE: 118
gacggcgcua ggaucauccu ccgugguucu aaucucccug gguacguau ucggucaca        60 gaauaccucc gugguucuaa ucucccugug guacgaugau ccuagcgccg ucuu           114

<210> SEQ ID NO 119
<211> LENGTH: 118
<212> TYPE: RNA
<213> ORGANISM: Artificial
<220> FEATURE:
<223> OTHER INFORMATION: an artificially synthesized sequence

<400> SEQUENCE: 119
gacggcgcua ggaucauccc uccgugguuc uaaucucccu gguguaccgu auucggguca      60
cagaauaccc uccgugguuc uaaucucccu gugguaccga ugauccuagc gccgucuu      118

<210> SEQ ID NO 120
<211> LENGTH: 122
<212> TYPE: RNA
<213> ORGANISM: Artificial
<220> FEATURE:
<223> OTHER INFORMATION: an artificially synthesized sequence

<400> SEQUENCE: 120
gacggcgcua ggaucaucaa cuccgugguu cuaaucuccc ugugguacaa guauucuggu      60
cacagaauac aacuccgugg uucuaaucuc ccugugguac aagaugaucc uagcgccguc    120
uu                                                                  122

<210> SEQ ID NO 121
<211> LENGTH: 126
<212> TYPE: RNA
<213> ORGANISM: Artificial
<220> FEATURE:
<223> OTHER INFORMATION: an artificially synthesized sequence

<400> SEQUENCE: 121
gacggcgcua ggaucaucac ccuccgugguu ucuaaucucc cuguggguacc caguauucug    60 gucacagaau acaccuccg ugguucuaau cucccugugg uacccagaug auccuagcgc     120
cgucuu                                                              126

<210> SEQ ID NO 122
<211> LENGTH: 130
<212> TYPE: RNA
<213> ORGANISM: Artificial
<220> FEATURE:
<223> OTHER INFORMATION: an artificially synthesized sequence
```

```
<400> SEQUENCE: 122
gacggcgcua ggaucaucaa cccuccgugg uucuaaucuc ccuguggua ccaaguauuc      60 uggucacaga auacaacccu ccgugguucu aaucucccug gguacccaa gaugauccua     120 gcgccgucuu                                                          130

<210> SEQ ID NO 123
<211> LENGTH: 230
<212> TYPE: RNA
<213> ORGANISM: Artificial
<220> FEATURE:
<223> OTHER INFORMATION: an artificially synthesized sequence

<400> SEQUENCE: 123
gacggcgcua ggaucaucaa cuccgugguu cuaaucuccc uggguacaa gcgacaagaa      60 cuccguggu cuaaucuccc uggguacaa guauucugaa cuggugucuu cuaaucuccg     120
gugccuacaa cagaauacaa cuccguggu cuaaucuccc uggguacaa cuugucgcaa     180 cuccguggu cuaaucuccc uggguacaa gaugauccua gcgccgucuu                230

<210> SEQ ID NO 124
<211> LENGTH: 26
<212> TYPE: RNA
<213> ORGANISM: Artificial
<220> FEATURE:
<223> OTHER INFORMATION: an artificially synthesized sequence

<400> SEQUENCE: 124
cuaccauagg gucaucaaaa ccacug                                         26

<210> SEQ ID NO 125
<211> LENGTH: 22
<212> TYPE: RNA
<213> ORGANISM: Homo sapiens

<400> SEQUENCE: 125
cagugguuuu acccuauggu ag                                             22

<210> SEQ ID NO 126
<211> LENGTH: 26
<212> TYPE: RNA
<213> ORGANISM: Artificial
<220> FEATURE:
<223> OTHER INFORMATION: an artificially synthesized sequence

<400> SEQUENCE: 126
ucaacaucag ucaaugugau aagcua                                         26

<210> SEQ ID NO 127
<211> LENGTH: 22
<212> TYPE: RNA
<213> ORGANISM: Homo sapiens

<400> SEQUENCE: 127
uagcuuauca gacugauguu ga                                             22

<210> SEQ ID NO 128
<211> LENGTH: 22
<212> TYPE: RNA
<213> ORGANISM: Artificial
<220> FEATURE:
<223> OTHER INFORMATION: an artificially synthesized sequence

<400> SEQUENCE: 128
```

```
ucaacaucag ucugauaagc ua                                            22

<210> SEQ ID NO 129
<211> LENGTH: 122
<212> TYPE: RNA
<213> ORGANISM: Artificial
<220> FEATURE:
<223> OTHER INFORMATION: an artificially synthesized sequence

<400> SEQUENCE: 129
gacggcgcua ggaucaucaa ccuaccauag ggucaucaaa accacugcaa guauucuggu    60
cacagaauac aaccuaccau agggucauca aaaccacugc aagaugaucc uagcgccguc   120
uu                                                                 122

<210> SEQ ID NO 130
<211> LENGTH: 122
<212> TYPE: RNA
<213> ORGANISM: Artificial
<220> FEATURE:
<223> OTHER INFORMATION: an artificially synthesized sequence

<400> SEQUENCE: 130
gacggcgcua ggaucaucaa cucaacauca gucaauguga uaagcuacaa guauucuggu    60
cacagaauac aacucaacau cagucaaugu gauaagcuac aagaugaucc uagcgccguc   120
uu                                                                 122

<210> SEQ ID NO 131
<211> LENGTH: 114
<212> TYPE: RNA
<213> ORGANISM: Artificial
<220> FEATURE:
<223> OTHER INFORMATION: an artificially synthesized sequence

<400> SEQUENCE: 131
gacggcgcua ggaucaucaa cucaacauca gucugauaag cuacaaguau ucggucaca    60 gaauacaacu caacaucagu cugauaagcu acaagaugau ccuagcgccg ucuu         114

<210> SEQ ID NO 132
<211> LENGTH: 120
<212> TYPE: RNA
<213> ORGANISM: Artificial
<220> FEATURE:
<223> OTHER INFORMATION: an artificially synthesized sequence

<400> SEQUENCE: 132
gacggcgcua ggaucaucaa caagccacaa cgaaucucua uaucaucaag uauucgguc     60 acagaauaca acaagccaca acgaaucucu auaucaucaa gaugauccua gcgccgucuu   120

<210> SEQ ID NO 133
<211> LENGTH: 28
<212> TYPE: DNA
<213> ORGANISM: Artificial
<220> FEATURE:
<223> OTHER INFORMATION: an artificially synthesized sequence

<400> SEQUENCE: 133
cgggatccat ccgacgccgc catctcta                                      28

<210> SEQ ID NO 134
<211> LENGTH: 76
<212> TYPE: DNA
<213> ORGANISM: Artificial
```

```
<220> FEATURE:
<223> OTHER INFORMATION: an artificially synthesized sequence

<400> SEQUENCE: 134
ggaattcaaa aaatagctta tcagactgat gttgatagct tatcagactg atgttgaaaa    60
caaggctttt ctccaa                                                    76

<210> SEQ ID NO 135
<211> LENGTH: 21
<212> TYPE: DNA
<213> ORGANISM: Artificial
<220> FEATURE:
<223> OTHER INFORMATION: an artificially synthesized sequence

<400> SEQUENCE: 135
gttgatgatc ctagcgccgt c                                              21

<210> SEQ ID NO 136
<211> LENGTH: 22
<212> TYPE: DNA
<213> ORGANISM: Artificial
<220> FEATURE:
<223> OTHER INFORMATION: an artificially synthesized sequence

<400> SEQUENCE: 136
tcaacatcag tctgataagc ta                                             22

<210> SEQ ID NO 137
<211> LENGTH: 23
<212> TYPE: DNA
<213> ORGANISM: Artificial
<220> FEATURE:
<223> OTHER INFORMATION: an artificially synthesized sequence

<400> SEQUENCE: 137
gcagtggggg gttgtatacc aac                                            23

<210> SEQ ID NO 138
<211> LENGTH: 23
<212> TYPE: DNA
<213> ORGANISM: Artificial
<220> FEATURE:
<223> OTHER INFORMATION: an artificially synthesized sequence

<400> SEQUENCE: 138
gtgatggaag cataacctgt ctc                                            23

<210> SEQ ID NO 139
<211> LENGTH: 21
<212> TYPE: RNA
<213> ORGANISM: Artificial
<220> FEATURE:
<223> OTHER INFORMATION: an artificially synthesized sequence

<400> SEQUENCE: 139
uagcagcaca gaaauauugg c                                              21

<210> SEQ ID NO 140
<211> LENGTH: 22
<212> TYPE: RNA
<213> ORGANISM: Homo sapiens

<400> SEQUENCE: 140
uagcagcacg uaaauauugg cg                                             22
```

```
<210> SEQ ID NO 141
<211> LENGTH: 21
<212> TYPE: RNA
<213> ORGANISM: Artificial
<220> FEATURE:
<223> OTHER INFORMATION: an artificially synthesized sequence

<400> SEQUENCE: 141
cagcagcaca cugugguuug u                                              21

<210> SEQ ID NO 142
<211> LENGTH: 26
<212> TYPE: RNA
<213> ORGANISM: Artificial
<220> FEATURE:
<223> OTHER INFORMATION: an artificially synthesized sequence

<400> SEQUENCE: 142
cgccaauauu uagauccgug cugcua                                         26

<210> SEQ ID NO 143
<211> LENGTH: 25
<212> TYPE: RNA
<213> ORGANISM: Artificial
<220> FEATURE:
<223> OTHER INFORMATION: an artificially synthesized sequence

<400> SEQUENCE: 143
gccaauauuu caaugugugc ugcua                                          25

<210> SEQ ID NO 144
<211> LENGTH: 25
<212> TYPE: RNA
<213> ORGANISM: Artificial
<220> FEATURE:
<223> OTHER INFORMATION: an artificially synthesized sequence

<400> SEQUENCE: 144
acaaaccaca gaaucugugc ugcug                                          25

<210> SEQ ID NO 145
<211> LENGTH: 122
<212> TYPE: RNA
<213> ORGANISM: Artificial
<220> FEATURE:
<223> OTHER INFORMATION: an artificially synthesized sequence

<400> SEQUENCE: 145
gacggcgcua ggaucaucaa ccgccaauau uuagauccgu gcugcuacaa guauucuggu    60
cacagaauac aaccgccaau auuuagaucc gugcugcuac aagaugaucc uagcgccguc    120
uu                                                                   122

<210> SEQ ID NO 146
<211> LENGTH: 119
<212> TYPE: RNA
<213> ORGANISM: Artificial
<220> FEATURE:
<223> OTHER INFORMATION: an artificially synthesized sequence

<400> SEQUENCE: 146
gacggcgcua ggaucaucaa cgccaauauu ucaaugggc ugcuacaagu auucuggca      60 cagaauacaa cgccaauauu ucaaugugug cugcuacaag augauccuag cgccgucuu    119

<210> SEQ ID NO 147
<211> LENGTH: 120
```

```
<212> TYPE: RNA
<213> ORGANISM: Artificial
<220> FEATURE:
<223> OTHER INFORMATION: an artificially synthesized sequence

<400> SEQUENCE: 147
gacggcgcua ggaucaucaa cacaaaccac agaaucugug cugcugcaag uauucgguc      60 acagaauaca acacaaacca cagaaucugu gcugcugcaa gaugauccua gcgccgucuu   120

<210> SEQ ID NO 148
<211> LENGTH: 60
<212> TYPE: RNA
<213> ORGANISM: Artificial
<220> FEATURE:
<223> OTHER INFORMATION: an artificially synthesized sequence

<400> SEQUENCE: 148
gacggcgcua ggaucaucaa cucaacauca gucaauguga uaagcuacaa guauucggu      60

<210> SEQ ID NO 149
<211> LENGTH: 60
<212> TYPE: RNA
<213> ORGANISM: Artificial
<220> FEATURE:
<223> OTHER INFORMATION: an artificially synthesized sequence

<400> SEQUENCE: 149
accagaauac aacucaacau cagucaaugu gauaagcuac aagaugaucc uagcgccguc      60

<210> SEQ ID NO 150
<211> LENGTH: 23
<212> TYPE: RNA
<213> ORGANISM: Artificial
<220> FEATURE:
<223> OTHER INFORMATION: an artificially synthesized sequence

<400> SEQUENCE: 150
gucaacauca gucugauaag cua                                             23

<210> SEQ ID NO 151
<211> LENGTH: 21
<212> TYPE: RNA
<213> ORGANISM: Artificial
<220> FEATURE:
<223> OTHER INFORMATION: an artificially synthesized sequence

<400> SEQUENCE: 151
aaggcaagcu gacccugaag u                                               21

<210> SEQ ID NO 152
<211> LENGTH: 9
<212> TYPE: PRT
<213> ORGANISM: Artificial
<220> FEATURE:
<223> OTHER INFORMATION: an artificially synthesized sequence

<400> SEQUENCE: 152

Arg Arg Arg Gln Arg Arg Lys Lys Arg
1               5

<210> SEQ ID NO 153
<211> LENGTH: 15
<212> TYPE: DNA
<213> ORGANISM: Artificial
<220> FEATURE:
<223> OTHER INFORMATION: an artificially synthesized sequence
```

-continued

<400> SEQUENCE: 153
attaatgtcg gacaa         15

<210> SEQ ID NO 154
<211> LENGTH: 15
<212> TYPE: DNA
<213> ORGANISM: Artificial
<220> FEATURE:
<223> OTHER INFORMATION: an artificially synthesized sequence

<400> SEQUENCE: 154
tcaacatcag tctga         15

<210> SEQ ID NO 155
<211> LENGTH: 27
<212> TYPE: DNA
<213> ORGANISM: Artificial
<220> FEATURE:
<223> OTHER INFORMATION: an artificially synthesized sequence

<400> SEQUENCE: 155
ggatcctgca gtatttagca tgcccca         27

<210> SEQ ID NO 156
<211> LENGTH: 89
<212> TYPE: DNA
<213> ORGANISM: Artificial
<220> FEATURE:
<223> OTHER INFORMATION: an artificially synthesized sequence

<400> SEQUENCE: 156
gaattcaaaa aaggatgtga gggcgtcatc gagacggtac cgtctccgat gacgccctca         60
catccgaggt acccaggcgg cgcacaagc         89

<210> SEQ ID NO 157
<211> LENGTH: 82
<212> TYPE: DNA
<213> ORGANISM: Artificial
<220> FEATURE:
<223> OTHER INFORMATION: an artificially synthesized sequence

<400> SEQUENCE: 157
ctcggatgtg agggcgtcat cggagacgac accatccaca gccagcgtct cgatgacgcc         60
ctcacatcct tttttgaatt ca         82

<210> SEQ ID NO 158
<211> LENGTH: 90
<212> TYPE: DNA
<213> ORGANISM: Artificial
<220> FEATURE:
<223> OTHER INFORMATION: an artificially synthesized sequence

<400> SEQUENCE: 158
agcttgaatt caaaaaagga tgtgagggcg tcatcgagac gctggctgtg gatggtgtcg         60
tctccgatga cgccctcaca tccgaggtac         90

<210> SEQ ID NO 159
<211> LENGTH: 84
<212> TYPE: DNA
<213> ORGANISM: Artificial
<220> FEATURE:
<223> OTHER INFORMATION: an artificially synthesized sequence

<400> SEQUENCE: 159

| catcaactca acatcagtca atgtgataag ctacaaggga gggcgggagg gaactcaaca | 60 |
| tcagtcaatg tgataagcta caag | 84 |

<210> SEQ ID NO 160
<211> LENGTH: 84
<212> TYPE: DNA
<213> ORGANISM: Artificial
<220> FEATURE:
<223> OTHER INFORMATION: an artificially synthesized sequence

<400> SEQUENCE: 160

| tcatcttgta gcttatcaca ttgactgatg ttgagttccc tcccgccctc ccttgtagct | 60 |
| tatcacattg actgatgttg agtt | 84 |

<210> SEQ ID NO 161
<211> LENGTH: 90
<212> TYPE: DNA
<213> ORGANISM: Artificial
<220> FEATURE:
<223> OTHER INFORMATION: an artificially synthesized sequence

<400> SEQUENCE: 161

| catcaactca acatcagtca atgtgataag ctacaaggga gaggggcggg gcgcgggaac | 60 |
| tcaacatcag tcaatgtgat aagctacaag | 90 |

<210> SEQ ID NO 162
<211> LENGTH: 90
<212> TYPE: DNA
<213> ORGANISM: Artificial
<220> FEATURE:
<223> OTHER INFORMATION: an artificially synthesized sequence

<400> SEQUENCE: 162

| tcatcttgta gcttatcaca ttgactgatg ttgagttccc gcgccccgcc cctctccctt | 60 |
| gtagcttatc acattgactg atgttgagtt | 90 |

<210> SEQ ID NO 163
<211> LENGTH: 89
<212> TYPE: DNA
<213> ORGANISM: Artificial
<220> FEATURE:
<223> OTHER INFORMATION: an artificially synthesized sequence

<400> SEQUENCE: 163

| catcaactca acatcagtca atgtgataag ctacaagtat tctggtcaca gaatacaaca | 60 |
| tcgaatagtg taactgacta caactcaag | 89 |

<210> SEQ ID NO 164
<211> LENGTH: 89
<212> TYPE: DNA
<213> ORGANISM: Artificial
<220> FEATURE:
<223> OTHER INFORMATION: an artificially synthesized sequence

<400> SEQUENCE: 164

| tcatcttgag ttgtagtcag ttacactatt cgatgttgta ttctgtgacc agaatacttg | 60 |
| tagcttatca cattgactga tgttgagtt | 89 |

<210> SEQ ID NO 165
<211> LENGTH: 88
<212> TYPE: DNA
<213> ORGANISM: Artificial
<220> FEATURE:

<223> OTHER INFORMATION: an artificially synthesized sequence

<400> SEQUENCE: 165
catcaactca acatcagtca atgtgataag ctacaagtat tctggtcaca gaatacaaca    60
agccacaacg aatctctata tcatcaag                                       88

<210> SEQ ID NO 166
<211> LENGTH: 88
<212> TYPE: DNA
<213> ORGANISM: Artificial
<220> FEATURE:
<223> OTHER INFORMATION: an artificially synthesized sequence

<400> SEQUENCE: 166
tcatcttgat gatatagaga ttcgttgtgg cttgttgtat tctgtgacca gaatacttgt    60
agcttatcac attgactgat gttgagtt                                       88

<210> SEQ ID NO 167
<211> LENGTH: 15
<212> TYPE: DNA
<213> ORGANISM: Artificial
<220> FEATURE:
<223> OTHER INFORMATION: an artificially synthesized sequence

<400> SEQUENCE: 167
gggagggcgg gaggg                                                     15

<210> SEQ ID NO 168
<211> LENGTH: 21
<212> TYPE: DNA
<213> ORGANISM: Artificial
<220> FEATURE:
<223> OTHER INFORMATION: an artificially synthesized sequence

<400> SEQUENCE: 168 gggagaggggg cggggcgcgg g                                             21

<210> SEQ ID NO 169
<211> LENGTH: 82
<212> TYPE: DNA
<213> ORGANISM: Artificial
<220> FEATURE:
<223> OTHER INFORMATION: an artificially synthesized sequence

<400> SEQUENCE: 169
tgggtacctc ggatgtgagg gcgtcatcgg agacgacacc atccacagcc agcgtctcga    60
tgacgccctc acatcctttt tt                                             82

<210> SEQ ID NO 170
<211> LENGTH: 82
<212> TYPE: DNA
<213> ORGANISM: Artificial
<220> FEATURE:
<223> OTHER INFORMATION: an artificially synthesized sequence

<400> SEQUENCE: 170
aaaaaaggat gtgagggcgt catcgagacg ctggctgtgg atggtgtcgt ctccgatgac    60
gccctcacat ccgaggtacc ca                                             82

<210> SEQ ID NO 171
<211> LENGTH: 24
<212> TYPE: DNA
<213> ORGANISM: Artificial
<220> FEATURE:

<223> OTHER INFORMATION: an artificially synthesized sequence

<400> SEQUENCE: 171
tgggtacctc ggatgtgagg gcgt                                              24

<210> SEQ ID NO 172
<211> LENGTH: 28
<212> TYPE: DNA
<213> ORGANISM: Artificial
<220> FEATURE:
<223> OTHER INFORMATION: an artificially synthesized sequence

<400> SEQUENCE: 172
gatgacgccc tcacatccga ggtaccca                                          28

<210> SEQ ID NO 173
<211> LENGTH: 23
<212> TYPE: DNA
<213> ORGANISM: Artificial
<220> FEATURE:
<223> OTHER INFORMATION: an artificially synthesized sequence

<400> SEQUENCE: 173
atgacgccct cacatccttt ttt                                               23

<210> SEQ ID NO 174
<211> LENGTH: 19
<212> TYPE: DNA
<213> ORGANISM: Artificial
<220> FEATURE:
<223> OTHER INFORMATION: an artificially synthesized sequence

<400> SEQUENCE: 174
aaaaaaggat gtgagggcg                                                    19

<210> SEQ ID NO 175
<211> LENGTH: 33
<212> TYPE: DNA
<213> ORGANISM: Artificial
<220> FEATURE:
<223> OTHER INFORMATION: an artificially synthesized sequence
<220> FEATURE:
<221> NAME/KEY: misc_feature
<222> LOCATION: (32)..(33)
<223> OTHER INFORMATION: n is any one of a, g, c, or t

<400> SEQUENCE: 175
tgggtacctc ggatgtgagg gcgtcatcaa cnn                                    33

<210> SEQ ID NO 176
<211> LENGTH: 33
<212> TYPE: DNA
<213> ORGANISM: Artificial
<220> FEATURE:
<223> OTHER INFORMATION: an artificially synthesized sequence
<220> FEATURE:
<221> NAME/KEY: misc_feature
<222> LOCATION: (1)..(2)
<223> OTHER INFORMATION: n is any one of a, g, c, or t

<400> SEQUENCE: 176
nngttgatga cgccctcaca tccgaggtac cca                                    33

<210> SEQ ID NO 177
<211> LENGTH: 29
<212> TYPE: DNA
<213> ORGANISM: Artificial
<220> FEATURE:

```
<223> OTHER INFORMATION: an artificially synthesized sequence
<220> FEATURE:
<221> NAME/KEY: misc_feature
<222> LOCATION: (1)..(2)
<223> OTHER INFORMATION: n is any one of a, g, c, or t

<400> SEQUENCE: 177
nncaagatga cgccctcaca tcctttttt                                       29

<210> SEQ ID NO 178
<211> LENGTH: 29
<212> TYPE: DNA
<213> ORGANISM: Artificial
<220> FEATURE:
<223> OTHER INFORMATION: an artificially synthesized sequence
<220> FEATURE:
<221> NAME/KEY: misc_feature
<222> LOCATION: (28)..(29)
<223> OTHER INFORMATION: n is any one of a, g, c, or t

<400> SEQUENCE: 178
aaaaaaggat gtgagggcgt catcttgnn                                       29

<210> SEQ ID NO 179
<211> LENGTH: 91
<212> TYPE: DNA
<213> ORGANISM: Artificial
<220> FEATURE:
<223> OTHER INFORMATION: an artificially synthesized sequence

<400> SEQUENCE: 179
catcaactcc atcattaccc cactggcagt attacaagta ttctggtcac agaatacaac     60
tccatcatta ccccactggc agtattacaa g                                    91

<210> SEQ ID NO 180
<211> LENGTH: 91
<212> TYPE: DNA
<213> ORGANISM: Artificial
<220> FEATURE:
<223> OTHER INFORMATION: an artificially synthesized sequence

<400> SEQUENCE: 180
tcatcttgta atactgccag tggggtaatg atggagttgt attctgtgac cagaatactt     60
gtaatactgc cagtggggta atgatggagt t                                    91

<210> SEQ ID NO 181
<211> LENGTH: 81
<212> TYPE: DNA
<213> ORGANISM: Artificial
<220> FEATURE:
<223> OTHER INFORMATION: an artificially synthesized sequence

<400> SEQUENCE: 181
catctccatc attacccccac tggcagtatt acgtattctg tcacagaat actccatcat     60 taccccactg gcagtattac g                                               81

<210> SEQ ID NO 182
<211> LENGTH: 81
<212> TYPE: DNA
<213> ORGANISM: Artificial
<220> FEATURE:
<223> OTHER INFORMATION: an artificially synthesized sequence

<400> SEQUENCE: 182
tcatcgtaat actgccagtg gggtaatgat ggagtattct gtgaccagaa tacgtaatac     60
```

```
tgccagtggg gtaatgatgg a                                               81
```

<210> SEQ ID NO 183
<211> LENGTH: 53
<212> TYPE: DNA
<213> ORGANISM: Artificial
<220> FEATURE:
<223> OTHER INFORMATION: an artificially synthesized sequence

<400> SEQUENCE: 183

```
ctagaccgga attctccatc attacccggc agtattactc gagcggaggc cgg           53
```

<210> SEQ ID NO 184
<211> LENGTH: 45
<212> TYPE: DNA
<213> ORGANISM: Artificial
<220> FEATURE:
<223> OTHER INFORMATION: an artificially synthesized sequence

<400> SEQUENCE: 184

```
cctccgctcg agtaatactg ccgggtaatg atggagaatt ccggt                    45
```

<210> SEQ ID NO 185
<211> LENGTH: 56
<212> TYPE: RNA
<213> ORGANISM: Artificial
<220> FEATURE:
<223> OTHER INFORMATION: an artificially synthesized sequence

<400> SEQUENCE: 185

```
gacggcgcua ggaucaucaa cucaacauca gucugauaag cuacaaguau ucuggu        56
```

<210> SEQ ID NO 186
<211> LENGTH: 56
<212> TYPE: RNA
<213> ORGANISM: Artificial
<220> FEATURE:
<223> OTHER INFORMATION: an artificially synthesized sequence

<400> SEQUENCE: 186

```
accagaauac aacucaacau cagucugaua agcuacaaga ugauccuagc gccguc        56
```

<210> SEQ ID NO 187
<211> LENGTH: 56
<212> TYPE: RNA
<213> ORGANISM: Artificial
<220> FEATURE:
<223> OTHER INFORMATION: an artificially synthesized sequence

<400> SEQUENCE: 187

```
gacggcgcua ggaucaucaa cucaacauca guccgauaag cuacaaguau ucuggu        56
```

<210> SEQ ID NO 188
<211> LENGTH: 56
<212> TYPE: RNA
<213> ORGANISM: Artificial
<220> FEATURE:
<223> OTHER INFORMATION: an artificially synthesized sequence

<400> SEQUENCE: 188

```
accagaauac aacucaacau caguccgaua agcuacaaga ugauccuagc gccguc        56
```

<210> SEQ ID NO 189
<211> LENGTH: 57
<212> TYPE: RNA
<213> ORGANISM: Artificial
<220> FEATURE:

<223> OTHER INFORMATION: an artificially synthesized sequence

<400> SEQUENCE: 189
gacggcgcua ggaucaucaa cuccaucauu acccggcagu auuacaagua uucuggu    57

<210> SEQ ID NO 190
<211> LENGTH: 57
<212> TYPE: RNA
<213> ORGANISM: Artificial
<220> FEATURE:
<223> OTHER INFORMATION: an artificially synthesized sequence

<400> SEQUENCE: 190
accagaauac aacuccauca uuacccggca guauuacaag augauccuag cgccguc    57

<210> SEQ ID NO 191
<211> LENGTH: 61
<212> TYPE: RNA
<213> ORGANISM: Artificial
<220> FEATURE:
<223> OTHER INFORMATION: an artificially synthesized sequence

<400> SEQUENCE: 191
gacggcgcua ggaucaucaa cuccaucauu accccacugg caguauuaca aguauucugg    60
u    61

<210> SEQ ID NO 192
<211> LENGTH: 61
<212> TYPE: RNA
<213> ORGANISM: Artificial
<220> FEATURE:
<223> OTHER INFORMATION: an artificially synthesized sequence

<400> SEQUENCE: 192
accagaauac aacuccauca uuaccccacu ggcaguauua caagaugauc cuagcgccgu    60
c    61

<210> SEQ ID NO 193
<211> LENGTH: 61
<212> TYPE: RNA
<213> ORGANISM: Artificial
<220> FEATURE:
<223> OTHER INFORMATION: an artificially synthesized sequence

<400> SEQUENCE: 193
gacggcgcua ggaucaucaa cuccaucauu acccauuagg caguauuaca aguauucugg    60
u    61

<210> SEQ ID NO 194
<211> LENGTH: 61
<212> TYPE: RNA
<213> ORGANISM: Artificial
<220> FEATURE:
<223> OTHER INFORMATION: an artificially synthesized sequence

<400> SEQUENCE: 194
accagaauac aacuccauca uuacccauua ggcaguauua caagaugauc cuagcgccgu    60
c    61

<210> SEQ ID NO 195
<211> LENGTH: 57
<212> TYPE: RNA
<213> ORGANISM: Artificial
<220> FEATURE:

<223> OTHER INFORMATION: an artificially synthesized sequence

<400> SEQUENCE: 195
gacggcgcua ggaucaucaa cuccaucauu acccagcagu auuacaagua uucuggu          57

<210> SEQ ID NO 196
<211> LENGTH: 57
<212> TYPE: RNA
<213> ORGANISM: Artificial
<220> FEATURE:
<223> OTHER INFORMATION: an artificially synthesized sequence

<400> SEQUENCE: 196
accagaauac aacuccauca uuacccagca guauuacaag augauccuag cgccguc          57

<210> SEQ ID NO 197
<211> LENGTH: 56
<212> TYPE: RNA
<213> ORGANISM: Artificial
<220> FEATURE:
<223> OTHER INFORMATION: an artificially synthesized sequence

<400> SEQUENCE: 197
gacggcgcua ggaucaucaa ccgccaauau uuacgugcug cuacaaguau ucuggu           56

<210> SEQ ID NO 198
<211> LENGTH: 56
<212> TYPE: RNA
<213> ORGANISM: Artificial
<220> FEATURE:
<223> OTHER INFORMATION: an artificially synthesized sequence

<400> SEQUENCE: 198
accagaauac aaccgccaau auuuacgugc ugcuacaaga ugauccuagc gccguc           56

<210> SEQ ID NO 199
<211> LENGTH: 60
<212> TYPE: RNA
<213> ORGANISM: Artificial
<220> FEATURE:
<223> OTHER INFORMATION: an artificially synthesized sequence

<400> SEQUENCE: 199
gacggcgcua ggaucaucaa ccgccaauau uuaguuccgu gcugcuacaa guauucuggu       60

<210> SEQ ID NO 200
<211> LENGTH: 60
<212> TYPE: RNA
<213> ORGANISM: Artificial
<220> FEATURE:
<223> OTHER INFORMATION: an artificially synthesized sequence

<400> SEQUENCE: 200
accagaauac aaccgccaau auuuaguucc gugcugcuac aagaugaucc uagcgccguc       60

<210> SEQ ID NO 201
<211> LENGTH: 56
<212> TYPE: RNA
<213> ORGANISM: Artificial
<220> FEATURE:
<223> OTHER INFORMATION: an artificially synthesized sequence

<400> SEQUENCE: 201
gacggcgcua ggaucaucaa ccgccaauau uuaugugcug cuacaaguau ucuggu           56

<210> SEQ ID NO 202

```
<211> LENGTH: 56
<212> TYPE: RNA
<213> ORGANISM: Artificial
<220> FEATURE:
<223> OTHER INFORMATION: an artificially synthesized sequence

<400> SEQUENCE: 202
accagaauac aaccgccaau auuuaugugc ugcuacaaga ugauccuagc gccguc      56

<210> SEQ ID NO 203
<211> LENGTH: 56
<212> TYPE: RNA
<213> ORGANISM: Artificial
<220> FEATURE:
<223> OTHER INFORMATION: an artificially synthesized sequence

<400> SEQUENCE: 203
gacggcgcua ggaucaucaa ccgccaauau uuaagugcug cuacaaguau ucuggu      56

<210> SEQ ID NO 204
<211> LENGTH: 56
<212> TYPE: RNA
<213> ORGANISM: Artificial
<220> FEATURE:
<223> OTHER INFORMATION: an artificially synthesized sequence

<400> SEQUENCE: 204
accagaauac aaccgccaau auuuaagugc ugcuacaaga ugauccuagc gccguc      56

<210> SEQ ID NO 205
<211> LENGTH: 23
<212> TYPE: RNA
<213> ORGANISM: Homo sapiens

<400> SEQUENCE: 205
uaauacugcc ggguaaugau gga                                          23

<210> SEQ ID NO 206
<211> LENGTH: 27
<212> TYPE: RNA
<213> ORGANISM: Artificial
<220> FEATURE:
<223> OTHER INFORMATION: an artificially synthesized sequence

<400> SEQUENCE: 206
uccaucauua ccccacuggc aguauua                                      27

<210> SEQ ID NO 207
<211> LENGTH: 23
<212> TYPE: RNA
<213> ORGANISM: Artificial
<220> FEATURE:
<223> OTHER INFORMATION: an artificially synthesized sequence

<400> SEQUENCE: 207
uccaucauua cccagcagua uua                                          23

<210> SEQ ID NO 208
<211> LENGTH: 22
<212> TYPE: RNA
<213> ORGANISM: Artificial
<220> FEATURE:
<223> OTHER INFORMATION: an artificially synthesized sequence

<400> SEQUENCE: 208
cgccaauauu uacgugcugc ua                                           22
```

```
<210> SEQ ID NO 209
<211> LENGTH: 59
<212> TYPE: RNA
<213> ORGANISM: Artificial
<220> FEATURE:
<223> OTHER INFORMATION: an artificially synthesized sequence

<400> SEQUENCE: 209
gacggcgcua ggaucaucaa cuaucgcgag uaucgacguc gaggcccaag uauucuggu      59

<210> SEQ ID NO 210
<211> LENGTH: 59
<212> TYPE: RNA
<213> ORGANISM: Artificial
<220> FEATURE:
<223> OTHER INFORMATION: an artificially synthesized sequence

<400> SEQUENCE: 210
accagaauac aacuaucgcg aguaucgacg ucgaggccca agaugauccu agcgccguc      59

<210> SEQ ID NO 211
<211> LENGTH: 52
<212> TYPE: DNA
<213> ORGANISM: Artificial
<220> FEATURE:
<223> OTHER INFORMATION: an artificially synthesized sequence

<400> SEQUENCE: 211
ctagaccgga attctcaaca tcagtctgat aagctactcg agcggaggcc gg             52

<210> SEQ ID NO 212
<211> LENGTH: 44
<212> TYPE: DNA
<213> ORGANISM: Artificial
<220> FEATURE:
<223> OTHER INFORMATION: an artificially synthesized sequence

<400> SEQUENCE: 212
cctccgctcg agtagcttat cagactgatg ttgagaattc cggt                      44

<210> SEQ ID NO 213
<211> LENGTH: 52
<212> TYPE: DNA
<213> ORGANISM: Artificial
<220> FEATURE:
<223> OTHER INFORMATION: an artificially synthesized sequence

<400> SEQUENCE: 213
ctagaccgga attccgccaa tatttacgtg ctgctactcg agcggaggcc gg             52

<210> SEQ ID NO 214
<211> LENGTH: 44
<212> TYPE: DNA
<213> ORGANISM: Artificial
<220> FEATURE:
<223> OTHER INFORMATION: an artificially synthesized sequence

<400> SEQUENCE: 214
cctccgctcg agtagcagca cgtaaatatt ggcggaattc cggt                      44

<210> SEQ ID NO 215
<211> LENGTH: 26
<212> TYPE: RNA
<213> ORGANISM: Artificial
<220> FEATURE:
<223> OTHER INFORMATION: an artificially synthesized sequence
```

```
<400> SEQUENCE: 215
cgccaauauu uaguuccgug cugcua                                    26

<210> SEQ ID NO 216
<211> LENGTH: 22
<212> TYPE: RNA
<213> ORGANISM: Artificial
<220> FEATURE:
<223> OTHER INFORMATION: an artificially synthesized sequence

<400> SEQUENCE: 216
cgccaauauu uaugugcugc ua                                        22

<210> SEQ ID NO 217
<211> LENGTH: 33
<212> TYPE: DNA
<213> ORGANISM: Artificial
<220> FEATURE:
<223> OTHER INFORMATION: an artificially synthesized sequence

<400> SEQUENCE: 217
ggccgcttcc atcattaccc ggcagtatta ggg                            33

<210> SEQ ID NO 218
<211> LENGTH: 33
<212> TYPE: DNA
<213> ORGANISM: Artificial
<220> FEATURE:
<223> OTHER INFORMATION: an artificially synthesized sequence

<400> SEQUENCE: 218
tcgaccctaa tactgccggg taatgatgga agc                            33

<210> SEQ ID NO 219
<211> LENGTH: 60
<212> TYPE: RNA
<213> ORGANISM: Artificial
<220> FEATURE:
<223> OTHER INFORMATION: an artificially synthesized sequence
<220> FEATURE:
<221> NAME/KEY: misc_feature
<222> LOCATION: (22)..(47)
<223> OTHER INFORMATION: n is any one of a, g, c, or u

<400> SEQUENCE: 219
gacggcgcua ggaucaucaa cnnnnnnnnn nnnnnnnnnn nnnnnnncaa guauucuggu    60

<210> SEQ ID NO 220
<211> LENGTH: 60
<212> TYPE: RNA
<213> ORGANISM: Artificial
<220> FEATURE:
<223> OTHER INFORMATION: an artificially synthesized sequence
<220> FEATURE:
<221> NAME/KEY: misc_feature
<222> LOCATION: (14)..(39)
<223> OTHER INFORMATION: n is any one of a, g, c, or u

<400> SEQUENCE: 220
accagaauac aacnnnnnnn nnnnnnnnnn nnnnnnnnnc aagaugaucc uagcgccguc    60

<210> SEQ ID NO 221
<211> LENGTH: 22
<212> TYPE: RNA
<213> ORGANISM: Artificial
<220> FEATURE:
<223> OTHER INFORMATION: an artificially synthesized sequence
```

```
-continued

<400> SEQUENCE: 221
ucaacaucag uccgauaagc ua                                            22

<210> SEQ ID NO 222
<211> LENGTH: 23
<212> TYPE: RNA
<213> ORGANISM: Artificial
<220> FEATURE:
<223> OTHER INFORMATION: an artificially synthesized sequence

<400> SEQUENCE: 222
uccaucauua cccggcagua uua                                           23
```